US011357853B2

(12) United States Patent
Rombaut et al.

(10) Patent No.: US 11,357,853 B2
(45) Date of Patent: Jun. 14, 2022

(54) INHIBITION OF A LNCRNA FOR TREATMENT OF NEUROBLASTOMA

(71) Applicant: Universiteit Gent, Ghent (BE)

(72) Inventors: Dries Rombaut, Ghent (BE); Pieter Mestdagh, Bruges (BE); Steve Lefever, Dendermonde (BE)

(73) Assignee: Universiteit Gent, Ghent (BE)

( * ) Notice: Subject to any disclaimer, the term of this patent is extended or adjusted under 35 U.S.C. 154(b) by 151 days.

(21) Appl. No.: 16/965,876

(22) PCT Filed: Jan. 24, 2019

(86) PCT No.: PCT/EP2019/051757
§ 371 (c)(1),
(2) Date: Jul. 29, 2020

(87) PCT Pub. No.: WO2019/149616
PCT Pub. Date: Aug. 8, 2019

(65) Prior Publication Data
US 2021/0015921 A1    Jan. 21, 2021

(30) Foreign Application Priority Data
Feb. 2, 2018   (EP) .................................. 18154813

(51) Int. Cl.
| C12N 15/113 | (2010.01) |
| C12Q 1/6886 | (2018.01) |
| A61K 45/06 | (2006.01) |
| A61P 35/00 | (2006.01) |
| G01N 33/49 | (2006.01) |
| C07H 21/02 | (2006.01) |

(52) U.S. Cl.
CPC .............. A61K 45/06 (2013.01); A61P 35/00 (2018.01); C12N 15/113 (2013.01); C12Q 1/6886 (2013.01); G01N 33/49 (2013.01)

(58) Field of Classification Search
None
See application file for complete search history.

(56) References Cited

U.S. PATENT DOCUMENTS 5,185,444 A    2/1993   Summerton et al.
5,217,866 A    6/1993   Summerton et al.

FOREIGN PATENT DOCUMENTS

WO    2016/085944 A1    6/2016
WO    2017/201606 A1    11/2017

OTHER PUBLICATIONS

Consortium, "An Integrated Encyclopedia of DNA Elements in the Human Genome," Nature, vol. 489, (Sep. 2012), pp. 57-74.

Cui et al., "Genome-Wide Identification of Differential Methylation Between Primary and Recurrent Hepatocellular Carcinomas," Molecular Carcinogenesis, vol. 55, No. 7, (Jul. 2, 2015), pp. 1163-1174.
Durinck et al., "Epigenetic Regulation of Neuroblastoma Development," Cell and Tissue Research, vol. 372, No. 2, (Jan. 19, 2018), pp. 309-324.
Gutschner et al., "The Hallmarks of Cancer, A Long Non-Coding RNA Point of View," RNA Biology, vol. 9, No. 6, (Jun. 2012), pp. 703-719.
International Search Report for International Application No. PCT/EP2019/051757, dated Apr. 11, 2019, 6 pages.
International Written Opinion for International Application No. PCT/EP2019/051757, dated Apr. 11, 2019, 5 pages.
Larson et al., "CRISPR Interference (CRISPRi) for Sequence-Specific Control of Gene Expression," Nature Protocols, vol. 8 No. 11, (2013), pp. 2180-2196.
Li et al., "Long Noncoding RNA pancEts-1 Promotes Neuroblastoma Progression through hnRNPK-Mediated [beta]-Catenin Stabilization," Cancer research, vol. 78, No. 5, (Jan. 8, 2018), pp. 1169-1183.
Liu et al., "Effects of a Novel Long Noncoding RNA, lncUSMycN, on N-Myc Expression and Neuroblastoma Progression," Journal of the national cancer institute, vol. 106, No. 7, (Jun. 6, 2014), pp. 1-11.
Ma et al., "On the Classification of Long Non-Coding RNAs," RNA Biology, vol. 10, Issue 6, (Jun. 2013), pp. 924-933.
Maris et al., "Recent Advances in Neuroblastoma," N. Engl. J. Med., vol. 362, No. 23, (Jun. 2010), pp. 2202-2211.
Mazar et al., "The Long Non-Coding RNA GAS5 Differentially Regulates Cell Cycle Arrest And Apoptosis Through Activation of BRCA1 and p53 in Human Neuroblastoma," Oncotarget, vol. 8, No. 4, (Dec. 27, 2016), pp. 6589-6607.
Pandey et al., "Long Noncoding RNAs and Neuroblastoma," Oncotarget, vol. 6, No. 21, (Jun. 10, 2015), pp. 18265-18275.
Park et al., "Neuroblastoma: Biology, Prognosis, and Treatment," Pediatr. Clin. N. Am., vol. 55, (2008), pp. 97-120.
Raabe et al., "Prevalence and Functional Consequence of PHOX2B Mutations in Neuroblastoma," Oncogene, vol. 27, No. 4, (Jul. 16, 2007), pp. 469-476.
Sarin et al., "Inhibition of Acquired Immunodeficiency Syndrome Virus by Oligodeoxynucleoside Methylphosphonates," Proc. Natl. Acad. Sci. USA, vol. 85, (Oct. 1988), pp. 7448-7451.
Stein et al., "Physicochemical Properties of Phosphorothioate Oligodeoxynucleotides," Nucleic Acids Research, vol. 6, No. 8, (1988), pp. 3209-3221.
Yang et al., "PHOX2B Is Associated With Neuroblastoma Cell Differentiation," Cancer Biotherapy & Radiopharmaceuticals, vol. 31, No. 2, (Mar. 17, 2016), pp. 44-51.

*Primary Examiner* — Sean McGarry
(74) *Attorney, Agent, or Firm* — TraskBritt

(57) ABSTRACT

A treatment of cancer, particularly the treatment of neuroblastoma. Indeed, the discloses that a particular long non-coding RNA (lncRNA) is specifically up-regulated in neuroblastoma cells as compared to other cancer cells and that high expression of the lncRNA correlates with a lower survival probability. Inhibition of this lncRNA in neuroblastoma cells leads to a reduction in cell growth and induction of apoptosis and is a novel therapeutic strategy in the treatment of neuroblastoma.

8 Claims, 34 Drawing Sheets

Specification includes a Sequence Listing.

| Gene | JS Score | 0 | 1 |
|---|---|---|---|
| PHOX2A | 0.53 | | |
| PHOX2B | 0.52 | | |
| lnc-PHOX2B-2 | 0.5 | | |
| lnc-LIMCH1-2 | 0.46 | | |

SEQUENCE LISTING

```
<160> NUMBER OF SEQ ID NOS: 34

<210> SEQ ID NO 1
<211> LENGTH: 632
<212> TYPE: DNA
<213> ORGANISM: Homo sapiens

<400> SEQUENCE: 1
tcatcatgta taaatggtg cagtaggatg caaaatttcc acttgtttat aagtgtatcg      60
ccgagaaatg tataaaataa tcgagaccgg cggaggcagg tcagagccgt ctggaatgcg     120
cgcaccttca accactttgg gaggccgagg caggtggatc acctcaggtc aggagttcga     180
gaccagcgtg accaacatgg tgaaacccgt ctctactaaa aatacaaaaa attagatggg     240
tatggtggcg cgtgcctgtc tgctactcgg gaggctgagg caggagaacc ttggaggcaa     300
aggttgcagt gagctgagat caagccaccg cactccagcc tgggcgacag cgcaaaactt     360
tgtctcaaaa aaaaaaaaaa aaaaaagtcc gcagtatggt tttcacatta tcactctcaa     420
tgccattgga ggtaggtcca agctggtgtc tctttgatta gtctccctaa acccatctat     480
tcatttacta gccattagtt attctttaat tgagtccaaa aatgtttgtg aggagatagt     540
cccatatgag attaaaagaa agaagaaaa caaaacaaca aacaaacaaa caaaacagaa      600
aatcaggtgt agtggacact gaagagtttc tg                                   632
```

```
<210> SEQ ID NO 2
<211> LENGTH: 1424
<212> TYPE: DNA
<213> ORGANISM: Homo sapiens

<400> SEQUENCE: 2
tcatcatgta taaatggtg cagtaggatg caaaatttcc acttgttat aagtgtatcg        60 ccgagaaatg tataaaataa tcgagaccgg cggaggcagg tcagagccgt ctggaatgcg       120
cgcaccttca acgtatttg agattattc gcactgaatt ttctgcccgc caagaacgaa        180
taggattgcc aagccacacc acttttgga gcccgcttat tcgcgcctat ccaccctctc       240
ctgtgcccca ggttccctga gcacgggaat cctttccggg catggccaag tttgttcggt       300
ggctcagagc gggaagggaa gtgcagttcg acacctgtcc agctgctccg cttggagatc       360
aaaggccggc tatgggctga cgacagatt tacgggacgg tggtacagat taaggcgaga       420
accctgccgg tcctggactc gagttcgcac ccaaggaaag cgtacaggtc cctggaagcg       480
ggtggatgtc ggagaggccg aggcagcctg cgctgtggcc aggcaggctt ggtgggcttt       540
agtctcagta tgtgttcttt aaagtcttga caggttatta gtaaaggaag gggcacccca       600
gggtcatgaa gatgcttctc gctctggccc aagcatgctg aggctcgctt attcctcggc       660
caggcccagt aaaacagctc aagcacagcc tggagtcttc ccgcatctgc gcgggagtag       720
agtctggctt tgggccccgc gtaccccgca gtcgtcgggg accagttcga ggccacggga       780 agggttccg cggcagggcg cggagtaaag aggggaagaa ggaatcctct ccgcgtgatc       840
agtagggcgg gcttgtgata ctctcacacc caggttccag ctcagccccc aaactgctgc       900
cccaagaaaa caagttgggg agtgtggatt tagacataac aacgggtgtg agctgatgtc       960
cttacaacca aaatattga gactagaaat tcagctccga atccacgacc ctcagattga      1020
tgcttaatcg caccctcgac tccagaaaag ctgccgggga cagacatgga caggttttgc      1080
caagggttca ttaaaatagt ctgcactgga ataaccgggg tgcaagagat cacgtcttca      1140
ctcagggctt tggggatccc ctcgtcgccc caggtcagtg ggtggggagg agggcaaact      1200
tctgtctttt gtttgtgggt gagggatgcg aattgtggca gcagccgaga aaaggggga       1260 aattaattgc agccaattaa taattaatcc cctttaaaca gctttattat ctcttctggg      1320
cgacagagat ttgtctgata acccctgaa gaccaaatgt caagtttaac caaatagtta      1380
ttgctttatc aacccgagtc tgcaaataaa ttaatcaaaa gcaa                     1424

<210> SEQ ID NO 3
<211> LENGTH: 555
<212> TYPE: DNA
<213> ORGANISM: Homo sapiens

<400> SEQUENCE: 3
tggtgcagta ggatgcaaaa tttccacttg tttataagtg tatcgccgag aaatgtataa        60
aataatcgag accggcggag gcaggtcaga gccgtctgga atgcgcgcac cttcaacgaa       120
caatgccaac attgaagtcc tcggttggag tctgcacagt tggagatctt tggtgccatt       180
ttagacatct ttggatttca tcaatcaaac tgactgcaat tttccataaa aaccctgaat       240
ttgggtcaga aagtgggcaa agtagataaa gatcattcga gctgtcttat aagatgataa       300
atagatatcc tttcaggcca acaatgccaa agtgcagttt tgtgattccc ttccatgggt       360
tctgaatgca gtgagtcgaa acgatttcta catgttttcc catggtttag gaggtgtctt       420
tacatacttg tcaatagtag cctgaccttt ttccccatgg agttgctaag tgtgttttgt       480
``` ttgttgctttt gagtactttt ttcttgttgt ttgtgtgtgt gttgcacaaa atacacaaga    540
aaataaaggt ttttt    555

<210> SEQ ID NO 4
<211> LENGTH: 1384
<212> TYPE: DNA
<213> ORGANISM: Homo sapiens

<400> SEQUENCE: 4
cttgtttata agtgtatcgc cgagaaatgt ataaaataat cgagaccggc ggaggcaggt    60
cagagccgtc tggaatgcgc gcaccttcaa cggtatttgg agattattcg cactgaattt    120
tctgcccgcc aagaacgaat aggattgcca agccacacca cttttggag cccgcttatt     180 cgcgcctatc caccctctcc tgtgcccag gttccctgag cacgggaatc ctttccgggc      240
atggccaagt tgttcggtg gctcagagcg ggaagggaag tgcagttcga cacctgtcca     300
gctgctccgc ttggagatca aaggccggct atgggctgag cgacagattt acgggacggt    360
ggtacagatt aaggcgagaa ccctgccggt cctggactcg agttcgcacc caaggaaagc    420
gtacaggtcc ctggaagcgg gtggatgtcg gagaggccga ggcagcctgc gctgtggcca    480
ggcaggcttg gtgggcttta gtctcagtat gtgttcttta aagtcttgac aggttattag    540
taaaggaagg ggcaccccag ggtcatgaag atgcttctcg ctctggccca agcatgctga    600
ggctcgctta ttcctcggcc aggcccagta aaacagctca agcacagcct ggagtcttcc    660
cgcatctgcg cgggagtaga gtctggcttt gggccccgcg taccccgcag tcgtcgggga    720
ccagttcgag gccacgggaa gggttttccgc ggcaggcgc ggagtaaaga ggggaagaag     780
gaatcctctc cgcgtgatca gtagggcggg cttgtgatac tctcacaccc aggttccagc    840
tcagccccca aactgctgcc ccaagaaaac aagttgggga gtgtggattt agacataaca    900
acgggtgtga gctgatgtcc ttacaaccaa aaatattgag actagaaatt cagctccgaa    960
tccacgaccc tcagattgat gcttaatcgc accctcgact ccagaaaagc tgccggggac    1020
agacatggac aggttttgcc aagggttcat taaaatagtc tgcactggaa taaccggggt    1080
gcaagagatc acgtcttcac tcagggcttt ggggatcccc tcgtcgcccc aggtcagtgg    1140
gtggggagga gggcaaactt ctgtcttttg tttgtgggtg agggatgcga attgtggcag    1200
cagccgagaa aagggggaa attaattgca gccaattaat aattaatccc ctttaaacag    1260
ctttattatc tcttctgggc gacagagatt tgtctgataa cccctgaag accaaatgtc     1320 aagtttaacc aaatagttat tgctttatca acccgagtct gcaaataaat taatcaaaag    1380
caaa    1384

<210> SEQ ID NO 5
<211> LENGTH: 1362
<212> TYPE: DNA
<213> ORGANISM: Homo sapiens

<400> SEQUENCE: 5
gccgagaaat gtataaaata atcgagaccg gcggaggcag gtcagagccg tctggaatgc    60
gcgcaccttc aacggtattt ggagattatt cgcactgaat tttctgcccg ccaagaacga    120
ataggattgc caagccacac cactttttgg agcccgctta ttcgcgccta ccaccctct     180 cctgtgcccc aggttccctg agcacgggaa tcctttccgg gcatggccaa gtttgttcgg    240
tggctcagag cgggaaggga agtgcagttc gacacctgtc cagctgctcc gcttggagat    300
caaaggccgg ctatgggctg agcgacagat ttacgggacg gtggtacaga ttaaggcgag    360

| | |
|---|---|
| aaccctgccg gtcctggact cgagttcgca cccaaggaaa gcgtacaggt ccctggaagc | 420 |
| gggtggatgt cggagaggcc gaggcagcct gcgctgtggc caggcaggct tggtgggctt | 480 |
| tagtctcagt atgtgttctt taaagtcttg acaggttatt agtaaaggaa ggggcacccc | 540 |
| agggtcatga agatgcttct cgctctggcc caagcatgct gaggctcgct tattcctcgg | 600 |
| ccaggcccag taaacagct caagcacagc ctggagtctt cccgcatctg cgcgggagta | 660 |
| gagtctggct ttgggccccg cgtacccccgc agtcgtcggg gaccagttcg aggccacggg | 720 |
| aagggtttcc gcggcagggc gcggagtaaa gaggggaaga aggaatcctc tccgcgtgat | 780 |
| cagtagggcg ggcttgtgat actctcacac ccaggttcca gctcagcccc caaactgctg | 840 |
| ccccaagaaa acaagttggg gagtgtggat ttagacataa caacgggtgt gagctgatgt | 900 |
| ccttacaacc aaaaatattg agactagaaa ttcagctccg aatccacgac cctcagattg | 960 |
| atgcttaatc gcaccctcga ctccagaaaa gctgccgggg acagacatgg acaggttttg | 1020 |
| ccaagggttc attaaaatag tctgcactgg aataaccggg gtgcaagaga tcacgtcttc | 1080 |
| actcagggct ttggggatcc cctcgtcgcc ccaggtcagt gggtggggag gagggcaaac | 1140 |
| ttctgtcttt tgtttgtggg tgagggatgc gaattgtggc agcagccgag aaaagggggg | 1200 |
| aaattaattg cagccaatta ataattaatc cccttaaac agctttatta tctcttctgg | 1260 |
| gcgacagaga tttgtctgat aaccccctga agaccaaatg tcaagtttaa ccaaatagtt | 1320 |
| attgctttat caacccgagt ctgcaaataa attaatcaaa ag | 1362 |

<210> SEQ ID NO 6
<211> LENGTH: 1625
<212> TYPE: DNA
<213> ORGANISM: Homo sapiens

<400> SEQUENCE: 6

| | |
|---|---|
| gtccgccttt agcgatggtt tgggaacccg ggcgctggaa aggcgcgggt gcggagggcg | 60 |
| gctgagccgc gcggctgcgg caccgtgggc gcgagacccc tgcggagagg agcgcgcgga | 120 |
| cgccgggga agcgcctcgg ggcggctgga ggcgcagcac cctgggggag ccggggcgcg | 180 |
| ggagagacaa aactgttcga accttctctc ccttccccac cccagcgcc caaacccggg | 240 |
| gcgggtgagc gcgacccttg cagcgacccc ttgccgagcc ctgcccgcgc gattactaag | 300 |
| gagacgcggc ctccggcact gccgtccccg cgccgtttga aaacgatcc atcagcgggg | 360 |
| tatttggaga ttattcgcac tgaattttct gcccgccaag aacgaatagg attgccaagc | 420 |
| cacaccactt tttggagccc gcttattcgc gcctatccac cctctcctgt gcccaggtt | 480 |
| ccctgagcac gggaatcctt tccgggcatg gccaagtttg ttcggtggct cagagcggga | 540 |
| agggaagtgc agttcgacac ctgtccagct gctccgcttg gagatcaaag gccggctatg | 600 |
| ggctgagcga cagatttacg ggacggtggt acagattaag gcgagaaccc tgccggtcct | 660 |
| ggactcgagt tcgcacccaa ggaaagcgta caggtccctg gaagcgggtg gatgtcggag | 720 |
| aggccgaggc agcctgcgct gtggccaggc aggcttggtg ggctttagtc tcagtatgtg | 780 |
| ttctttaaag tcttgacagg ttattagtaa aggaaggggc accccagggt catgaagatg | 840 |
| cttctcgctc tggcccaagc atgctgaggc tcgcttattc ctcggccagg cccagtaaaa | 900 |
| cagctcaagc acagcctgga gtcttcccgc atctgcgcgg gagtagagtc tggctttggg | 960 |
| ccccgcgtac cccgcagtcg tcggggacca gttcgaggcc acgggaaggg tttccgcggc | 1020 |
| agggcgcgga gtaaagaggg gaagaaggaa tcctctccgc gtgatcagta gggcgggctt | 1080 |

```
gtgatactct cacacccagg ttccagctca gcccccaaac tgctgcccca agaaaacaag    1140
ttggggagtg tggatttaga cataacaacg ggtgtgagct gatgtcctta caaccaaaaa    1200
tattgagact agaaattcag ctccgaatcc acgaccctca gattgatgct taatcgcacc    1260
ctcgactcca gaaaagctgc cggggacaga catggacagg ttttgccaag ggttcattaa    1320
aatagtctgc actggaataa ccggggtgca agagatcacg tcttcactca gggctttggg    1380
gatcccctcg tcgccccagg tcagtgggtg gggaggaggg caaacttctg tcttttgttt    1440
gtgggtgagg gatgcgaatt gtggcagcag ccgagaaaag gggggaaatt aattgcagcc    1500
aattaataat taatccccctt taaacagctt tattatctct tctgggcgac agagatttgt    1560
ctgataaccc cctgaagacc aaatgtcaag tttaaccaaa tagttattgc tttatcaacc    1620
cgagt                                                                 1625
```

<210> SEQ ID NO 7
<211> LENGTH: 1647
<212> TYPE: DNA
<213> ORGANISM: Homo sapiens

<400> SEQUENCE: 7

```
gtccgccttt agcgatggtt tgggaacccg ggcgctggaa aggcgcgggt gcggagggcg      60
gctgagccgc gcggctgcgg caccgtgggc gcgagacccc tgcggagagg agcgcgcgga     120
cgccggggga agcgcctcgg ggcgctggag gcgcagcac cctgggggag ccggggcgcg      180
ggagagacaa aactgttcga accttctctc ccttccccac ccccagcgcc caaacccggg     240
gcgggtgagc gcgacccttg cagcgacccc ttgccgagcc ctgcccgcgc gattactaag     300
gagacgcggc ctccggcact gccgtccccg cgccgtttga aaacggatcc atcagcgggg     360
tatttggaga ttattcgcac tgaattttct gcccgccaag aacgaatagg attgccaagc     420
cacaccactt tttggagccc gcttattcgc gcctatccac cctctcctgt gccccaggtt     480
ccctgagcac gggaatcctt tccgggcatg gccaagtttg ttcggtggct cagagcggga     540
agggaagtgc agttcgacac ctgtccagct gctccgcttg gagatcaaag gccggctatg     600
ggctgagcga cagatttacg ggacggtggt acagattaag gcgagaaccc tgccggtcct     660
ggactcgagt tcgcacccaa ggaaagcgta caggtccctg gaagcgggtg gatgtcggag     720
aggccgaggc agcctgcgct gtggccaggc aggcttggtg ggctttagtc tcagtatgtg     780
ttctttaaag tcttgacagg ttattagtaa aggaaggggc accccagggt catgaagatg     840
cttctcgctc tggcccaagc atgctgaggc tcgcttattc ctcggccagg cccagtaaaa     900
cagctcaagc acagcctgga gtcttcccgc atctgcgcgg gagtagagtc tggctttggg     960
ccccgcgtac cccgcagtcg tcggggacca gttcgaggcc acgggaaggg tttccgcggc    1020
agggcgcgga gtaaagaggg gaagaaggaa tcctctccgc gtgatcagta gggcgggctt    1080
gtgatactct cacacccagg ttccagctca gcccccaaac tgctgcccca agaaaacaag    1140
ttggggagtg tggatttaga cataacaacg ggtgtgagct gatgtcctta caaccaaaaa    1200
tattgagact agaaattcag ctccgaatcc acgaccctca gattgatgct taatcgcacc    1260
ctcgactcca gaaaagctgc cggggacaga catggacagg ttttgccaag ggttcattaa    1320
aatagtctgc actggaataa ccggggtgca agagatcacg tcttcactca gggctttggg    1380
gatcccctcg tcgccccagg tcagtgggtg gggaggaggg caaacttctg tcttttgttt    1440
gtgggtgagg gatgcgaatt gtggcagcag ccgagaaaag gggggaaatt aattgcagcc    1500
aattaataat taatccccctt taaacagctt tattatctct tctgggcgac agagatttgt    1560
```
ctgataaccc cctgaagacc aaatgtcaag tttaaccaaa tagttattgc tttatcaacc    1620
cgagtctgca aataaattaa tcaaaag                                        1647

<210> SEQ ID NO 8
<211> LENGTH: 931
<212> TYPE: DNA
<213> ORGANISM: Homo sapiens

<400> SEQUENCE: 8
gagggcgcgc gccgccccgc gctccctccc tccccggtaa ttgatggagg ctgccgaaaa      60
aagataatta gttttatgta tataatattt gatcatgaaa atattctttg ccttattttg     120
gtataggaga tctgtaatat atgttaaaat agttaatttt ttattatctc tttgtttggc     180
ggcagcccgg cctatccgaa attaccggag catcaactga aaatgtaggc aatgtaagca     240
atgttaaatc taatttttct gtccaaaacc taattagcca ttttaaaaaa ggttaacgcc     300
agcgcctgag acggttttg tttaataatc ctattactga cggctcatca tgtataaaat      360
ggtgcagtag gatgcaaaat ttccacttgt ttataagtgt atcgccgaga atgtataaa      420 ataatcgaga ccggcggagg caggtcgaga ccgtctggaa tgcgcgcacc ttcaacgaac     480
aatgccaaca ttgaagtcct cggttggagt ctgcacagtt ggagatcttt ggtgccattt     540
tagacatctt tggatttcat caatcaaact gactgcaatt ttccataaaa accctgaatt     600
tgggtcagaa agtgggcaaa gtagataaag atcattcgag ctgtcttata agatgataaa     660
tagatatcct ttcaggccaa caatgccaaa gtgcagtttt tgtgattccct tccatgggtt    720 ctgaatgcag tgagtcgaaa cgatttctac atgttttccc atggtttagg aggtgtcttt     780
acatacttgt caatagtagc ctgaccttt tccccatgga gttgctaagt gtgttttgtt      840
tgttgctttg agtactttt tcttgttgtt tgtgtgtgtg ttgcacaaaa tacacaagaa      900
aataaaggtt ttttttcttt tattgctcaa a                                   931

<210> SEQ ID NO 9
<211> LENGTH: 728
<212> TYPE: DNA
<213> ORGANISM: Homo sapiens

<400> SEQUENCE: 9
acttgtttat aagtgtatcg ccgagaaatg tataaaataa tcgagaccgg cggaggcagg      60
tcagagccgt ctggaatgcg cgcaccttca acgaacaatg ccaacattga agtcctcggt     120
tggagtctgc acagttggag atctttggtg ccattttaga catctttgga tttcatcaat     180
caaactgact gcaattttcc ataaaaaccc tgaatttggg tcagaaagtg ggcaaagtag     240
ataaagatca ttcgagctgt cttataagat gataaataga tatcctttca ggccaacaat     300
gccaaagtgc agttttgtga ttcccttcca tgggttctga atgcagtgag tcgaaacgat     360
ttctacatgt tttcccatgg tttaggaggt gtctttacat acttgtcaat agtagcctga     420
cctttttccc catggagttg ctaagtgtgt tttgtttgtt gctttgagta cttttttctt     480
gttgtttgtg tgtgttgc acaaaataca caagaaaata aaggttttt ttcttttatt        540 gctcaaatca ataggatatg ggtctgatct agataattct ctgcatatag actggtttca     600
gtagcccttg agttcatgta gaaattccat ttgctctgca gttgctcttg aggcactttg     660
gacaccattt tgggcaccat gctgggatgt aaactcactt tcttaacaac aacaacaaca    720
acaacaac                                                             728

```
<210> SEQ ID NO 10
<211> LENGTH: 592
<212> TYPE: DNA
<213> ORGANISM: Homo sapiens

<400> SEQUENCE: 10
acttgtttat aagtgtatcg ccgagaaatg tataaaataa tcgagaccgg cggaggcagg     60
tcagagccgt ctggaatgcg cgcaccttca accactttgg gaggccgagg caggtggatc    120
acctcaggtc aggagttcga gaccagcgtg accaacatgg tgaaacccgt ctctactaaa    180
aatacaaaaa attagatggg tatggtggcg cgtgcctgtc tgctactcgg gaggctgagg    240
caggagaacc ttggaggcaa aggttgcagt gagctgagat caagccaccg cactccagcc    300
tgggcgacag cgcaaaactt tgtctcaaaa aaaaaaaaaa aaaaaagtcc gcagtatggt    360
tttcacatta tcactctcaa tgccattgga ggtaggtcca agctggtgtc tctttgatta    420
gtctccctaa acccatctat tcatttacta gccattagtt attctttaat tgagtccaaa    480
aatgtttgtg aggagatagt cccatatgag attaaaagaa agaaagaaaa caaaacaaca    540
aacaaacaaa caaaacagaa atcaggtgt agtggacact gaagagtttc tg            592

<210> SEQ ID NO 11
<211> LENGTH: 1385
<212> TYPE: DNA
<213> ORGANISM: Homo sapiens

<400> SEQUENCE: 11
acttgtttat aagtgtatcg ccgagaaatg tataaaataa tcgagaccgg cggaggcagg     60
tcagagccgt ctggaatgcg cgcaccttca acggtatttg agattattc gcactgaatt    120 ttctgcccgc caagaacgaa taggattgcc aagccacacc acttttttgga gcccgcttat    180 tcgcgcctat ccaccctctc ctgtgcccca ggttccctga gcacgggaat cctttccggg    240 catgccaag tttgttcggt ggctcagagc gggaagggaa gtgcagttcg acacctgtcc    300
agctgctccg cttggagatc aaaggccggc tatgggctga gcgacagatt tacgggacgg    360
tggtacagat taaggcgaga accctgccgg tcctggactc gagttcgcac ccaaggaaag    420
cgtacaggtc cctggaagcg ggtggatgtc ggagaggccg aggcagcctg cgctgtggcc    480
aggcaggctt ggtgggcttt agtctcagta tgtgttcttt aaagtcttga caggttatta    540
gtaaaggaag gggcacccca gggtcatgaa gatgcttctc gctctggccc aagcatgctg    600
aggctcgctt attcctcggc caggcccagt aaaacagctc aagcacagcc tggagtcttc    660
ccgcatctgc gcgggagtag agtctggctt tgggccccgc gtaccccgca gtcgtcgggg    720
accagttcga ggccacggga agggtttccg cggcagggcg cggagtaaag aggggaagaa    780
ggaatcctct ccgcgtgatc agtagggcgg gcttgtgata ctctcacacc caggttccag    840
ctcagccccc aaactgctgc cccaagaaaa caagttgggg agtgtggatt tagacataac    900
aacgggtgtg agctgatgtc cttacaacca aaaatattga gactagaaat tcagctccga    960
atccacgacc ctcagattga tgcttaatcg caccctcgac tccagaaaag ctgccgggga   1020
cagacatgga caggttttgc caagggttca ttaaaatagt ctgcactgga ataaccgggg   1080
tgcaagagat cacgtcttca ctcagggctt tggggatccc ctcgtcgccc caggtcagtg   1140
ggtggggagg agggcaaact tctgtctttt gtttgtgggt gagggatgcg aattgtggca   1200
gcagccgaga aaagggggga aattaattgc agccaattaa taattaatcc cctttaaaca   1260
gctttattat ctcttctggg cgacagagat ttgtctgata accccctgaa gaccaaatgt   1320
```

```
caagtttaac caaatagtta ttgctttatc aacccgagtc tgcaaataaa ttaatcaaaa    1380
gcaaa                                                                1385

<210> SEQ ID NO 12
<211> LENGTH: 1425
<212> TYPE: DNA
<213> ORGANISM: Homo sapiens

<400> SEQUENCE: 12
tcatcatgta taaaatggtg cagtaggatg caaaatttcc acttgtttat aagtgtatcg      60
ccgagaaatg tataaaataa tcgagaccgg cggaggcagg tcagagccgt ctggaatgcg     120
cgcaccttca acggtatttg agattattc gcactgaatt ttctgcccgc caagaacgaa      180
taggattgcc aagccacacc acttttggga gcccgcttat tcgcgcctat ccaccctctc     240
ctgtgcccca ggttccctga gcacgggaat cctttccggg catggccaag tttgttcggt     300
ggctcagagc gggaagggaa gtgcagttcg acacctgtcc agctgctccg cttggagatc     360
aaaggccggc tatgggctga gcgacagatt tacgggacgg tggtacagat taaggcgaga     420
accctgccgg tcctggactc gagttcgcac ccaaggaaag cgtacaggtc cctggaagcg     480
ggtggatgtc ggagaggccg aggcagcctg cgctgtggcc aggcaggctt ggtgggcttt     540
agtctcagta tgtgttcttt aaagtcttga caggttatta gtaaaggaag ggcaccccca     600
gggtcatgaa gatgcttctc gctctggccc aagcatgctg aggctcgctt attcctcggc     660
caggcccagt aaaacagctc aagcacagcc tggagtcttc ccgcatctgc gcgggagtag     720
agtctggctt tgggccccgc gtaccccgca gtcgtcgggg accagttcga ggccacggga     780
agggtttccg cggcagggcg cggagtaaag aggggaagaa ggaatcctct ccgcgtgatc     840
agtagggcgg gcttgtgata ctctcacacc caggttccag ctcagccccc aaactgctgc     900
cccaagaaaa caagttgggg agtgtggatt tagacataac aacgggtgtg agctgatgtc     960
cttacaacca aaaatattga gactagaaat tcagctccga atccacgacc ctcagattga    1020
tgcttaatcg caccctcgac tccagaaaag ctgccgggga cagacatgga caggttttgc    1080
caagggttca ttaaaatagt ctgcactgga ataaccgggg tgcaagagat cacgtcttca    1140
ctcagggctt tggggatccc ctcgtcgccc caggtcagtg ggtggggagg agggcaaact    1200
tctgtctttt gtttgtgggt gagggatgcg aattgtggca gcagccgaga aaagggggga    1260
aattaattgc agccaattaa taattaatcc cctttaaaca gctttattat ctcttctggg    1320
cgacagagat ttgtctgata accccctgaa gaccaaatgt caagtttaac caaatagtta    1380
ttgctttatc aacccgagtc tgcaaataaa ttaatcaaaa gcaaa                    1425

<210> SEQ ID NO 13
<211> LENGTH: 16
<212> TYPE: DNA
<213> ORGANISM: Artificial Sequence
<220> FEATURE:
<223> OTHER INFORMATION: LNA2 ASO Sequence for lnc-PHOX2b-2 Perturbation
<220> FEATURE:
<221> NAME/KEY: misc_feature
<222> LOCATION: (1)..(1)
<223> OTHER INFORMATION: locked deoxyguanosine (G*)
<220> FEATURE:
<221> NAME/KEY: misc_feature
<222> LOCATION: (2)..(2)
<223> OTHER INFORMATION: locked deoxycytidine (C*)
<220> FEATURE:
<221> NAME/KEY: misc_feature
<222> LOCATION: (3)..(3)
```

```
<223> OTHER INFORMATION: locked thymine (T*)
<220> FEATURE:
<221> NAME/KEY: misc_feature
<222> LOCATION: (4)..(4)
<223> OTHER INFORMATION: locked deoxycytosine (C*)
<220> FEATURE:
<221> NAME/KEY: misc_feature
<222> LOCATION: (5)..(5)
<223> OTHER INFORMATION: locked deoxyguanosine (G*)
<220> FEATURE:
<221> NAME/KEY: misc_feature
<222> LOCATION: (6)..(6)
<223> OTHER INFORMATION: locked deoxyadenosine (A*)
<220> FEATURE:
<221> NAME/KEY: misc_feature
<222> LOCATION: (7)..(7)
<223> OTHER INFORMATION: locked deoxyadenosine (A*)
<220> FEATURE:
<221> NAME/KEY: misc_feature
<222> LOCATION: (8)..(8)
<223> OTHER INFORMATION: locked thymine (T*)
<220> FEATURE:
<221> NAME/KEY: misc_feature
<222> LOCATION: (9)..(9)
<223> OTHER INFORMATION: locked deoxyguanosine (G*)
<220> FEATURE:
<221> NAME/KEY: misc_feature
<222> LOCATION: (10)..(10)
<223> OTHER INFORMATION: locked deoxyadenosine (A*)
<220> FEATURE:
<221> NAME/KEY: misc_feature
<222> LOCATION: (11)..(11)
<223> OTHER INFORMATION: locked thymine (T*)
<220> FEATURE:
<221> NAME/KEY: misc_feature
<222> LOCATION: (12)..(12)
<223> OTHER INFORMATION: locked deoxycytidine (C*)
<220> FEATURE:
<221> NAME/KEY: misc_feature
<222> LOCATION: (13)..(15)
<223> OTHER INFORMATION: locked thymine (T*)
<220> FEATURE:
<221> NAME/KEY: misc_feature
<222> LOCATION: (16)..(16)
<223> OTHER INFORMATION: locked deoxyadenosine (A*)

<400> SEQUENCE: 13
gctcgaatga tcttta                                                   16

<210> SEQ ID NO 14
<211> LENGTH: 16
<212> TYPE: DNA
<213> ORGANISM: Artificial Sequence
<220> FEATURE:
<223> OTHER INFORMATION: LNA10 ASO Sequence for lnc-PHOX2B-2
      Perturbation
<220> FEATURE:
<221> NAME/KEY: misc_feature
<222> LOCATION: (1)..(4)
<223> OTHER INFORMATION: locked deoxyadenosine (A*)
<220> FEATURE:
<221> NAME/KEY: misc_feature
<222> LOCATION: (5)..(5)
<223> OTHER INFORMATION: locked deoxycytidine (C*)
<220> FEATURE:
<221> NAME/KEY: misc_feature
<222> LOCATION: (6)..(6)
<223> OTHER INFORMATION: locked thymine (T*)
<220> FEATURE:
<221> NAME/KEY: misc_feature
<222> LOCATION: (7)..(7)
<223> OTHER INFORMATION: locked deoxyguanosine (G*)
<220> FEATURE:
<221> NAME/KEY: misc_feature
<222> LOCATION: (8)..(8)
<223> OTHER INFORMATION: locked deoxyadenosine (A*)
<220> FEATURE:
```

<221> NAME/KEY: misc_feature
<222> LOCATION: (9)..(9)
<223> OTHER INFORMATION: locked thymine (T*)
<220> FEATURE:
<221> NAME/KEY: misc_feature
<222> LOCATION: (10)..(10)
<223> OTHER INFORMATION: locked deoxycytidine (C*)
<220> FEATURE:
<221> NAME/KEY: misc_feature
<222> LOCATION: (11)..(11)
<223> OTHER INFORMATION: locked deoxyguanosine (G*)
<220> FEATURE:
<221> NAME/KEY: misc_feature
<222> LOCATION: (12)..(12)
<223> OTHER INFORMATION: locked deoxyadenosine (A*)
<220> FEATURE:
<221> NAME/KEY: misc_feature
<222> LOCATION: (13)..(13)
<223> OTHER INFORMATION: locked deoxycytidine (C*)
<220> FEATURE:
<221> NAME/KEY: misc_feature
<222> LOCATION: (14)..(14)
<223> OTHER INFORMATION: locked deoxyguanosine (G*)
<220> FEATURE:
<221> NAME/KEY: misc_feature
<222> LOCATION: (15)..(15)
<223> OTHER INFORMATION: locked deoxycytidine (C*)
<220> FEATURE:
<221> NAME/KEY: misc_feature
<222> LOCATION: (16)..(16)
<223> OTHER INFORMATION: locked deoxyadenosine (A*)

<400> SEQUENCE: 14
aaaactgatc gacgca                                                   16

<210> SEQ ID NO 15
<211> LENGTH: 20
<212> TYPE: DNA
<213> ORGANISM: Artificial Sequence
<220> FEATURE:
<223> OTHER INFORMATION: Forward Primer for lnc-PHOX2B-2 expression
      quantification

<400> SEQUENCE: 15
gttggagtct gcacagttgg                                               20

<210> SEQ ID NO 16
<211> LENGTH: 20
<212> TYPE: DNA
<213> ORGANISM: Artificial Sequence
<220> FEATURE:
<223> OTHER INFORMATION: Reverse Primer for lnc-PHOX2B-2 expression
      quantification

<400> SEQUENCE: 16
ctttgcccac tttctgaccc                                               20

<210> SEQ ID NO 17
<211> LENGTH: 18
<212> TYPE: DNA
<213> ORGANISM: Artificial Sequence
<220> FEATURE:
<223> OTHER INFORMATION: intronspanning forward primer for lnc-PHOX2B-2
      expression quantification

<400> SEQUENCE: 17
aatgcgcgca ccttcaac                                                 18

<210> SEQ ID NO 18
<211> LENGTH: 20
<212> TYPE: DNA

```
<213> ORGANISM: Artificial Sequence
<220> FEATURE:
<223> OTHER INFORMATION: intronspanning reverse primer for lnc-PHOX2B-2
      expression quantification

<400> SEQUENCE: 18
ctttgcccac tttctgaccc                                              20

<210> SEQ ID NO 19
<211> LENGTH: 10390
<212> TYPE: DNA
<213> ORGANISM: Homo sapiens

<400> SEQUENCE: 19
gagggcgcgc gccgccccgc gctccctccc tccccggtaa ttgatggagg ctgccgaaaa    60
aagataatta gttttatgta tataatattt gatcatgaaa atattctttg ccttattttg   120
gtataggaga tctgtaatat atgttaaaat agttaatttt ttattatctc tttgtttggc   180
ggcagcccgg cctatccgaa attaccggag catcaactga aaatgtaggc aatgtaagca   240
atgttaaatc taattttttct gtccaaaacc taattagcca ttttaaaaaa ggttaacgcc   300
agcgcctgag acgttttttg tttaataatc ctattactga cggctcatca tgtataaaat   360
ggtgcagtag gatgcaaaat ttccacttgt ttataagtgt atcgccgaga aatgtataaa   420
ataatcgaga ccggcggagg caggtcagag ccgtctggaa tgcgcgcacc ttcaacgtaa   480
gtagccggcg cggccgctca gggttcgagc ccccaccttg gccgggcagg ggacaccttg   540
gccgggcacc tcccgggctt ccgacaaaaa ggcctcggac tttatttggg cccgcgttgg   600
atttctggcg gaatcgccct cggggtcgtt tgggtttgga ggcttccgcc ttgcagggggg   660 tttcacaggg ttgcagcctc gctcgggccc aggccagtgc ggatactcgg gccagggcag   720
cttcgggttc aaggagggtc ggcttctgag ccgctgcgac cgccgccccc gccctgcact   780
gcacccgcct ccggggtgg gggaggggta cttgccgcgg aacggggtct ccgaggaccc   840
tggcccggag aacggaggga aagaaggga cagcagtgag ggccgtgcag ggccacccct   900
aaatgcccct cgaccggctc gcgtcctgcc aagggcaatg tgcagaagcc ctgggcgcgg   960
gtggagtggg acagttctgg aaaattctgg cccttctggg ggtctgggat agttgggaaa  1020
gggagaaaat ggggcagggc gcccagggggg cggggggcggg cgctgggctc ggtggggtct  1080
ccggggagca gccgttactc ctggcgcccc ccgtccgcct ttagcgatgg tttgggaacc  1140
cgggcgctgg aaaggcgcgg gtgcggaggg cggctgagcc gcgcggctgc ggcaccgtgg  1200
gcgcgagacc cctgcggaga ggagcgcgcg gacgccgggg gaagcgcctc ggggcggctg  1260
gaggcgcagc accctggggg agccggggcg cgggagagac aaaactgttc gaaccttctc  1320
tcccttcccc accccagcg cccaaacccg gggcgggtga gcgcgaccct tgcagcgacc  1380
ccttgccgag ccctgcccgc gcgattacta aggagacgcg gcctccggca ctgccgtccc  1440
cgcgccgttt gaaaacggat ccatcagcgg gtaccgggcg tttaagggga tctttctgaa  1500
gggacttgtg ggaaaggaca aaagcaggcg gccccattca gctgaccagt caaaggcgct  1560
aaatggggac atcaaaaggc gccctaactg ggaatacgga tccaatcgca agagaaaaga  1620
acctggtttc ttttcttggc ctcaacaagg ctgaaaagcc gtaaagcaaa taggcaaaga  1680
atgcggagag gggcagaaag gaaaaataaa gaaacaatct catgaatgca ttttctgag   1740 gctttaaatg agaggagtga caacttccta ggcgccgttg ggggccgggg tgcgggtcc   1800 gccgctgcgc ggaccccctc accgagggaa cctctcccgc tcgggcgccc ttgctgtttc  1860
```

```
cacgcgctcc taggcaaggt tcttttgtg ggtgtaatct ttgttcttat ttaaatgcct    1920
aggaagggaa gggaagggaa tggaggataa ggtagagaag ggaaggaaag ggaagggaga    1980
tgggaatgga atgggaaagt aggaaaagcg ggacgcggcg cgaagcccag gtttcccatc    2040
agcttttctg cggtcagatt acgctcacta acacccgagc ttgttatctg acctggccat    2100
ccccgtcaca ttctttctac aagttatctt ttctccaacc agggtatttg agattattc     2160
gcactgaatt ttctgcccgc caagaacgaa taggattgcc aagccacacc acttttggga    2220
gcccgcttat tcgcgcctat ccaccctctc ctgtgcccca ggttccctga gcacgggaat    2280
cctttccggg catggccaag tttgttcggt ggctcagagc gggaagggaa gtgcagttcg    2340
acacctgtcc agctgctccg cttggagatc aaaggccggc tatgggctga gcgacagatt    2400
tacgggacgg tggtacagat taaggcgaga accctgccgg tcctggactc gagttcgcac    2460
ccaaggaaag cgtacaggtc cctggaagcg ggtggatgtc ggagaggccg aggcagcctg    2520
cgctgtggcc aggcaggctt ggtgggcttt agtctcagta tgtgttcttt aaagtcttga    2580
caggttatta gtaaaggaag gggcaccca gggtcatgaa gatgcttctc gctctggccc     2640
aagcatgctg aggctcgctt attcctcggc caggcccagt aaaacagctc aagcacagcc    2700
tggagtcttc ccgcatctgc gcgggagtag agtctggctt gggccccgc gtaccccgca     2760
gtcgtcgggg accagttcga ggccacggga agggtttccg cggcagggcg cggagtaaag    2820
aggggaagaa ggaatcctct ccgcgtgatc agtaggcgg gcttgtgata ctctcacacc     2880
caggttccag ctcagccccc aaactgctgc cccaagaaaa caagttgggg agtgtggatt    2940
tagacataac aacgggtgtg agctgatgtc cttacaacca aaaatattga gactagaaat    3000
tcagctccga atccacgacc ctcagattga tgcttaatcg caccctcgac tccagaaaag    3060
ctgccgggga cagacatgga caggttttgc caagggttca ttaaaatagt ctgcactgga    3120
ataaccgggg tgcaagagat cacgtcttca ctcagggctt tggggatccc ctcgtcgccc    3180
caggtcagtg ggtggggagg agggcaaact tctgtctttt gtttgtgggt gagggatgcg    3240
aattgtggca gcagccgaga aaagggggga aattaattgc agccaattaa taattaatcc    3300
cctttaaaca gctttattat ctcttctggg cgacagagat ttgtctgata acccctgaa     3360
gaccaaatgt caagtttaac caaatagtta ttgctttatc aacccgagtc tgcaaataaa    3420
ttaatcaaaa gcaaatctgt cctttgtgcg gctcatttgc tggtaatgga tggatatgaa    3480
gatttgccga tattattgtc tgtcattcaa tctaacaaag tgaacattta ttgcatatat    3540
attaaaaatt atcccggaat cgagtggcgc cgggttgcat ttattggagt cttcccaggg    3600
gtgaggtccc ctcggatggg ggcgcgtggg atagaaagtg caggagcgcg agtctcaaat    3660
ctctttagga ctctgtgcct gcctctgtcc ccctccccgc agcgacctcc ctctatcccc    3720
ttccctagcc ttcgccccgg agccgcagga cgtgcctgca gcctcctgtc gcgcggccag    3780
ggccagcggg gcgcggggag cccagctact gtcaaaacag agtccttcag ccttaagcac    3840
tcacaagggg tccggcccta ggaaatgtgg ggaggggtg tgattgaaga gagagaaacg     3900
ggaggggac agcttttcctt tgtcttctct cgagttacat catttctaa ttaggcataa     3960
aattgtcttc atacactggt attgcggcct tcataaacat cgccattatg gtttataagg    4020
acgccattgt ggtgaggctg tcccaaaata gaaagagctg ggagggaga ggcctggagt     4080
ccggaggcc ccgctttgtc ctccctggg agaagatgga tggccagtgt cacgcagatg      4140
atgacttggg actattaaat tgtcagaggg gggcagaatc tttaccagcc ccagcgctg     4200
gtggaaaatt ctagaggcag gagccggggg ttcttggatg ggaggggaag gccgggcagc    4260
```

```
tggattcgct gggcaggtgg aaaaagaggt aagttagtcg ctggcagagg cagagcggag    4320
ggcagtgggg gccgaggctt tgatctcctc ccggggcacc ctgacttcgc tgctctctga    4380
gctcagggcc actggatctg gagctgacct ccccacccgat ccccatcgcc aaggttggga   4440
aacaagcagg gctagagaaa tgagaggggc agcgaacccg gaggagcggc ggagggctat    4500
gccaggcggg gagacaattg ttctcattat tcggagctga ggcccaagcc cggccacccg    4560
cccggtcggg gggcgcgtcg ctaactggat ggagatggat ggaggcgccc tgagcccccg    4620
gcgtcgtgtc agacccgggg caattactgt cccgccagga tggacacact gccctgccat    4680
cctgaccccg gcgcgcaggc ccactggccc actggctgcc taagccgcct gggcgattct    4740
ctctctcgcc tttacaataa cccaacttga cataaataac tccctgagc ttgtctacat     4800 ctgcttgacc tcctgaaccc gcggaaaatc ttttgttgca tttagctaac ttacattttt    4860
ctatagaaaa aaaactttta aaactgcata ttctagcctc ggcttattca cctctagttc    4920
ggtctctggt atatgttgga attcacattg cccttccaaa tcatggagga cagttccctc    4980
ctgcgaagac aggtttctcc ctgtttatgc tgcgggcaca agtgtgctgt tccgggtgtc    5040
ctgagttttg caaggtggcc tacagacact tggtgctcca ggaagtggtc aggtctccaa    5100
aatcctctcc cctggtagct ggggtgggag tgggggccaa aagggtgaag aggacagcag    5160
ttctcaggag tgctgatgcc ctgcttggtc ctggctgtct aagggtgcag ctaggcgaca    5220
aggccagttg gcagaagcag ccaggtgccc cacgtgtgct ctctcgctga cctgatctgg    5280
cagggttagg aaggggccag ccctggaagt gccaagctgg cgccatgcac tgcggtcacc    5340
aggtgccaag acaggaggga gctgatggtg gaaagaggat gggaatgatt cagagaattc    5400
tgtggaaatt gcctggtctg gtcactccag ctggcatggg cctggggatg ccagagccag    5460
ctttgctctc caaggcgtcc tctaggtggg gggtgggtag cattgcctgc agcagccttc    5520
ctacctgcca tttcctgcct acttagtccc aggtggctac aagtcagaag atcaggacag    5580
tatctcagaa tttagagatg aagggctct tagaggtcag atggccagag tgactcccaa     5640
gtgtgatggt acagagtctt atctaccccct gataggttta ggaccctaac tgtccctgat   5700
gtctccatcc gcagaggaat atgggaggag ctgaggctgg gcctggccag agtaagctct    5760
gttgaacaca ggccctgtgg cctgggcttt ccttgttcat gggtgaggga agcagcagtt    5820
gcaggaacaa gaccttgact tagcagctgt atcaaatcaa atcaaaacaa acagtaattt    5880
caggattcca aaactctggg gccagttttt cttataacac attttttttcc tttttttttt   5940 tttttgaacg cggtggctca tgcctgtaat tccagcactt tgggaggccg aggcaggtgg    6000
atcacctcag gtcaggagtt cgagaccagc gtgaccaaca tggtgaaacc cgtctctact    6060
aaaaatacaa aaaattagat gggtatgtg gcgcgtgcct gtctgctact cgggaggctg     6120
aggcaggaga accttggagg caaaggttgc agtgagctga gatcaagcca ccgcactcca    6180
gcctgggcga cagcgcaaaa ctttgtctca aaaaaaaaa aaaaaaaag tccgcagtat      6240 ggttttcaca ttatcactct caatgccatt ggaggtaggt ccaagctggt gtctctttga    6300
ttagtctccc taaacccatc tattcattta ctagccatta gttattcttt aattgagtcc    6360
aaaaatgttt gtgaggagat agtcccatat gagattaaaa gaaagaaaga aaacaaaaca    6420
acaaacaaac aaacaaaaca gaaaatcagg tgtagtggac actgaagagt ttctgctgta    6480
acttgtttgt ggtactacgg gattttggtt cagcctagat ttaccagctc ctgacttggg    6540
gacctcggtc aggcattgaa ggactctgag cctcagtttt gtcttctgtg aaatgagggc    6600
```

-continued

| | |
|---|---|
| attggacatt atgaaatgtc acatttctgt gaaatgaggg cattggacat tagggggacat | 6660 |
| gctctgcagt cccctaagtc ctctagatgt actaaaacag gcactattca cagcccagat | 6720 |
| aggcatgaac atcaaggtgc ctgcacaggc ttgagggaga taacagtttc tgaccatgcc | 6780 |
| tctgtactcc caattccaaa tcatggagga caaagtacag ggaagatgta aaacacacac | 6840 |
| taggttagaa atcggactgt cattgataag ttagttggct tatttgatat ttctgaatct | 6900 |
| gcttcctctc atagacaatg ggactaataa tgtctgcact attcactcta caaaatagtt | 6960 |
| gtgaggatca actcgataat gcatgtaaat gtgttttgaa aactaacaag tatcatggaa | 7020 |
| attaaaaaga caaacaagaa gctatgactc cactctgcag aaggcattcc caaataacga | 7080 |
| gtgccaggaa gatgggtttc ccctttcttt tggtgcagca acaattagag tcttgggcac | 7140 |
| cagatgtaca caattggaat gacataccat ttgctgtgct gctgtcagca taggacattc | 7200 |
| tctccttgat tttcagcatc tacctgtgga tacgaaagag acggtctttt tcatgtacag | 7260 |
| ctaaagtccc agagatatct ggcacataca gcagaagtac ttgcttcagt aagctttaat | 7320 |
| gaattttaag gactctgttg cttggaagat tccttgaaaa taagatttac tattgatcgg | 7380 |
| aaaaaagtga ggaaagtgaa aaagtctttt gaagcttttt ggctgatcgt cccttctgaa | 7440 |
| gaaatacatg tttttattca tagcaggaaa aataaaacaa aacccaaact attcttttta | 7500 |
| taatatactc cttgctaaga actttgttag cttacttagg ttagggaggt gaagttactt | 7560 |
| ttaaaagaag ctttatgtcc ttgctcaaac aggtggagga aaatcacaat gtgttttgag | 7620 |
| agaaaggact ttgactctta gagagaaaat gtgcgcctct caggggggaag ccttggaagg | 7680 |
| gggaaaagtt gggtggtgag gaaacctcaa gaaaaataag gcccaccttt ctcctgatgc | 7740 |
| tcagaacatt ggcaaagcag ctagcaaggc attcaccccca tttggcctgt ggaaatcttc | 7800 |
| cagcaggttc tcaattaagg gagctgcctt tcctttcatt ctcttaactt ttgtgttcaa | 7860 |
| tgttaacaac ctgatgctat ctattatggt gccattatca cagaatgttg actgaactgg | 7920 |
| ttcttttatc tccattatgg ggctgccttc cttgcagatt tatgcatttt tgatattaaa | 7980 |
| ttctttatct cattaagcct acactcttgt tgactttcat tgaccctctg ccctggtccc | 8040 |
| caatactttt ccatatttaa tattgaaaga ttttctcaa tgcccctctt ggctttgttg | 8100 |
| ccatccgttt gacggctgtc cctaatggcc tgtgctgttt gctctgttct tgaacttggt | 8160 |
| ggggtcacac atttttaaac agtgatgtcc tctgaatgtc caccccttgct gtccagctaa | 8220 |
| gttgccctgt gtcacaagct ctgccctctt ctccgcccct aactaccaac tgctcctaat | 8280 |
| tgcttcaaca aacaccttcc ctagtggtgc cctaggcccc ctgagccttt tgggttttgt | 8340 |
| ttagctgcta atgttctgcc tggcccaccg gcggattggc cttgctgacc tgatacatcg | 8400 |
| cagctcttct ccttggagcg cctgtcttgt ccagcgcccc ctgggccaaa ggccagggtc | 8460 |
| tgggcaggat tgaccagctg cttgaggtgg ccacaaaaga caacttcagc ttgaaacggg | 8520 |
| caaatgaatg tattcatttg tctttctttc cccttaaacc tatccacaaa ctcaatctac | 8580 |
| tgcctggctt gaaacaaaac aaagggatga tcttgagaag gggggcagga gaggcccctc | 8640 |
| tcgcaccaga aatcttagct cccttcttgg gggccgtctg ttcagtttca caacacttac | 8700 |
| aagaccaatt tccagaattg aagttgcctg gtgttttgat tcttcctttg cctgtgcatt | 8760 |
| tgtgccctga aggtcccttc caaatggata ctaattgtgg gggctgcacg ctgctggctg | 8820 |
| ctccaatgcc ccagggcccg aggacctgct tctcaaagcc ttaattgaca aggacctgtc | 8880 |
| tgtatttagg agcagctggt ccagagcgtt ggcacatcag tgcaatctta acgcagcatc | 8940 |
| cctagcctgg aggaggatga gggtaaatgt ggttaaaatg aaggaagatt tatagtcggc | 9000 |

-continued

```
ccccttgggt aataggacag aagacagctc ccaagatttt cccctacgag ggggttcatt      9060
catcagctcc tgggcctggt aaccggggag gaagagcgtt taagctatta ttactaatgg      9120
gggaggggca gaggcccgct tagaacaatt aggcaggtga caatattcca ctataatgcg      9180
tcgtcctcga aactggaccg ggtttagaag actatcaggg ctgtctcttg cttccgcggg      9240
cctcggcgcc ggggcctccg cctgggtctg gctccgggtt aatggtggcg ccgccgggag      9300
gctgggaagg gagaggggag ggcactctgg ctgccctgcc caggaacagg gaggctttca      9360
gtggccgctc ggactcctcg ttagggcgtt tgaaagcccc aaatggccgg tggcgggggc      9420
cattgcgtcg atcagttttt ccttcctgcg ccccatcagg cgcgcccggt tccccaacta      9480
cccgctcctc caccctgcga acgcctttcc gcaacctact ggctccgtag atacagccat      9540
tcagccggtt acaaaaaagg tttgttggtt caagaggaac ccggttttgt tgcgatgtgt      9600
gggaaatact ttgatgtcct cccagttcgc acgtgtgaac agggataatg ggtttgggga      9660
tcttcattga aatttgaagt ttttaaagca gaaattccct aacttttgcc tgttttctc      9720 aacatttct ttttctttt tttattcct tcaggaacaa tgccaacatt gaagtcctcg      9780
gttggagtct gcacagttgg agatctttgg tgccatttta gacatctttg gatttcatca      9840
atcaaactga ctgcaatttt ccataaaaac cctgaatttg ggtcagaaag tgggcaaagt      9900
agataaagat cattcgagct gtcttataag atgataaata gatatccttt caggccaaca      9960
atgccaaagt gcagttttgt gattcccttc catgggttct gaatgcagtg agtcgaaacg     10020
atttctacat gtttttcccat ggtttaggag gtgtctttac atacttgtca atagtagcct     10080
gacctttttc cccatggagt tgctaagtgt gttttgtttg ttgctttgag tacttttttc     10140
ttgttgtttg tgtgtgtgtt gcacaaaata cacaagaaaa taaaggtttt ttttctttta     10200
ttgctcaaat caataggata tgggtctgat ctagataatt ctctgcatat agactggttt     10260
cagtagccct tgagttcatg tagaaattcc atttgctctg cagttgctct tgaggcactt     10320
tggacaccat tttgggcacc atgctgggat gtaaactcac tttcttaaca acaacaacaa     10380
caacaacaac                                                            10390
```

<210> SEQ ID NO 20
<211> LENGTH: 855
<212> TYPE: DNA
<213> ORGANISM: Homo sapiens

<400> SEQUENCE: 20

```
atggactact cctacctcaa ttcgtacgac tcgtgcgtgg cggccatgga ggcgtccgcc       60
tacggcgact ttggcgcctg cagccagccc ggcggcttcc aatacagccc cctgcggccc      120
gctttccccg cggcagggcc gccctgcccc gcgctcggct cctccaactg cgcacttggc      180
gccctacgcg accaccagcc cgcgccctac tcggcagtgc cctacaagtt cttcccagag      240
ccatccggcc tgcacgagaa cgcaagcag cggcgcatcc gcaccacgtt caccagcgcg      300
cagctcaagg agctggagcg cgttttcgct gagacccact accccgacat ttacacgcgt      360
gaggagctgg cgctcaagat cgacctcact gaggctcgcg tgcaggtctg gttccagaac      420
cgccgggcca agttccgcaa acaggagcgc ggccagcg ccaagggcgc ggcgggcgcg      480
gcgggcgcca aaaagggcga ggcgcgctgc tcctccgagg acgacgattc caaggagtcc      540
acgtgcagcc ccacgcccga tagcaccgcc tcgctgccgc cgccgcctgc ccggcctg      600 gccagcccgc gcctgagccc cagcccgctg cccgtcgcac tgggctccgg gccgggacct      660
```

```
gggccggggc cacagccgct caagggcgca ctgtgggccg gtgtggcggg cggtgggggc    720
ggcgggcctg gcgcgggagc ggccgaacta cttaaggctt ggcagccggc ggagtccggc    780
cccgggccct tctccggggt tctgtcctcc tttcaccgga agcccggccc cgccctgaag    840
accaatctct tctag                                                     855
```

<210> SEQ ID NO 21
<211> LENGTH: 284
<212> TYPE: PRT
<213> ORGANISM: Homo sapiens

<400> SEQUENCE: 21

```
Met Asp Tyr Ser Tyr Leu Asn Ser Tyr Asp Ser Cys Val Ala Ala Met
1               5                   10                  15

Glu Ala Ser Ala Tyr Gly Asp Phe Gly Ala Cys Ser Gln Pro Gly Gly
            20                  25                  30

Phe Gln Tyr Ser Pro Leu Arg Pro Ala Phe Pro Ala Ala Gly Pro Pro
        35                  40                  45

Cys Pro Ala Leu Gly Ser Ser Asn Cys Ala Leu Gly Ala Leu Arg Asp
    50                  55                  60

His Gln Pro Ala Pro Tyr Ser Ala Val Pro Tyr Lys Phe Phe Pro Glu
65                  70                  75                  80

Pro Ser Gly Leu His Glu Lys Arg Lys Gln Arg Arg Ile Arg Thr Thr
                85                  90                  95

Phe Thr Ser Ala Gln Leu Lys Glu Leu Glu Arg Val Phe Ala Glu Thr
            100                 105                 110

His Tyr Pro Asp Ile Tyr Thr Arg Glu Glu Leu Ala Leu Lys Ile Asp
        115                 120                 125

Leu Thr Glu Ala Arg Val Gln Val Trp Phe Gln Asn Arg Arg Ala Lys
    130                 135                 140

Phe Arg Lys Gln Glu Arg Ala Ala Ser Ala Lys Gly Ala Ala Gly Ala
145                 150                 155                 160

Ala Gly Ala Lys Lys Gly Glu Ala Arg Cys Ser Ser Glu Asp Asp Asp
                165                 170                 175

Ser Lys Glu Ser Thr Cys Ser Pro Thr Pro Asp Ser Thr Ala Ser Leu
            180                 185                 190

Pro Pro Pro Pro Ala Pro Gly Leu Ala Ser Pro Arg Leu Ser Pro Ser
        195                 200                 205

Pro Leu Pro Val Ala Leu Gly Ser Gly Pro Gly Pro Gly Pro Gly Pro
    210                 215                 220

Gln Pro Leu Lys Gly Ala Leu Trp Ala Gly Val Ala Gly Gly Gly Gly
225                 230                 235                 240

Gly Gly Pro Gly Ala Gly Ala Ala Glu Leu Leu Lys Ala Trp Gln Pro
                245                 250                 255

Ala Glu Ser Gly Pro Gly Pro Phe Ser Gly Val Leu Ser Ser Phe His
            260                 265                 270

Arg Lys Pro Gly Pro Ala Leu Lys Thr Asn Leu Phe
        275                 280
```

<210> SEQ ID NO 22
<211> LENGTH: 945
<212> TYPE: DNA
<213> ORGANISM: Homo sapiens

<400> SEQUENCE: 22

```
atgtatataaaa tggaatattc ttacctcaat tcctctgcct acgagtcctg tatggctggg    60
```

```
atggacacct cgagcctggc ttcagcctat gctgacttca gttcctgcag ccaggccagt    120
ggcttccagt ataacccgat aaggaccact tttggggcca cgtccggctg cccttccctc    180
acgccgggat cctgcagcct gggcaccctc aggaccacc agagcagtcc gtacgccgca     240
gttccttaca aactcttcac ggaccacggc ggcctcaacg agaagcgcaa gcagcggcgc    300
atccgcacca ctttcaccag tgcccagctc aaagagctgg aaagggtctt cgcggagact    360
cactaccccg acatctacac tcgggaggag ctggccctga agatcgacct cacagaggcg    420
cgagtccagg tgtggttcca gaaccgccgc gccaagtttc gcaagcagga gcgcgcagcg    480
gcagccgcag cggccgcggc caagaacggc tcctcgggca aaaagtctga ctcttccagg    540
gacgacgaga gcaaagaggc caagagcact gacccggaca gcactggggg cccaggtccc    600
aatcccaacc ccaccccag ctgcggggcg aatggaggcg gcggcggcgg gcccagcccg     660
gctggagctc cggggggcggc ggggcccggg ggcccgggag cgaacccgg caagggcggc     720 gcagcagcag cggcggcggc cgcggcagcg gcggcggcgg cagcggcagc ggcggcagct    780
ggaggcctgg ctgcggctgg gggccctgga caaggctggg ctcccggccc cggccccatc    840
acctccatcc cggattcgct tgggggtccc ttcgccagcg tcctatcttc gctccaaaga    900
cccaacggtg ccaaagccgc cttagtgaag agcagtatgt tctga                    945
```

<210> SEQ ID NO 23
<211> LENGTH: 314
<212> TYPE: PRT
<213> ORGANISM: Homo sapiens

<400> SEQUENCE: 23

```
Met Tyr Lys Met Glu Tyr Ser Tyr Leu Asn Ser Ser Ala Tyr Glu Ser
1               5                   10                  15

Cys Met Ala Gly Met Asp Thr Ser Ser Leu Ala Ser Ala Tyr Ala Asp
                20                  25                  30

Phe Ser Ser Cys Ser Gln Ala Ser Gly Phe Gln Tyr Asn Pro Ile Arg
            35                  40                  45

Thr Thr Phe Gly Ala Thr Ser Gly Cys Pro Ser Leu Thr Pro Gly Ser
        50                  55                  60

Cys Ser Leu Gly Thr Leu Arg Asp His Gln Ser Ser Pro Tyr Ala Ala
65                  70                  75                  80

Val Pro Tyr Lys Leu Phe Thr Asp His Gly Gly Leu Asn Glu Lys Arg
                85                  90                  95

Lys Gln Arg Arg Ile Arg Thr Thr Phe Thr Ser Ala Gln Leu Lys Glu
                100                 105                 110

Leu Glu Arg Val Phe Ala Glu Thr His Tyr Pro Asp Ile Tyr Thr Arg
            115                 120                 125

Glu Glu Leu Ala Leu Lys Ile Asp Leu Thr Glu Ala Arg Val Gln Val
        130                 135                 140

Trp Phe Gln Asn Arg Arg Ala Lys Phe Arg Lys Gln Glu Arg Ala Ala
145                 150                 155                 160

Ala Ala Ala Ala Ala Ala Lys Asn Gly Ser Ser Gly Lys Lys Ser
                165                 170                 175

Asp Ser Ser Arg Asp Asp Glu Ser Lys Glu Ala Lys Ser Thr Asp Pro
                180                 185                 190

Asp Ser Thr Gly Gly Pro Gly Pro Asn Pro Asn Pro Thr Pro Ser Cys
            195                 200                 205

Gly Ala Asn Gly Gly Gly Gly Gly Gly Pro Ser Pro Ala Gly Ala Pro
```

```
                210                 215                 220
Gly Ala Ala Gly Pro Gly Gly Pro Gly Gly Glu Pro Gly Lys Gly Gly
225                 230                 235                 240

Ala Ala Ala Ala Ala Ala Ala Ala Ala Ala Ala Ala Ala Ala Ala Ala
                245                 250                 255

Ala Ala Ala Ala Gly Gly Leu Ala Ala Ala Gly Gly Pro Gly Gln Gly
                260                 265                 270

Trp Ala Pro Gly Pro Gly Pro Ile Thr Ser Ile Pro Asp Ser Leu Gly
            275                 280                 285

Gly Pro Phe Ala Ser Val Leu Ser Ser Leu Gln Arg Pro Asn Gly Ala
        290                 295                 300

Lys Ala Ala Leu Val Lys Ser Ser Met Phe
305                 310
```

<210> SEQ ID NO 24
<211> LENGTH: 907
<212> TYPE: DNA
<213> ORGANISM: Homo sapiens

<400> SEQUENCE: 24

```
ttttcaaatg caatcaaggc ttcctatata cgggcggaaa ggcggcttcc tccgctgaga    60
aagctgaagg tccttacctg cggcgtacgg actgctctgg tggtccctga gggtgcccag   120
gctgcaggat cccggcgtga gggaagggca gccggacgtg gccccaaaag tggtccttat   180
cgggttatac tggaagccac tggcctggct gcaggaactg aagtcagcat aggctgaagc   240
caggctcgag gtgtccatcc agccatacag gactcgtag gcagaggaat tgagggttct   300
cacaaccaat tgaaagagaa taaaacattc tcttgcttca taaccaaagt gctgctcaca   360
cttacagcaa ccttttggaag gggaatcctg gctattgatg tccctggaaa gagagtggta   420
gaagaaaaga aattgaagac atggaagaaa gatgaaaacg ctggctacta aatacctatg   480
tgtggttact gagtgtggta tacttggaca ccgagctccc ccacccatca gatgtcacaa   540
agagtcctct tactcttgga taatttcaaa tcaaactgac ctccccagat attgagaagc   600
aaaataatca acaacaacaa aacctgcctt gtaaatatga tttacattga ttatgtgggg   660
atgttctgaa gggagaagaa aggagctgtc accaactcaa agcaacatga gagcaagaat   720
catgctaatt ttgccgtctg cctctcctat gttcttggtg ccaagtctgt agttgaggtt   780
catttacctg aatgagtgac taaagcttta aacttgaac actttgaata catagatcta   840
gcataaataa gcctattaat ggcaactttg acctgtcaag caataaccaa atgatttgtg   900
tgcctgc                                                            907
```

<210> SEQ ID NO 25
<211> LENGTH: 2184
<212> TYPE: DNA
<213> ORGANISM: Homo sapiens

<400> SEQUENCE: 25

```
atggaaggtg atgcagtcga agccattgtg gaggagtccg aaacttttat taaggaaag    60
gagagaaaga cttaccagag acgccgggaa ggggccagg aagaagatgc ctgccactta   120
ccccagaacc agacggatgg gggtgaggtg gtccaggatg tcaacagcag tgtacagatg   180
gtgatgatgg aacagctgga ccccaccctt cttcagatga agactgaagt aatggagggc   240
acagtggctc cagaagcaga ggctgctgtg acgataccc agattataac tttcagggtt   300
gtaaatatgg aggaacagcc cataaacata ggagaacttc agcttgttca agtacctgtt   360
```

-continued

```
cctgtgactg tacctgttgc taccacttca gtagaagaac ttcagggggc ttatgaaaat    420
gaagtgtcta aagagggcct tgcggaaagt gaacccatga tatgccacac cctacctttg    480
cctgaagggt ttcaggtggt taaagtgggg gccaatggag aggtggagac actagaacaa    540
ggggaacttc cacccagga agatcctagt tggcaaaaag acccagacta tcagccacca    600
gccaaaaaaa caagaaaac caaaagagc aaactgcgtt atacagagga gggcaaagat    660
gtagatgtgt ctgtctacga ttttgaggaa aacagcagg agggtctgct atcagaggtt    720
aatgcagaga aagtggttgg taatatgaag cctccaaagc caacaaaaat taaaaagaaa    780
ggtgtaaaga agacattcca gtgtgagctt gcagttaca cgtgtccacg gcgttcaaat    840
ttggatcgtc acatgaaaag ccacactgat gagagaccac acaagtgcca tctctgtggc    900
agggcattca gaacagtcac cctcctgagg aatcaccta acacacacac aggtactcgt    960
cctcacaagt gcccagactg cgacatggcc tttgtgacca gtggagaatt ggttcggcat   1020
cgtcgttaca acacaccca cgagaagcca ttcaagtgtt ccatgtgcga ttacgccagt   1080
gtagaagtca gcaaattaaa acgtcacatt cgctctcata ctggagagcg tccgtttcag   1140
tgcagtttgt gcagttatgc cagcagggac acatacaagc tgaaaaggca catgagaacc   1200
cattcagggg aaaagcctta tgaatgttat atttgtcatg ctcggtttac ccaaagtggt   1260
accatgaaga tgcacatttt acagaagcac acagaaaatg tggccaaatt tcactgtccc   1320
cactgtgaca cagtcatagc ccgaaaaagt gatttgggtg tccacttgcg aaagcagcat   1380
tcctatattg agcaaggcaa gaaatgccgt tactgtgatg ctgtgtttca tgagcgctat   1440
gccctcatcc agcatcagaa gtcacacaag aatgagaagc gctttaagtg tgaccagtgt   1500
gattacgctt gtagacagga gaggcacatg atcatgcaca gcgcacccca caccggggag   1560
aagccttacg cctgcagcca ctgcgataag accttccgcc agaagcagct tctcgacatg   1620
cacttcaagc gctatcacga ccccaacttc gtccctgcgg cttttgtctg ttctaagtgt   1680
gggaaaacat ttacacgtcg gaataccatg gcaagacatg ctgataattg tgctggccca   1740
gatggcgtag aggggaaaa tggaggagaa acgaagaaga gtaaacgtgg aagaaaaaga   1800
aagatgcgct ctaagaaaga agattcctct gacagtgaaa atgctgaacc agatctggac   1860
gacaatgagg atgaggagga gcctgccgta gaaattgaac ctgagccaga gcctcagcct   1920
gtgaccccag ccccaccacc cgccaagaag cggagaggac gaccccctgg cagaaccaac   1980
cagcccaaac agaaccagcc aacagctatc attcaggttg aagaccagaa tacaggtgca   2040
attgagaaca ttatagttga agtaaaaaaa gagccagatg ctgagcccgc agagggagag   2100
gaagaggagg cccagccagc tgccacagat gcccccaacg agacctcac gcccgagatg   2160
atcctcagca tgatggaccg gtga                                          2184
```

<210> SEQ ID NO 26
<211> LENGTH: 727
<212> TYPE: PRT
<213> ORGANISM: Homo sapiens

<400> SEQUENCE: 26

Met Glu Gly Asp Ala Val Glu Ala Ile Val Glu Glu Ser Glu Thr Phe
1               5                   10                  15

Ile Lys Gly Lys Glu Arg Lys Thr Tyr Gln Arg Arg Arg Glu Gly Gly
            20                  25                  30

Gln Glu Glu Asp Ala Cys His Leu Pro Gln Asn Gln Thr Asp Gly Gly
        35                  40                  45

-continued

```
Glu Val Val Gln Asp Val Asn Ser Ser Val Gln Met Val Met Met Glu
     50                  55                  60

Gln Leu Asp Pro Thr Leu Leu Gln Met Lys Thr Glu Val Met Glu Gly
 65                  70                  75                  80

Thr Val Ala Pro Glu Ala Glu Ala Val Asp Asp Thr Gln Ile Ile
                 85                  90                  95

Thr Leu Gln Val Val Asn Met Glu Glu Gln Pro Ile Asn Ile Gly Glu
                100                 105                 110

Leu Gln Leu Val Gln Val Pro Val Pro Val Thr Val Pro Val Ala Thr
            115                 120                 125

Thr Ser Val Glu Glu Leu Gln Gly Ala Tyr Glu Asn Glu Val Ser Lys
        130                 135                 140

Glu Gly Leu Ala Glu Ser Glu Pro Met Ile Cys His Thr Leu Pro Leu
145                 150                 155                 160

Pro Glu Gly Phe Gln Val Val Lys Val Gly Ala Asn Gly Glu Val Glu
                165                 170                 175

Thr Leu Glu Gln Gly Glu Leu Pro Pro Gln Glu Asp Pro Ser Trp Gln
                180                 185                 190

Lys Asp Pro Asp Tyr Gln Pro Pro Ala Lys Lys Thr Lys Lys Thr Lys
            195                 200                 205

Lys Ser Lys Leu Arg Tyr Thr Glu Glu Gly Lys Asp Val Asp Val Ser
        210                 215                 220

Val Tyr Asp Phe Glu Glu Glu Gln Gln Glu Gly Leu Leu Ser Glu Val
225                 230                 235                 240

Asn Ala Glu Lys Val Val Gly Asn Met Lys Pro Pro Lys Pro Thr Lys
                245                 250                 255

Ile Lys Lys Lys Gly Val Lys Lys Thr Phe Gln Cys Glu Leu Cys Ser
            260                 265                 270

Tyr Thr Cys Pro Arg Arg Ser Asn Leu Asp Arg His Met Lys Ser His
        275                 280                 285

Thr Asp Glu Arg Pro His Lys Cys His Leu Cys Gly Arg Ala Phe Arg
    290                 295                 300

Thr Val Thr Leu Leu Arg Asn His Leu Asn Thr His Thr Gly Thr Arg
305                 310                 315                 320

Pro His Lys Cys Pro Asp Cys Asp Met Ala Phe Val Thr Ser Gly Glu
                325                 330                 335

Leu Val Arg His Arg Arg Tyr Lys His Thr His Glu Lys Pro Phe Lys
            340                 345                 350

Cys Ser Met Cys Asp Tyr Ala Ser Val Glu Val Ser Lys Leu Lys Arg
        355                 360                 365

His Ile Arg Ser His Thr Gly Glu Arg Pro Phe Gln Cys Ser Leu Cys
    370                 375                 380

Ser Tyr Ala Ser Arg Asp Thr Tyr Lys Leu Lys Arg His Met Arg Thr
385                 390                 395                 400

His Ser Gly Glu Lys Pro Tyr Glu Cys Tyr Ile Cys His Ala Arg Phe
                405                 410                 415

Thr Gln Ser Gly Thr Met Lys Met His Ile Leu Gln Lys His Thr Glu
            420                 425                 430

Asn Val Ala Lys Phe His Cys Pro His Cys Asp Thr Val Ile Ala Arg
        435                 440                 445

Lys Ser Asp Leu Gly Val His Leu Arg Lys Gln His Ser Tyr Ile Glu
    450                 455                 460
```

| | | | | | | | | | | | |
|---|---|---|---|---|---|---|---|---|---|---|---|
| Gln | Gly | Lys | Lys | Cys | Arg | Tyr | Cys | Asp | Ala | Val | Phe | His | Glu | Arg | Tyr |
| 465 | | | | 470 | | | | 475 | | | | | | | 480 |

Gln Gly Lys Lys Cys Arg Tyr Cys Asp Ala Val Phe His Glu Arg Tyr
465                 470                 475                 480

Ala Leu Ile Gln His Gln Lys Ser His Lys Asn Glu Lys Arg Phe Lys
                485                 490                 495

Cys Asp Gln Cys Asp Tyr Ala Cys Arg Gln Glu Arg His Met Ile Met
            500                 505                 510

His Lys Arg Thr His Thr Gly Glu Lys Pro Tyr Ala Cys Ser His Cys
        515                 520                 525

Asp Lys Thr Phe Arg Gln Lys Gln Leu Leu Asp Met His Phe Lys Arg
530                 535                 540

Tyr His Asp Pro Asn Phe Val Pro Ala Ala Phe Val Cys Ser Lys Cys
545                 550                 555                 560

Gly Lys Thr Phe Thr Arg Arg Asn Thr Met Ala Arg His Ala Asp Asn
                565                 570                 575

Cys Ala Gly Pro Asp Gly Val Glu Gly Glu Asn Gly Gly Glu Thr Lys
            580                 585                 590

Lys Ser Lys Arg Gly Arg Lys Arg Lys Met Arg Ser Lys Lys Glu Asp
        595                 600                 605

Ser Ser Asp Ser Glu Asn Ala Glu Pro Asp Leu Asp Asp Asn Glu Asp
610                 615                 620

Glu Glu Glu Pro Ala Val Glu Ile Glu Pro Glu Pro Glu Pro Gln Pro
625                 630                 635                 640

Val Thr Pro Ala Pro Pro Ala Lys Lys Arg Arg Gly Arg Pro Pro
                645                 650                 655

Gly Arg Thr Asn Gln Pro Lys Gln Asn Gln Pro Thr Ala Ile Ile Gln
            660                 665                 670

Val Glu Asp Gln Asn Thr Gly Ala Ile Glu Asn Ile Ile Val Glu Val
        675                 680                 685

Lys Lys Glu Pro Asp Ala Glu Pro Ala Glu Gly Glu Glu Glu Glu Ala
690                 695                 700

Gln Pro Ala Ala Thr Asp Ala Pro Asn Gly Asp Leu Thr Pro Glu Met
705                 710                 715                 720

Ile Leu Ser Met Met Asp Arg
                725

<210> SEQ ID NO 27
<211> LENGTH: 1896
<212> TYPE: DNA
<213> ORGANISM: Homo sapiens

<400> SEQUENCE: 27

```
atgttctacg cacattttgt tctcagtaaa agagggcctc tggccaaaat ttggctagcg     60
gcccattggg ataagaagct aaccaaagcc catgtgttcg agtgtaattt agagagcagc    120
gtggagagta tcatctcacc aaaggtgaaa atggcattac ggacatcagg acatctctta    180
ctggagtag ttcgaatcta tcacaggaaa gccaaatacc ttcttgcaga ctgtaatgaa    240
gcattcatta agataaagat ggcttttcgg ccaggtgtgg ttgacctgcc tgaggaaaat    300
cgggaagcag cttataatgc cattacttta cctgaagaat tcatgactt tgatcagcca    360
ctgcctgact agatgacat cgatgtggcc cagcagttca gcttgaatca agtagagtg    420
gaagagataa ccatgagaga agaagttggg aacatcagta ttttacaaga aaatgatttt    480
ggtgattttg gaatggatga tcgtgagata atgagaaag gcagtgcttt tgaggatgac    540
gacatgttag taagcactac tacttctaac ctcctattag agtctgaaca gagcaccagc    600
```

-continued

```
aatctgaatg agaaaattaa ccatttagaa tatgaagatc aatataagga tgataatttt    660
ggagaaggaa atgatggtgg aatattagat gacaaactta ttagtaataa tgatggcggt    720
atctttgatg atccccctgc cctctctgag gcaggggtga tgttgccaga gcagcctgca    780
catgacgata tggatgagga tgataatgta tcaatgggtg ggcctgatag tcctgattca    840
gtggatcccg ttgaaccaat gccaaccatg actgatcaaa caacacttgt tccaaatgag    900
gaagaagcat ttgcattgga gcctattgat ataactgtta agaaacaaa agccaagagg    960
aagaggaagc taattgttga cagtgtcaaa gagttggata gcaagacaat tagagcccaa   1020
cttagtgatt attcagatat tgttactact ttggatctgg caccgcccac caagaaattg   1080
atgatgtgga aagagacagg aggagtagaa aaactgtttt ctttacctgc tcagcctttg   1140
tggaataaca gactactgaa gctctttaca cgctgtctta caccgcttgt accagaagac   1200
cttagaaaaa ggaggaaagg aggagaggca gataatttgg atgaattcct caaagaattt   1260
gaaaatccag aggttcctag agaggaccag caacagcagc atcagcagcg tgatgttatc   1320
gatgagccca ttattgaaga gccaagccgc ctccaggagt cagtgatgga ggccagcaga   1380
acaaacatag atgagtcagc tatgcctcca ccaccacctc agggagttaa gcgaaaagct   1440
ggacaaattg acccagagcc tgtgatgcct cctcagcagg tagagcagat ggaaatacca   1500
cctgtagagc ttcccccaga agaacctcca aatatctgtc agctaatacc agagttagaa   1560
cttctgccag aaaaagagaa ggagaaagag aaggaaaaag aagatgatga agaggaagag   1620
gatgaagatg catcagggggg cgatcaagat caggaagaaa aagatggaa caaaaggact   1680
cagcagatgc ttcatggtct tcagcgtgct cttgctaaaa ctggagctga atctatcagt   1740
ttgcttgagt tatgtcgaaa tacgaacaga aaacaagctg ccgcaaagtt ctacagcttc   1800
ttggttctta aaaagcagca agctattgag ctgacacagg aagaaccgta cagtgacatc   1860
atcgcaacac ctggaccaag gttccatatt atataa                             1896
```

<210> SEQ ID NO 28
<211> LENGTH: 631
<212> TYPE: PRT
<213> ORGANISM: Homo sapiens

<400> SEQUENCE: 28

```
Met Phe Tyr Ala His Phe Val Leu Ser Lys Arg Gly Pro Leu Ala Lys
1               5                   10                  15

Ile Trp Leu Ala Ala His Trp Asp Lys Lys Leu Thr Lys Ala His Val
            20                  25                  30

Phe Glu Cys Asn Leu Glu Ser Ser Val Glu Ser Ile Ile Ser Pro Lys
        35                  40                  45

Val Lys Met Ala Leu Arg Thr Ser Gly His Leu Leu Leu Gly Val Val
    50                  55                  60

Arg Ile Tyr His Arg Lys Ala Lys Tyr Leu Leu Ala Asp Cys Asn Glu
65                  70                  75                  80

Ala Phe Ile Lys Ile Lys Met Ala Phe Arg Pro Gly Val Val Asp Leu
                85                  90                  95

Pro Glu Glu Asn Arg Glu Ala Ala Tyr Asn Ala Ile Thr Leu Pro Glu
            100                 105                 110

Glu Phe His Asp Phe Asp Gln Pro Leu Pro Asp Leu Asp Asp Ile Asp
        115                 120                 125

Val Ala Gln Gln Phe Ser Leu Asn Gln Ser Arg Val Glu Glu Ile Thr
    130                 135                 140
```

```
Met Arg Glu Glu Val Gly Asn Ile Ser Ile Leu Gln Glu Asn Asp Phe
145                 150                 155                 160

Gly Asp Phe Gly Met Asp Arg Glu Ile Met Arg Glu Gly Ser Ala
            165                 170                 175

Phe Glu Asp Asp Asp Met Leu Val Ser Thr Thr Thr Ser Asn Leu Leu
            180                 185                 190

Leu Glu Ser Glu Gln Ser Thr Ser Asn Leu Asn Glu Lys Ile Asn His
            195                 200                 205

Leu Glu Tyr Glu Asp Gln Tyr Lys Asp Asp Asn Phe Gly Glu Gly Asn
            210                 215                 220

Asp Gly Gly Ile Leu Asp Asp Lys Leu Ile Ser Asn Asn Asp Gly Gly
225                 230                 235                 240

Ile Phe Asp Asp Pro Pro Ala Leu Ser Glu Ala Gly Val Met Leu Pro
                245                 250                 255

Glu Gln Pro Ala His Asp Asp Met Asp Glu Asp Asp Asn Val Ser Met
                260                 265                 270

Gly Gly Pro Asp Ser Pro Asp Ser Val Asp Pro Val Glu Pro Met Pro
            275                 280                 285

Thr Met Thr Asp Gln Thr Thr Leu Val Pro Asn Glu Glu Glu Ala Phe
290                 295                 300

Ala Leu Glu Pro Ile Asp Ile Thr Val Lys Glu Thr Lys Ala Lys Arg
305                 310                 315                 320

Lys Arg Lys Leu Ile Val Asp Ser Val Lys Glu Leu Asp Ser Lys Thr
                325                 330                 335

Ile Arg Ala Gln Leu Ser Asp Tyr Ser Asp Ile Val Thr Thr Leu Asp
            340                 345                 350

Leu Ala Pro Pro Thr Lys Lys Leu Met Met Trp Lys Glu Thr Gly Gly
            355                 360                 365

Val Glu Lys Leu Phe Ser Leu Pro Ala Gln Pro Leu Trp Asn Asn Arg
370                 375                 380

Leu Leu Lys Leu Phe Thr Arg Cys Leu Thr Pro Leu Val Pro Glu Asp
385                 390                 395                 400

Leu Arg Lys Arg Lys Gly Gly Glu Ala Asp Asn Leu Asp Glu Phe
            405                 410                 415

Leu Lys Glu Phe Glu Asn Pro Glu Val Pro Arg Glu Asp Gln Gln Gln
            420                 425                 430

Gln His Gln Gln Arg Asp Val Ile Asp Glu Pro Ile Glu Glu Pro
            435                 440                 445

Ser Arg Leu Gln Glu Ser Val Met Glu Ala Ser Arg Thr Asn Ile Asp
450                 455                 460

Glu Ser Ala Met Pro Pro Pro Gln Gly Val Lys Arg Lys Ala
465                 470                 475                 480

Gly Gln Ile Asp Pro Glu Pro Val Met Pro Gln Gln Val Glu Gln
            485                 490                 495

Met Glu Ile Pro Pro Val Glu Leu Pro Pro Glu Glu Pro Asn Ile
            500                 505                 510

Cys Gln Leu Ile Pro Glu Leu Glu Leu Leu Pro Glu Lys Glu Lys Glu
            515                 520                 525

Lys Glu Lys Glu Lys Glu Asp Glu Glu Glu Glu Asp Glu Asp Ala
            530                 535                 540

Ser Gly Gly Asp Gln Asp Gln Glu Glu Arg Arg Trp Asn Lys Arg Thr
545                 550                 555                 560

Gln Gln Met Leu His Gly Leu Gln Arg Ala Leu Ala Lys Thr Gly Ala
```

565                 570                 575
Glu Ser Ile Ser Leu Leu Glu Leu Cys Arg Asn Thr Asn Arg Lys Gln
            580                 585                 590

Ala Ala Ala Lys Phe Tyr Ser Phe Leu Val Leu Lys Lys Gln Gln Ala
        595                 600                 605

Ile Glu Leu Thr Gln Glu Glu Pro Tyr Ser Asp Ile Ile Ala Thr Pro
    610                 615                 620

Gly Pro Arg Phe His Ile Ile
625                 630

<210> SEQ ID NO 29
<211> LENGTH: 3654
<212> TYPE: DNA
<213> ORGANISM: Homo sapiens

<400> SEQUENCE: 29

| | | | | |
|---|---|---|---|---|
| atgtacataa | agcaggtgat | tatccagggt | tttcgaagtt | acagagatca | aacaattgta | 60 |
| gatcccttca | gttcaaaaca | taatgtgatt | gtgggcagaa | atggatctgg | aaaaagtaac | 120 |
| ttttttatg | caattcagtt | tgttctcagt | gatgagttta | gtcatcttcg | tccagaacag | 180 |
| cggttggctt | tattgcatga | aggtactggt | cctcgtgtta | tttctgcttt | tgtggagatt | 240 |
| atttttgata | attcagacaa | ccggttacca | atcgataaag | aggaagtttc | acttcgaaga | 300 |
| gttattggtg | ccaaaaagga | tcagtatttc | ttagacaaga | gatggtcac | gaaaaatgat | 360 |
| gtgatgaacc | tccttgaaag | cgctggtttt | tctcgaagca | atccttatta | tattgttaaa | 420 |
| caaggaaaga | tcaaccagat | ggcaacagca | ccagattctc | agagattaaa | gctattaaga | 480 |
| gaagtagctg | gtactagagt | gtatgacgaa | cgaaaggaag | aaagcatctc | cttaatgaaa | 540 |
| gaaacagagg | gcaaacggga | aaaaatcaat | gagttgttaa | atacattga | agagagatta | 600 |
| catactctag | aggaagaaaa | ggaagaacta | gctcagtatc | agaagtggga | taaaatgaga | 660 |
| cgagccctgg | aatataccat | ttacaatcag | gaacttaacg | agactcgtgc | caaacttgat | 720 |
| gagctttctg | ctaagcgaga | gactagtgga | gaaaaatcca | gacaattaag | agatgctcag | 780 |
| caggatgcaa | gagataaaat | ggaggatatc | gaacgccaag | ttagagaatt | gaaaacaaaa | 840 |
| atttcagcta | tgaaagaaga | aaaagaacag | cttagtgctg | aaagacaaga | gcagattaag | 900 |
| cagaggacta | agttggagct | aaagccaag | gatttacaag | atgaactagc | aggcaatagt | 960 |
| gaacaaagga | aacgtttatt | aaaagagagg | cagaagctgc | ttgaaaaaat | agaagaaaag | 1020 |
| cagaaagaac | tggcagaaac | agaacccaaa | ttcaacagtg | tgaaagagaa | agaagaacga | 1080 |
| ggaattgcta | gattggctca | agctacccag | gaaagaacgg | atctttatgc | aaagcagggt | 1140 |
| cgaggaagcc | agtttacatc | aaaagaagaa | agggataagt | ggattaaaaa | ggaactcaag | 1200 |
| tctttagatc | aggctattaa | tgacaagaaa | agacagattg | ctgctataca | taaggatttg | 1260 |
| gaagacactg | aagcaaataa | agagaaaat | ctggagcagt | ataataaact | ggaccaggat | 1320 |
| cttaatgaag | tcaaagctcg | agtagaagaa | ctggacagaa | atattacga | agtaaaaaat | 1380 |
| aagaaagatg | aactacaaag | tgaaagaaac | tacttgtgga | gagaagagaa | tgcagaacag | 1440 |
| caagcacttg | ctgctaaaag | agaagatctt | gaaagaagc | aacaacttct | tagagcagca | 1500 |
| acaggaaagg | ccatttaaa | tggaatagac | agcataaaca | aagtgctaga | ccacttccgt | 1560 |
| cgaaaaggaa | taaccagca | tgttcaaaat | ggctatcatg | gtattgtaat | gaataacttt | 1620 |
| gaatgtgaac | cagcttccta | cacatgcgtg | gaagtcactg | ctggaaacag | gttatttat | 1680 |
| cacattgttg | attcagatga | agtcagcacg | aagatttaa | tggagtttaa | taaaatgaat | 1740 |

```
cttcctggag aggttacttt tctgcctctt aacaagttag atgtcaggga tacagcctat    1800
cctgaaacca atgatgctat tcctatgatc agcaaactga ggtacaatcc cagatttgac    1860
aaagctttca acatgtgtt tggaaagact cttatttgtc gtagcatgga agtttcaacc    1920
cagctggccc gtgcttttca tatggactgt attactttgg aaggtgacca agtcagccat    1980
cggggtgctc taactggggg ttattatgac acaaggaagt ctcgacttga attgcaaaaa    2040
gatgttagaa aagcagaaga gaactaggt gaacttgaag caaagctcaa tgaaaacctg     2100
cgcagaaata ttgaaaggat taataatgaa attgatcagt tgatgaacca aatgcaacag    2160
atcgagaccc agcaaggaa atttaaagca tctagagata gcatattatc agaaatgaag    2220
atgctaaaag agaagaggca gcagtcagag aaaaccttca tgcctaagca acgtagctta   2280
cagagtttgg aggcaagctt gcatgctatg gagtctacca gagagtcatt gaaagcagaa   2340
ctgggaactg atttgctttc tcaactgagt ttggaagatc agaagagagt agatgcactg   2400
aatgatgaga ttcgtcaact tcagcaggaa aacagacagt tgctaaatga agaattaaa    2460 ttagaaggta ttattactcg agtagagact tatctcaatg agaatctgag aaaacgcttg   2520
gaccaagtag aacaggaact taatgagctg agagagacag aagggggtac tgttctcaca   2580
gccacaacat cagaacttga agccatcaat aaaagagtaa agacactat ggcacgatca    2640 gaagatttgg acaattccat tgataaaaca gaagctggaa ttaaggagct tcagaagagt   2700
atggagcgct ggaaaaatat ggaaaagaa catatggatg ctataaatca tgatactaaa    2760
gaactggaaa agatgacaaa tcggcaaggc atgctattga agaagaaga agtgtatg     2820 aagaaaattc gagaacttgg atcacttccc caggaagcat ttgaaaagta ccagacactg   2880
agcctcaaac agttgtttcg aaaacttgag cagtgcaaca cagaattaaa gaagtacagc   2940
catgttaaca aaaaggcttt ggatcagttt gtaaatttct ccgagcagaa agaaaagtta   3000
ataaagcgtc aagaagagtt agatagggggt acaaatcaa tcatggaact gatgaatgta    3060
cttgaacttc ggaaatatga agctattcag ttaactttca acaggtatc taagaacttc    3120 agtgaagtat tccagaagtt agtacctggt ggcaaagcta cttggtgat gaagaaagga    3180 gatgtggagg gcagtcagtc tcaagatgaa ggagaaggga gtggtgagag tgagagggt    3240 tctggctcac aaagcagtgt cccatcagtt gaccagttta ctggagttgg aattagggtg   3300
tcatttacag gaaaacaagg tgaaatgaga gaaatgcaac agctttcagg tggacagaaa   3360
tccttggtag cccttgctct gattttgcc attcagaat gtgaccggc tccattttac      3420 ttgttgatg aaattgacca ggctctggat gctcagcaca gaaaggctgt gtcagatatg     3480
attatggaac ttgctgtaca tgctcagttt attacaacta cttttaggcc tgaactgctt   3540
gagtcagctg acaaattcta tggtgtaaag ttcagaaata aggttagtca tattgatgtg   3600
atcacagcag agatggccaa agactttgta gaagatgata ccacacatgg ttaa         3654
```

<210> SEQ ID NO 30
<211> LENGTH: 1217
<212> TYPE: PRT
<213> ORGANISM: Homo sapiens

<400> SEQUENCE: 30

Met Tyr Ile Lys Gln Val Ile Ile Gln Gly Phe Arg Ser Tyr Arg Asp
1               5                   10                  15

Gln Thr Ile Val Asp Pro Phe Ser Ser Lys His Asn Val Ile Val Gly
            20                  25                  30

-continued

```
Arg Asn Gly Ser Gly Lys Ser Asn Phe Phe Tyr Ala Ile Gln Phe Val
             35                  40                  45
Leu Ser Asp Glu Phe Ser His Leu Arg Pro Glu Gln Arg Leu Ala Leu
 50                  55                  60
Leu His Glu Gly Thr Gly Pro Arg Val Ile Ser Ala Phe Val Glu Ile
65                  70                  75                  80
Ile Phe Asp Asn Ser Asp Asn Arg Leu Pro Ile Asp Lys Glu Glu Val
                 85                  90                  95
Ser Leu Arg Arg Val Ile Gly Ala Lys Lys Asp Gln Tyr Phe Leu Asp
            100                 105                 110
Lys Lys Met Val Thr Lys Asn Asp Val Met Asn Leu Leu Glu Ser Ala
            115                 120                 125
Gly Phe Ser Arg Ser Asn Pro Tyr Tyr Ile Val Lys Gln Gly Lys Ile
            130                 135                 140
Asn Gln Met Ala Thr Ala Pro Asp Ser Gln Arg Leu Lys Leu Leu Arg
145                 150                 155                 160
Glu Val Ala Gly Thr Arg Val Tyr Asp Glu Arg Lys Glu Glu Ser Ile
                165                 170                 175
Ser Leu Met Lys Glu Thr Glu Gly Lys Arg Glu Lys Ile Asn Glu Leu
            180                 185                 190
Leu Lys Tyr Ile Glu Glu Arg Leu His Thr Leu Glu Glu Glu Lys Glu
            195                 200                 205
Glu Leu Ala Gln Tyr Gln Lys Trp Asp Lys Met Arg Arg Ala Leu Glu
            210                 215                 220
Tyr Thr Ile Tyr Asn Gln Glu Leu Asn Glu Thr Arg Ala Lys Leu Asp
225                 230                 235                 240
Glu Leu Ser Ala Lys Arg Glu Thr Ser Gly Glu Lys Ser Arg Gln Leu
                245                 250                 255
Arg Asp Ala Gln Gln Asp Ala Arg Asp Lys Met Glu Asp Ile Glu Arg
            260                 265                 270
Gln Val Arg Glu Leu Lys Thr Lys Ile Ser Ala Met Lys Glu Glu Lys
            275                 280                 285
Glu Gln Leu Ser Ala Glu Arg Gln Glu Gln Ile Lys Gln Arg Thr Lys
            290                 295                 300
Leu Glu Leu Lys Ala Lys Asp Leu Gln Asp Glu Leu Ala Gly Asn Ser
305                 310                 315                 320
Glu Gln Arg Lys Arg Leu Leu Lys Glu Arg Gln Lys Leu Leu Glu Lys
                325                 330                 335
Ile Glu Glu Lys Gln Lys Glu Leu Ala Glu Thr Glu Pro Lys Phe Asn
            340                 345                 350
Ser Val Lys Glu Lys Glu Glu Arg Gly Ile Ala Arg Leu Ala Gln Ala
            355                 360                 365
Thr Gln Glu Arg Thr Asp Leu Tyr Ala Lys Gln Gly Arg Gly Ser Gln
            370                 375                 380
Phe Thr Ser Lys Glu Glu Arg Asp Lys Trp Ile Lys Lys Glu Leu Lys
385                 390                 395                 400
Ser Leu Asp Gln Ala Ile Asn Asp Lys Lys Arg Gln Ile Ala Ala Ile
                405                 410                 415
His Lys Asp Leu Glu Asp Thr Glu Ala Asn Lys Glu Lys Asn Leu Glu
            420                 425                 430
Gln Tyr Asn Lys Leu Asp Gln Asp Leu Asn Glu Val Lys Ala Arg Val
            435                 440                 445
Glu Glu Leu Asp Arg Lys Tyr Tyr Glu Val Lys Asn Lys Lys Asp Glu
```

-continued

```
              450                 455                 460
Leu Gln Ser Glu Arg Asn Tyr Leu Trp Arg Glu Glu Asn Ala Glu Gln
465                 470                 475                 480

Gln Ala Leu Ala Ala Lys Arg Glu Asp Leu Glu Lys Lys Gln Gln Leu
                485                 490                 495

Leu Arg Ala Ala Thr Gly Lys Ala Ile Leu Asn Gly Ile Asp Ser Ile
                500                 505                 510

Asn Lys Val Leu Asp His Phe Arg Arg Lys Gly Ile Asn Gln His Val
                515                 520                 525

Gln Asn Gly Tyr His Gly Ile Val Met Asn Asn Phe Glu Cys Glu Pro
530                 535                 540

Ala Phe Tyr Thr Cys Val Glu Val Thr Ala Gly Asn Arg Leu Phe Tyr
545                 550                 555                 560

His Ile Val Asp Ser Asp Glu Val Ser Thr Lys Ile Leu Met Glu Phe
                565                 570                 575

Asn Lys Met Asn Leu Pro Gly Glu Val Thr Phe Leu Pro Leu Asn Lys
                580                 585                 590

Leu Asp Val Arg Asp Thr Ala Tyr Pro Glu Thr Asn Asp Ala Ile Pro
                595                 600                 605

Met Ile Ser Lys Leu Arg Tyr Asn Pro Arg Phe Asp Lys Ala Phe Lys
610                 615                 620

His Val Phe Gly Lys Thr Leu Ile Cys Arg Ser Met Glu Val Ser Thr
625                 630                 635                 640

Gln Leu Ala Arg Ala Phe Thr Met Asp Cys Ile Thr Leu Glu Gly Asp
                645                 650                 655

Gln Val Ser His Arg Gly Ala Leu Thr Gly Gly Tyr Tyr Asp Thr Arg
                660                 665                 670

Lys Ser Arg Leu Glu Leu Gln Lys Asp Val Arg Lys Ala Glu Glu Glu
                675                 680                 685

Leu Gly Glu Leu Glu Ala Lys Leu Asn Glu Asn Leu Arg Arg Asn Ile
690                 695                 700

Glu Arg Ile Asn Asn Glu Ile Asp Gln Leu Met Asn Gln Met Gln Gln
705                 710                 715                 720

Ile Glu Thr Gln Gln Arg Lys Phe Lys Ala Ser Arg Asp Ser Ile Leu
                725                 730                 735

Ser Glu Met Lys Met Leu Lys Glu Lys Arg Gln Gln Ser Glu Lys Thr
                740                 745                 750

Phe Met Pro Lys Gln Arg Ser Leu Gln Ser Leu Glu Ala Ser Leu His
                755                 760                 765

Ala Met Glu Ser Thr Arg Glu Ser Leu Lys Ala Glu Leu Gly Thr Asp
770                 775                 780

Leu Leu Ser Gln Leu Ser Leu Glu Asp Gln Lys Arg Val Asp Ala Leu
785                 790                 795                 800

Asn Asp Glu Ile Arg Gln Leu Gln Gln Glu Asn Arg Gln Leu Leu Asn
                805                 810                 815

Glu Arg Ile Lys Leu Glu Gly Ile Ile Thr Arg Val Glu Thr Tyr Leu
                820                 825                 830

Asn Glu Asn Leu Arg Lys Arg Leu Asp Gln Val Glu Gln Glu Leu Asn
                835                 840                 845

Glu Leu Arg Glu Thr Glu Gly Gly Thr Val Leu Thr Ala Thr Thr Ser
                850                 855                 860

Glu Leu Glu Ala Ile Asn Lys Arg Val Lys Asp Thr Met Ala Arg Ser
865                 870                 875                 880
```

Glu Asp Leu Asp Asn Ser Ile Asp Lys Thr Glu Ala Gly Ile Lys Glu
                885                 890                 895

Leu Gln Lys Ser Met Glu Arg Trp Lys Asn Met Glu Lys His Met
        900                 905                 910

Asp Ala Ile Asn His Asp Thr Lys Glu Leu Glu Lys Met Thr Asn Arg
        915                 920                 925

Gln Gly Met Leu Leu Lys Lys Lys Glu Cys Met Lys Lys Ile Arg
    930                 935                 940

Glu Leu Gly Ser Leu Pro Gln Glu Ala Phe Glu Lys Tyr Gln Thr Leu
945                 950                 955                 960

Ser Leu Lys Gln Leu Phe Arg Lys Leu Glu Gln Cys Asn Thr Glu Leu
                965                 970                 975

Lys Lys Tyr Ser His Val Asn Lys Lys Ala Leu Asp Gln Phe Val Asn
                980                 985                 990

Phe Ser Glu Gln Lys Glu Lys Leu Ile Lys Arg Gln Glu Glu Leu Asp
            995                 1000                1005

Arg Gly Tyr Lys Ser Ile Met Glu Leu Met Asn Val Leu Glu Leu
    1010                1015                1020

Arg Lys Tyr Glu Ala Ile Gln Leu Thr Phe Lys Gln Val Ser Lys
    1025                1030                1035

Asn Phe Ser Glu Val Phe Gln Lys Leu Val Pro Gly Gly Lys Ala
    1040                1045                1050

Thr Leu Val Met Lys Lys Gly Asp Val Glu Gly Ser Gln Ser Gln
    1055                1060                1065

Asp Glu Gly Glu Gly Ser Gly Glu Ser Glu Arg Gly Ser Gly Ser
    1070                1075                1080

Gln Ser Ser Val Pro Ser Val Asp Gln Phe Thr Gly Val Gly Ile
    1085                1090                1095

Arg Val Ser Phe Thr Gly Lys Gln Gly Glu Met Arg Glu Met Gln
    1100                1105                1110

Gln Leu Ser Gly Gly Gln Lys Ser Leu Val Ala Leu Ala Leu Ile
    1115                1120                1125

Phe Ala Ile Gln Lys Cys Asp Pro Ala Pro Phe Tyr Leu Phe Asp
    1130                1135                1140

Glu Ile Asp Gln Ala Leu Asp Ala Gln His Arg Lys Ala Val Ser
    1145                1150                1155

Asp Met Ile Met Glu Leu Ala Val His Ala Gln Phe Ile Thr Thr
    1160                1165                1170

Thr Phe Arg Pro Glu Leu Leu Glu Ser Ala Asp Lys Phe Tyr Gly
    1175                1180                1185

Val Lys Phe Arg Asn Lys Val Ser His Ile Asp Val Ile Thr Ala
    1190                1195                1200

Glu Met Ala Lys Asp Phe Val Glu Asp Asp Thr Thr His Gly
    1205                1210                1215

<210> SEQ ID NO 31
<211> LENGTH: 648
<212> TYPE: DNA
<213> ORGANISM: Homo sapiens

<400> SEQUENCE: 31
atgaacctcg tgggcagcta cgcacaccat caccaccatc accaccgca ccctgcgcac      60 cccatgctcc acgaaccctt cctcttcggt ccggcctcgc gctgtcatca ggaaaggccc    120

```
tacttccaga gctggctgct gagcccggct gacgctgccc cggacttccc tgcgggcggg      180
ccgccgcccg cggccgctgc agccgccacc gcctatggtc ctgacgccag gcctgggcag      240
agccccgggc ggctggaggc gcttggcggc cgtcttggcc ggcggaaagg ctcaggaccc      300
aagaaggagc ggagacgcac tgagagcatt aacagcgcat cgcggagtt gcgcgagtgc       360 atccccaacg tgccggccga caccaagctc tccaagatca agactctgcg cctagccacc      420
agctacatcg cctacctgat ggacgtgctg gccaaggatg cacagtctgg cgatcccgag      480
gccttcaagg ctgaactcaa gaaggcggat ggcggccgtg agagcaagcg gaaaagggag      540
ctgcagcagc acgaaggttt tcctcctgcc ctgggcccag tcgagaagag gattaaagga      600
cgcaccggct ggccgcagca agtctgggcg ctggagttaa accagtga                   648
```

<210> SEQ ID NO 32
<211> LENGTH: 215
<212> TYPE: PRT
<213> ORGANISM: Homo sapiens

<400> SEQUENCE: 32

```
Met Asn Leu Val Gly Ser Tyr Ala His His His His His His Pro
1               5                   10                  15

His Pro Ala His Pro Met Leu His Glu Pro Phe Leu Phe Gly Pro Ala
                20                  25                  30

Ser Arg Cys His Gln Glu Arg Pro Tyr Phe Gln Ser Trp Leu Leu Ser
            35                  40                  45

Pro Ala Asp Ala Ala Pro Asp Phe Pro Ala Gly Gly Pro Pro Ala
50                  55                  60

Ala Ala Ala Ala Thr Ala Tyr Gly Pro Asp Ala Arg Pro Gly Gln
65              70                  75                  80

Ser Pro Gly Arg Leu Glu Ala Leu Gly Gly Arg Leu Gly Arg Lys
                85                  90                  95

Gly Ser Gly Pro Lys Lys Glu Arg Arg Arg Thr Glu Ser Ile Asn Ser
            100                 105                 110

Ala Phe Ala Glu Leu Arg Glu Cys Ile Pro Asn Val Pro Ala Asp Thr
        115                 120                 125

Lys Leu Ser Lys Ile Lys Thr Leu Arg Leu Ala Thr Ser Tyr Ile Ala
130                 135                 140

Tyr Leu Met Asp Val Leu Ala Lys Asp Ala Gln Ser Gly Asp Pro Glu
145                 150                 155                 160

Ala Phe Lys Ala Glu Leu Lys Lys Ala Asp Gly Gly Arg Glu Ser Lys
                165                 170                 175

Arg Lys Arg Glu Leu Gln Gln His Glu Gly Phe Pro Pro Ala Leu Gly
            180                 185                 190

Pro Val Glu Lys Arg Ile Lys Gly Arg Thr Gly Trp Pro Gln Gln Val
        195                 200                 205

Trp Ala Leu Glu Leu Asn Gln
    210                 215
```

<210> SEQ ID NO 33
<211> LENGTH: 5865
<212> TYPE: DNA
<213> ORGANISM: Homo sapiens

<400> SEQUENCE: 33

```
atgcggggcc cagtgggcac cgaggaggag ctgccgcggc tgttcgccga ggagatggag      60
aatgaggacg agatgtcaga agaagaagat ggtggtcttg aagccttcga tgacttttc      120
```

```
cctgtggagc ccgtgagcct tcctaagaag aagaaaccca agaagctcaa ggaaaacaag    180
tgtaaaggga agcggaagaa gaaagagggg agcaatgatg agctatcaga gaatgaagag    240
gatctggaag agaagtcgga gagtgaaggc agtgactact ccccgaataa aagaagaag     300 aagaaactca aggacaagaa ggagaaaaaa gccaagcgaa aaagaagga tgaggatgag     360 gatgataatg atgatggatg cttaaaggag cccaagtcct cggggcagct catggccgag    420
tggggcctgg acgacgtgga ctacctgttc tcggaggagg attaccacac gctgaccaac    480
tacaaggcct tcagccagtt cctcaggcca ctcattgcca agaagaaccc gaagatcccc    540
atgtccaaaa tgatgaccgt cctgggtgcc aagtggcggg agttcagcgc caacaacccc    600
ttcaagggca gctccgcggc agcagcggcg gcggcggtgg ctgcggctgt agagacggtc    660
accatctccc ctccgctagc cgtcagcccc cgcaggtgc cccagcctgt gcctatccgc      720
aaggccaaga ccaaggaggg caaagggcct ggagtgagga agaagatcaa aggctccaaa    780
gatgggaaga aaaagggcaa agggaaaaag acggccgggc tcaagttccg cttcgggggg    840
atcagcaaca agaggaagaa aggctcctcg agtgaagaag atgagaggga ggagtcggac    900
ttcgacagcg ccagcatcca cagtgcctcc gtgcgctccg aatgctctgc agccctgggc    960
aagaagagca agaggaggcg caagaagaag aggattgatg atggtgacgg ctatgagaca   1020
gaccaccagg attactgtga ggtgtgccag cagggtgggg agatcatcct gtgcgacacc   1080
tgcccgaggg cctaccatct cgtatgcctg acccagagc tggagaaggc tcccgagggc    1140
aagtggagct gcccccactg tgagaaggag gggatccagt gggagccgaa ggacgacgac   1200
gatgaagagg aggagggcgg ctgcgaggag gaggaggacc accacatgga gttctgccgc    1260
gtgtgcaagg acggggcga gctgctctgc tgcgacgcct gccctcctc ctaccacctg      1320 cattgcctca acccgccgct gcccgagatc ccaaacggtg aatggctctg cccgcgctgt   1380
acttgccccc cactgaaggg caaagtccag cggattctac actggaggtg acgagccc     1440 cctgcccct tcatggtggg gctgccgggg cctgacgtgg agcccagcct ccctccacct    1500
aagcccctgg agggcatccc tgagagagag ttctttgtca agtgggcagg gctgtcctac   1560
tggcattgct cctgggtgaa ggagctacag ctggagctgt accacacggt gatgtatcgc   1620
aactaccaaa gaaagaacga catggatgag ccgccccct ttgactacgg ctctgggat     1680 gaagacggca agagcgagaa gaggaagaac aaggaccccc tctatgccaa gatggaggag   1740
cgcttctacc gctatggcat caagccagag tggatgatga ttcaccgaat cctgaaccat   1800
agctttgaca agaaggggga tgtgcactac ctgatcaagt ggaaagacct gccctacgac   1860
cagtgcacct gggagatcga tgacatcgac atccctact acgacaacct caagcaggcc   1920
tactggggcc acagggagct gatgctggga gaagacacca ggctgcccaa gaggctgctc   1980
aagaagggca agaagctgag ggacgacaag caggagaagc cgccggacac gcccattgtg   2040
gaccccacgt caagttcga caagcagcca tggtacatcg actccacagg cggcacactg   2100
cacccgtacc agctggaggg cctcaactgg ctgcgcttct cttgggccca gggcactgac   2160
accatcctgg ccgatgagat gggtctgggc aagacggtgc agaccatcgt gttcctttac   2220
tccctctaca aggagggcca ctccaaaggg ccctacctgg ttagcgcgcc cctctccacc   2280
atcatcaact gggaacgcga gtttgagatg tgggcgcccg acttctacgt ggtcacctac   2340 acggggagaca aggagagccg ctcggtgatt cgggagaacg agttttcctt tgaggacaac   2400
gccattcgga gtgggaagaa ggtattccgt atgaagaaag aagtgcagat caaattccac   2460
```

```
gtgctgctca cctcctatga gctcatcacc attgaccagg ccatcctggg ctccatcgag   2520
tgggcctgcc tggtggtaga tgaggcccac cgcctcaaga caaccagtc caagttttttt  2580 agggtcttaa acagctacaa gattgattac aagctgctgc tgacagggac ccccttcag   2640 aacaacctgg aggagctgtt ccatctcctc aacttcctga ctccagagag gttcaacaac  2700
ctggagggct tcctggagga gttgctgac atctccaagg aagaccagat caagaagctg   2760
catgacctgc tggggccgca catgctcagg cggctcaagg ctgacgtgtt caagaacatg  2820
ccggccaaga ccgagctcat tgtccgggtg gagctgagcc agatgcagaa gaagtactac  2880
aagttcatcc tcacacggaa ctttgaggca ctgaactcca agggggcgg gaaccaagta   2940 tcgctgctca acatcatgat ggacctgaaa aagtgctgca accacccta cctcttccct   3000 gtggctgccg tggaggcccc tgtcttgccc aatggctcct acgatggaag ctccctggtc  3060
aagtcttcag gaagctcat gctgctacag aagatgctga agaaactgcg ggatgagggg   3120
caccgtgtgc tcatcttctc ccagatgacc aagatgctgg acctcctgga ggacttcctg  3180
gagtacgaag gctacaagta tgagcggatt gatggtggca tcaccggggg cctccggcag  3240
gaggcaatcg acagattcaa tgcccccggg gcccagcagt tctgcttcct cctctcaacc  3300
cgggcaggtg gtctgggcat caacctggcc acggcggaca ctgtcatcat ctacgactcg  3360
gactggaacc cgcacaatga catccaggcc ttcagccgcg cccaccgcat cggccagaac  3420
aagaaggtga tgatctaccg cttcgtgact cgggcctcgg tggaggagcg catcacgcag  3480
gtggccaagc gcaagatgat gctcacccac ctggtggtgc ggcccggcct cggctccaag  3540
tcggggtcca tgaccaagca ggagctggac gacatcctca gttcggcac ggaggaactc   3600 ttcaaggacg acgtggaggg catgatgtct cagggccaga ggccggtcac acccatccct  3660
gatgtccagt cctccaaagg ggggaacttg gccgccagtg caaagaagaa gcacggtagc  3720
accccgccag gtgacaacaa ggacgtggag gacagcagtg tgatccacta tgacgatgcg  3780
gccatctcca gctgctggga ccggaaccag gacgctacag atgacacgga gctacagaac  3840
atgaacgagt acctgagctc cttcaaggtg gcgcagtacg tggtgcgcga ggaggacggc  3900
gtggaggagg tggagcggga aatcatcaag caggaggaga cgtggaccc cgactactgg  3960 gagaagctgc tgcggcacca ctatgagcag cagcaggagg acctggcccg caacctgggc  4020
aagggcaagc gcatccgcaa gcaggtcaac tacaacgatg cctcccagga ggaccaggag  4080
tggcaggatg agctctctga taaccagtca gaatattcca ttggctctga ggatgaggat  4140
gaggactttg aagagaggcc ggaagggcag agtggacgac gacaatcccg gaggcagctg  4200
aagagtgaca gggacaagcc cctgccccg cttctcgccc gagttggtgg caacatcgag   4260
gtgctgggct tcaatgcccg acagcggaag gcctttctga cgccatcat gcgctggggc  4320 atgccccgc aggacgcctt caactcccac tggctggtgc gggaccttcg agggaagagc  4380
gagaaggagt ttagagccta tgtgtccctc ttcatgcggc acctgtgtga gccggggcg  4440 gatggtgcag agaccttcgc agacggcgtg ccccgggagg gcctctccag gcagcacgtg  4500
ctgacccgca tcggggtcat gtcactagtt aggaagaagg ttcaggagtt tgagcatgtc  4560
aacgggaagt acagcaccccc agacttgatc cctgaggggc ccgaggggaa gaagtcgggc  4620
gaggtgatct cctcggaccc caacacacca gtgcccgcca gccctgccca cctcctgcca  4680
gccccgctgg gcctgccaga caaaatggaa gcccagctgg gctacatgga tgagaaagac  4740 cccgggggcac agaagccaag gcagcccctg gaagtccagg cccttccagc cgccttggat  4800
agagtggaga gtgaggacaa gcacgagagc ccagccagca aggagagagc ccgagaggag  4860
```

-continued

```
cggccagagg agacggagaa ggccccgccc tccccggagc agctgccgag agaggaggtg    4920
cttcctgaga aggagaagat cctggacaag ctggagctga gcttgatcca cagcagaggg    4980
gacagttccg aactcaggcc agatgacacc aaggctgagg agaaggagcc cattgaaaca    5040
cagcaaaatg gtgacaaaga ggaagatgac gaggggaaga aggaggacaa aaggggaaa    5100 ttcaagttca tgttcaacat cgcggacggg ggcttcacgg agttgcacac gctgtggcag    5160
aacgaggagc gggctgctgt atcctctggg aaaatctacg acatctggca ccggcgccat    5220
gactactggc tgctggcggg catcgtgacg cacggctacg cccgctggca ggacatccag    5280
aatgacccac ggtacatgat cctcaacgag cccttcaagt ctgaggtcca aagggcaac    5340 tacctggaga tgaagaacaa gttcctggcc cgcaggttta agctgctgga gcaggcgttg    5400
gtcattgagg agcagctccg gagggccgcg tacctgaaca tgacgcagga ccccaaccac    5460
cccgccatgg ccctcaacgc ccgcctggct gaagtggagt gcctcgccga gaccaccag    5520 cacctgtcca aggagtccct tgctgggaac aagcctgcca atgccgtcct gcacaaggtc    5580
ctgaaccagc tggaggagct gctgagcgac atgaaggccg acgtgacccg gctgccatcc    5640
atgctgtccc gcatccccc ggtggccgcc cggctgcaga tgtcggagcg cagcatcctg    5700
agccgcctga ccaaccgcgc cggggacccc accatccagc agggcgcttt cggctcctcc    5760
cagatgtaca gcaacaactt tgggcccaac ttccgggggcc ctggaccggg agggattgtc    5820
aactacaacc agatgccct ggggccctat gtgaccgata tctag              5865
```

<210> SEQ ID NO 34
<211> LENGTH: 1954
<212> TYPE: PRT
<213> ORGANISM: Homo sapiens

<400> SEQUENCE: 34

```
Met Arg Gly Pro Val Gly Thr Glu Glu Glu Leu Pro Arg Leu Phe Ala
1               5                   10                  15

Glu Glu Met Glu Asn Glu Asp Glu Met Ser Glu Glu Asp Gly Gly
            20                  25                  30

Leu Glu Ala Phe Asp Asp Phe Phe Pro Val Glu Pro Val Ser Leu Pro
        35                  40                  45

Lys Lys Lys Lys Pro Lys Lys Leu Lys Glu Asn Lys Cys Lys Gly Lys
    50                  55                  60

Arg Lys Lys Lys Glu Gly Ser Asn Asp Glu Leu Ser Glu Asn Glu Glu
65                  70                  75                  80

Asp Leu Glu Glu Lys Ser Glu Ser Glu Gly Ser Asp Tyr Ser Pro Asn
                85                  90                  95

Lys Lys Lys Lys Lys Lys Leu Lys Asp Lys Lys Glu Lys Ala Lys
            100                 105                 110

Arg Lys Lys Lys Asp Glu Asp Glu Asp Asn Asp Gly Cys Leu
        115                 120                 125

Lys Glu Pro Lys Ser Ser Gly Gln Leu Met Ala Glu Trp Gly Leu Asp
    130                 135                 140

Asp Val Asp Tyr Leu Phe Ser Glu Glu Asp Tyr His Thr Leu Thr Asn
145                 150                 155                 160

Tyr Lys Ala Phe Ser Gln Phe Leu Arg Pro Leu Ile Ala Lys Lys Asn
                165                 170                 175

Pro Lys Ile Pro Met Ser Lys Met Met Thr Val Leu Gly Ala Lys Trp
            180                 185                 190
```

```
Arg Glu Phe Ser Ala Asn Asn Pro Phe Lys Gly Ser Ser Ala Ala Ala
                195                 200                 205

Ala Ala Ala Ala Val Ala Ala Val Glu Thr Val Thr Ile Ser Pro
    210                 215                 220

Pro Leu Ala Val Ser Pro Gln Val Pro Gln Pro Val Pro Ile Arg
225                 230                 235                 240

Lys Ala Lys Thr Lys Glu Gly Lys Gly Pro Gly Val Arg Lys Lys Ile
                245                 250                 255

Lys Gly Ser Lys Asp Gly Lys Lys Gly Lys Gly Lys Lys Thr Ala
                260                 265                 270

Gly Leu Lys Phe Arg Phe Gly Ile Ser Asn Lys Arg Lys Lys Gly
        275                 280                 285

Ser Ser Ser Glu Glu Asp Glu Arg Glu Glu Ser Asp Phe Asp Ser Ala
    290                 295                 300

Ser Ile His Ser Ala Ser Val Arg Ser Glu Cys Ser Ala Ala Leu Gly
305                 310                 315                 320

Lys Lys Ser Lys Arg Arg Arg Lys Lys Arg Ile Asp Asp Gly Asp
                325                 330                 335

Gly Tyr Glu Thr Asp His Gln Asp Tyr Cys Glu Val Cys Gln Gln Gly
                340                 345                 350

Gly Glu Ile Ile Leu Cys Asp Thr Cys Pro Arg Ala Tyr His Leu Val
        355                 360                 365

Cys Leu Asp Pro Glu Leu Glu Lys Ala Pro Glu Gly Lys Trp Ser Cys
        370                 375                 380

Pro His Cys Glu Lys Glu Gly Ile Gln Trp Glu Pro Lys Asp Asp
385                 390                 395                 400

Asp Glu Glu Glu Glu Gly Gly Cys Glu Glu Glu Asp Asp His Met
                405                 410                 415

Glu Phe Cys Arg Val Cys Lys Asp Gly Gly Glu Leu Leu Cys Cys Asp
                420                 425                 430

Ala Cys Pro Ser Ser Tyr His Leu His Cys Leu Asn Pro Pro Leu Pro
        435                 440                 445

Glu Ile Pro Asn Gly Glu Trp Leu Cys Pro Arg Cys Thr Cys Pro Pro
450                 455                 460

Leu Lys Gly Lys Val Gln Arg Ile Leu His Trp Arg Trp Thr Glu Pro
465                 470                 475                 480

Pro Ala Pro Phe Met Val Gly Leu Pro Gly Pro Asp Val Glu Pro Ser
                485                 490                 495

Leu Pro Pro Pro Lys Pro Leu Glu Gly Ile Pro Glu Arg Glu Phe Phe
        500                 505                 510

Val Lys Trp Ala Gly Leu Ser Tyr Trp His Cys Ser Trp Val Lys Glu
        515                 520                 525

Leu Gln Leu Glu Leu Tyr His Thr Val Met Tyr Arg Asn Tyr Gln Arg
    530                 535                 540

Lys Asn Asp Met Asp Glu Pro Pro Phe Asp Tyr Gly Ser Gly Asp
545                 550                 555                 560

Glu Asp Gly Lys Ser Glu Lys Arg Lys Asn Lys Asp Pro Leu Tyr Ala
                565                 570                 575

Lys Met Glu Glu Arg Phe Tyr Arg Tyr Gly Ile Lys Pro Glu Trp Met
                580                 585                 590

Met Ile His Arg Ile Leu Asn His Ser Phe Asp Lys Lys Gly Asp Val
        595                 600                 605

His Tyr Leu Ile Lys Trp Lys Asp Leu Pro Tyr Asp Gln Cys Thr Trp
```

```
                610             615             620
Glu Ile Asp Asp Ile Asp Ile Pro Tyr Tyr Asp Asn Leu Lys Gln Ala
625             630             635             640

Tyr Trp Gly His Arg Glu Leu Met Leu Gly Glu Asp Thr Arg Leu Pro
                645             650             655

Lys Arg Leu Leu Lys Lys Gly Lys Lys Leu Arg Asp Asp Lys Gln Glu
            660             665             670

Lys Pro Pro Asp Thr Pro Ile Val Asp Pro Thr Val Lys Phe Asp Lys
            675             680             685

Gln Pro Trp Tyr Ile Asp Ser Thr Gly Gly Thr Leu His Pro Tyr Gln
            690             695             700

Leu Glu Gly Leu Asn Trp Leu Arg Phe Ser Trp Ala Gln Gly Thr Asp
705             710             715             720

Thr Ile Leu Ala Asp Glu Met Gly Leu Gly Lys Thr Val Gln Thr Ile
                725             730             735

Val Phe Leu Tyr Ser Leu Tyr Lys Glu Gly His Ser Lys Gly Pro Tyr
                740             745             750

Leu Val Ser Ala Pro Leu Ser Thr Ile Ile Asn Trp Glu Arg Glu Phe
            755             760             765

Glu Met Trp Ala Pro Asp Phe Tyr Val Val Thr Tyr Thr Gly Asp Lys
770             775             780

Glu Ser Arg Ser Val Ile Arg Glu Asn Glu Phe Ser Phe Glu Asp Asn
785             790             795             800

Ala Ile Arg Ser Gly Lys Lys Val Phe Arg Met Lys Lys Glu Val Gln
                805             810             815

Ile Lys Phe His Val Leu Leu Thr Ser Tyr Glu Leu Ile Thr Ile Asp
                820             825             830

Gln Ala Ile Leu Gly Ser Ile Glu Trp Ala Cys Leu Val Val Asp Glu
            835             840             845

Ala His Arg Leu Lys Asn Asn Gln Ser Lys Phe Phe Arg Val Leu Asn
850             855             860

Ser Tyr Lys Ile Asp Tyr Lys Leu Leu Leu Thr Gly Thr Pro Leu Gln
865             870             875             880

Asn Asn Leu Glu Glu Leu Phe His Leu Leu Asn Phe Leu Thr Pro Glu
            885             890             895

Arg Phe Asn Asn Leu Glu Gly Phe Leu Glu Glu Phe Ala Asp Ile Ser
            900             905             910

Lys Glu Asp Gln Ile Lys Lys Leu His Asp Leu Leu Gly Pro His Met
            915             920             925

Leu Arg Arg Leu Lys Ala Asp Val Phe Lys Asn Met Pro Ala Lys Thr
930             935             940

Glu Leu Ile Val Arg Val Glu Leu Ser Gln Met Gln Lys Lys Tyr Tyr
945             950             955             960

Lys Phe Ile Leu Thr Arg Asn Phe Glu Ala Leu Asn Ser Lys Gly Gly
                965             970             975

Gly Asn Gln Val Ser Leu Leu Asn Ile Met Met Asp Leu Lys Lys Cys
            980             985             990

Cys Asn His Pro Tyr Leu Phe Pro  Val Ala Ala Val Glu  Ala Pro Val
            995             1000            1005

Leu Pro  Asn Gly Ser Tyr Asp  Gly Ser Ser Leu Val  Lys Ser Ser
        1010            1015            1020

Gly Lys  Leu Met Leu Leu Gln  Lys Met Leu Lys Lys  Leu Arg Asp
        1025            1030            1035
```

```
Glu Gly His Arg Val Leu Ile Phe Ser Gln Met Thr Lys Met Leu
1040                1045                1050

Asp Leu Leu Glu Asp Phe Leu Glu Tyr Glu Gly Tyr Lys Tyr Glu
1055                1060                1065

Arg Ile Asp Gly Gly Ile Thr Gly Gly Leu Arg Gln Glu Ala Ile
1070                1075                1080

Asp Arg Phe Asn Ala Pro Gly Ala Gln Gln Phe Cys Phe Leu Leu
1085                1090                1095

Ser Thr Arg Ala Gly Gly Leu Gly Ile Asn Leu Ala Thr Ala Asp
1100                1105                1110

Thr Val Ile Ile Tyr Asp Ser Asp Trp Asn Pro His Asn Asp Ile
1115                1120                1125

Gln Ala Phe Ser Arg Ala His Arg Ile Gly Gln Asn Lys Lys Val
1130                1135                1140

Met Ile Tyr Arg Phe Val Thr Arg Ala Ser Val Glu Glu Arg Ile
1145                1150                1155

Thr Gln Val Ala Lys Arg Lys Met Met Leu Thr His Leu Val Val
1160                1165                1170

Arg Pro Gly Leu Gly Ser Lys Ser Gly Ser Met Thr Lys Gln Glu
1175                1180                1185

Leu Asp Asp Ile Leu Lys Phe Gly Thr Glu Glu Leu Phe Lys Asp
1190                1195                1200

Asp Val Glu Gly Met Met Ser Gln Gly Gln Arg Pro Val Thr Pro
1205                1210                1215

Ile Pro Asp Val Gln Ser Ser Lys Gly Gly Asn Leu Ala Ala Ser
1220                1225                1230

Ala Lys Lys His Gly Ser Thr Pro Pro Gly Asp Asn Lys Asp
1235                1240                1245

Val Glu Asp Ser Ser Val Ile His Tyr Asp Asp Ala Ala Ile Ser
1250                1255                1260

Lys Leu Leu Asp Arg Asn Gln Asp Ala Thr Asp Asp Thr Glu Leu
1265                1270                1275

Gln Asn Met Asn Glu Tyr Leu Ser Ser Phe Lys Val Ala Gln Tyr
1280                1285                1290

Val Val Arg Glu Glu Asp Gly Val Glu Glu Val Glu Arg Glu Ile
1295                1300                1305

Ile Lys Gln Glu Glu Asn Val Asp Pro Asp Tyr Trp Glu Lys Leu
1310                1315                1320

Leu Arg His His Tyr Glu Gln Gln Gln Glu Asp Leu Ala Arg Asn
1325                1330                1335

Leu Gly Lys Gly Lys Arg Ile Arg Lys Gln Val Asn Tyr Asn Asp
1340                1345                1350

Ala Ser Gln Glu Asp Gln Glu Trp Gln Asp Glu Leu Ser Asp Asn
1355                1360                1365

Gln Ser Glu Tyr Ser Ile Gly Ser Glu Asp Glu Asp Glu Asp Phe
1370                1375                1380

Glu Glu Arg Pro Glu Gly Gln Ser Gly Arg Arg Gln Ser Arg Arg
1385                1390                1395

Gln Leu Lys Ser Asp Arg Asp Lys Pro Leu Pro Pro Leu Leu Ala
1400                1405                1410

Arg Val Gly Gly Asn Ile Glu Val Leu Gly Phe Asn Ala Arg Gln
1415                1420                1425
```

```
Arg Lys Ala Phe Leu Asn Ala Ile Met Arg Trp Gly Met Pro Pro
    1430                1435                1440

Gln Asp Ala Phe Asn Ser His Trp Leu Val Arg Asp Leu Arg Gly
    1445                1450                1455

Lys Ser Glu Lys Glu Phe Arg Ala Tyr Val Ser Leu Phe Met Arg
    1460                1465                1470

His Leu Cys Glu Pro Gly Ala Asp Gly Ala Glu Thr Phe Ala Asp
    1475                1480                1485

Gly Val Pro Arg Glu Gly Leu Ser Arg Gln His Val Leu Thr Arg
    1490                1495                1500

Ile Gly Val Met Ser Leu Val Arg Lys Lys Val Gln Glu Phe Glu
    1505                1510                1515

His Val Asn Gly Lys Tyr Ser Thr Pro Asp Leu Ile Pro Glu Gly
    1520                1525                1530

Pro Glu Gly Lys Lys Ser Gly Glu Val Ile Ser Ser Asp Pro Asn
    1535                1540                1545

Thr Pro Val Pro Ala Ser Pro Ala His Leu Leu Pro Ala Pro Leu
    1550                1555                1560

Gly Leu Pro Asp Lys Met Glu Ala Gln Leu Gly Tyr Met Asp Glu
    1565                1570                1575

Lys Asp Pro Gly Ala Gln Lys Pro Arg Gln Pro Leu Glu Val Gln
    1580                1585                1590

Ala Leu Pro Ala Ala Leu Asp Arg Val Glu Ser Glu Asp Lys His
    1595                1600                1605

Glu Ser Pro Ala Ser Lys Glu Arg Ala Arg Glu Glu Arg Pro Glu
    1610                1615                1620

Glu Thr Glu Lys Ala Pro Pro Ser Pro Glu Gln Leu Pro Arg Glu
    1625                1630                1635

Glu Val Leu Pro Glu Lys Glu Lys Ile Leu Asp Lys Leu Glu Leu
    1640                1645                1650

Ser Leu Ile His Ser Arg Gly Asp Ser Ser Glu Leu Arg Pro Asp
    1655                1660                1665

Asp Thr Lys Ala Glu Glu Lys Glu Pro Ile Glu Thr Gln Gln Asn
    1670                1675                1680

Gly Asp Lys Glu Glu Asp Asp Glu Gly Lys Lys Glu Asp Lys Lys
    1685                1690                1695

Gly Lys Phe Lys Phe Met Phe Asn Ile Ala Asp Gly Gly Phe Thr
    1700                1705                1710

Glu Leu His Thr Leu Trp Gln Asn Glu Glu Arg Ala Ala Val Ser
    1715                1720                1725

Ser Gly Lys Ile Tyr Asp Ile Trp His Arg Arg His Asp Tyr Trp
    1730                1735                1740

Leu Leu Ala Gly Ile Val Thr His Gly Tyr Ala Arg Trp Gln Asp
    1745                1750                1755

Ile Gln Asn Asp Pro Arg Tyr Met Ile Leu Asn Glu Pro Phe Lys
    1760                1765                1770

Ser Glu Val His Lys Gly Asn Tyr Leu Glu Met Lys Asn Lys Phe
    1775                1780                1785

Leu Ala Arg Arg Phe Lys Leu Leu Glu Gln Ala Leu Val Ile Glu
    1790                1795                1800

Glu Gln Leu Arg Arg Ala Ala Tyr Leu Asn Met Thr Gln Asp Pro
    1805                1810                1815

Asn His Pro Ala Met Ala Leu Asn Ala Arg Leu Ala Glu Val Glu
```

-continued

```
            1820                1825                1830
Cys Leu Ala Glu Ser His Gln His Leu Ser Lys Glu Ser Leu Ala
        1835            1840            1845

Gly Asn Lys Pro Ala Asn Ala Val Leu His Lys Val Leu Asn Gln
        1850            1855            1860

Leu Glu Glu Leu Leu Ser Asp Met Lys Ala Asp Val Thr Arg Leu
        1865            1870            1875

Pro Ser Met Leu Ser Arg Ile Pro Pro Val Ala Ala Arg Leu Gln
        1880            1885            1890

Met Ser Glu Arg Ser Ile Leu Ser Arg Leu Thr Asn Arg Ala Gly
        1895            1900            1905

Asp Pro Thr Ile Gln Gln Gly Ala Phe Gly Ser Ser Gln Met Tyr
        1910            1915            1920

Ser Asn Asn Phe Gly Pro Asn Phe Arg Gly Pro Gly Pro Gly Gly
        1925            1930            1935

Ile Val Asn Tyr Asn Gln Met Pro Leu Gly Pro Tyr Val Thr Asp
        1940            1945            1950

Ile
```

INHIBITION OF A LNCRNA FOR TREATMENT OF NEUROBLASTOMA

CROSS-REFERENCE TO RELATED APPLICATIONS

This application is a national phase entry under 35 U.S.C. § 371 of International Patent Application PCT/EP2019/051757, filed Jan. 24, 2019, designating the United States of America and published in English as International Patent Publication WO 2019/149616 A1 on Aug. 8, 2019, which claims the benefit under Article 8 of the Patent Cooperation Treaty to European Patent Application Serial No. 18154813.2, filed Feb. 2, 2018.

TECHNICAL FIELD

The application relates to the field of cancer, particularly to the treatment of neuroblastoma. Indeed, described is that a particular long non-coding RNA (ncRNA) is specifically up-regulated in neuroblastoma cells as compared to other cancer cells and that high expression of the lncRNA correlates with a lower survival probability. Inhibition of this lncRNA in neuroblastoma cells leads to a reduction in cell growth and induction of apoptosis and is a novel therapeutic strategy in the treatment of neuroblastoma.

BACKGROUND

Neuroblastoma is a pediatric cancer, originating from immature sympathetic nervous system cells. Although the incidence is low, the mortality rate of this malignancy is high, accounting for 15% of all children's cancer deaths. To boost the survival rate, patients are stratified into risk groups with different treatment regimes. At present, the stratification is based on age at diagnosis, location of the primary tumor and degree of metastasis. Several genetic markers (MYCN amplification, lp and llq deletion and DNA ploidy), are also taken into account (Maris, 2010; Park, Eggert, & Caron, 2010). While low risk patients have excellent survival rates, patients in the high-risk group have very poor survival rates despite aggressive multi-modal treatment (Park et al., 2010). Novel insights into the genetic basis of high-risk neuroblastoma patients is therefore essential in order to better understand the course of the disease and identify novel targets for therapeutic intervention. While only 2% of our genome encodes for proteins, 80-85% of the genome is actively transcribed, resulting in thousands of so-called non-coding RNAs (Consortium, 2012). Long non-coding RNAs form the largest class and have been shown to play key roles in gene expression regulation (Ma, Bajic, & Zhang, 2013). Notably, lncRNA expression can be extremely cancer-type specific, suggesting they may play an essential role in cancer cell survival. Therefore, they are considered as novel candidate therapeutic targets. Today, only a handful of lncRNA genes have been implicated in neuroblastoma (Pandey & Kanduri, 2015).

DETAILED DESCRIPTION

Figures 1A, 1B:
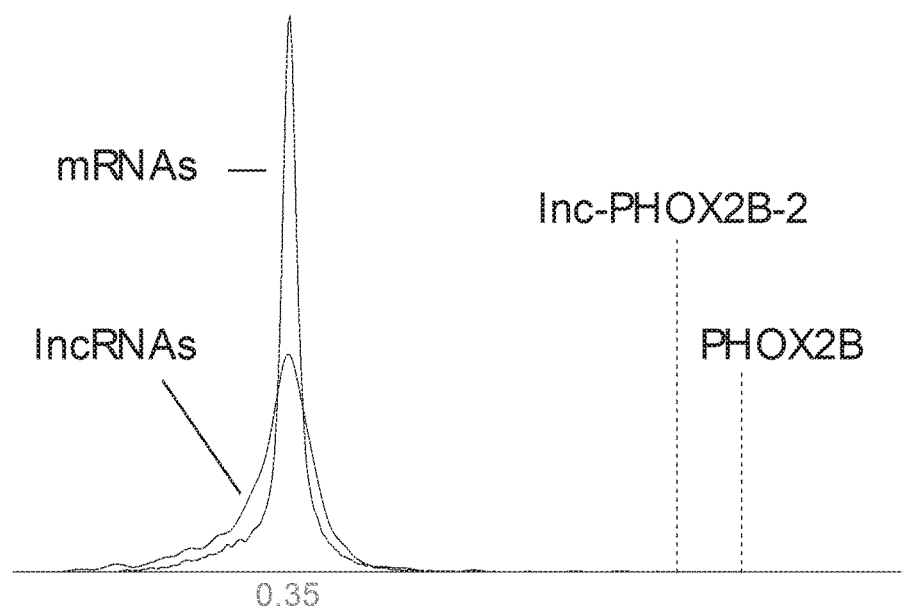
FIG. 1: lnc-PHOX2B-2 is a neuroblastoma specific lncRNA and one of the most specific genes in neuroblastoma (FIGS. 1a and 1b). Plots of the expression in the CCLE and TCGA data sets demonstrate the specificity (FIGS. 1c and 1d).

The following terms or definitions are provided solely to aid in the understanding of the disclosure. Unless specifically defined herein, all terms used herein have the same meaning as they would to one skilled in the art of the disclosure. Practitioners are particularly directed to Sambrook et al., Molecular Cloning: A Laboratory Manual, 2nd ed., Cold Spring Harbor Press, Plainsview, N.Y. (1989); and Ausubel et al., Current Protocols in Molecular Biology (Supplement 47), John Wiley & Sons, New York (1999), for definitions and terms of the art. The definitions provided herein should not be construed to have a scope less than understood by a person of ordinary skill in the art.

The term "LINC00682," "long intergenic non-protein coding RAN LINC00682," or "Lnc PHOXB 2," or Neuroblastoma Specific Phox2B Regulatory RNA (NESPR) as used herein refers to the gene with accession number ENSG00000245870 in Ensembl, as well as the RNA that is transcribed from the gene. It can also be identified with Gene ID: 101927074 or the human gene nomenclature identifier HGNC: 44466. As it is a non-protein coding gene, there is no protein product.

In humans, the gene is located on the short arm of chromosome 4, from position 41,872,764 to 41,882,596.

The gene has in total 12 transcripts (or splice variants): 1) LINC00682:1 (transcript ID ENST00000504870 in Ensembl) with a length of 632 bp (SEQ ID NO:1), 2) LINC00682:2 with a length of 1424 bp (SEQ ID NO:3), 3) LINC00683:3 with a length of 555 bp (SEQ ID NO:3); 4) LINC00682:4 (transcript ID ENST00000499082 in Ensembl) with a length of 1384 bp (SEQ ID NO:4); 5) LINC00682:5 with a length of 1362 bp (SEQ ID NO:5); 6) LINC00682:6 (transcript ID ENST00000498940 in Ensembl) with a length of 1625 bp (SEQ ID NO:6), 7) LINC00682:7 with a length of 1647 bp (SEQ ID NO:7), 8) LINC00682:8 (transcript ID ENST00000637677 in Ensembl) with a length of 931 bp (SEQ ID NO:8); 9) LINC00682:9 with a length of 728 bp (SEQ ID NO:9), 10) LINC00682:10 (transcript ID ENST00000504870 in Ensembl) with a length of 592 bp (SEQ ID NO:10), 11) LINC00682:11 (transcript ID ENST00000499082 in Ensembl) with a length of 1385 bp (SEQ ID NO:11), and 12) LINC00682:12 with a length of 1425 bp (SEQ ID NO:12).

All transcripts are lncRNA (large intergenic non-coding RNAs), their respective consensus sequences are:

1) LI NC00682:1 sequence (ENST00000504870)

(SEQ ID NO: 1)

```
TCATCATGTATAAAATGGTGCAGTAGGATGCAAAATTTCCACTTGTTTATAAG

TGTATCGCCGAGAAA

TGTATAAAATAATCGAGACCGGCGGAGGCAGGTCAGAGCCGTCTGGAATGCG

CGCACCTTCAACCA

CTTTGGGAGGCCGAGGCAGGTGGATCACCTCAGGTCAGGAGTTCGAGACCAG

CGTGACCAACATGG

TGAAACCCGTCTCTACTAAAAATACAAAAAATTAGATGGGTATGGTGGCGCG

TGCCTGTCTGCTACT

CGGGAGGCTGAGGCAGGAGAACCTTGGAGGCAAAGGTTGCAGTGAGCTGAG

ATCAAGCCACCGCA

CTCCAG CCTG GG CG AC AG CG CAAAACTTTGTCTC

AAAAAAAAAAAAAAAA AAAGTCCG C AGTATG

GTTTTCACATTATCACTCTCAATGCCATTGGAGGTAGGTCCAAGCTGGTGTCT

CTTTGATTAGTCTCCC

TAAACCCATCTATTCATTTACTAGCCATTAGTTATTCTTTAATTGAGTCCAAA

AATGTTTGTGAGGAGA

TAGTCCCATATGAGATTAAAAGAAAGAAAGAAAACAAAACAACAAACAAAC

AAACAAAACAGAAAA

T CAG GT GT AGTGG ACACTG AAG AGTTT CT G
```

2) LI NC00682:2 sequence (SEQ ID NO: 2)

```
TCATCATGTATAAAATGGTGCAGTAGGATGCAAAATTTCCACTTGTTTATAAG

TGTATCGCCGAGAAA
```

-continued

```
TGTATAAAATAATCGAGACCGGCGGAGGCAGGTCAGAGCCGTCTGGAATGCG

CGCACCTTCAACGG

TATTTGGAGATTATTCGCACTGAATTTTCTGCCCGCCAAGAACGAATAGGATT

GCCAAGCCACACCAC

TTTTTGGAGCCCGCTTATTCGCGCCTATCCACCCTCTCCTGTGCCCCAGGTTCC

CTGAGCACGGGAAT

CCTTTCCGGGCATGGCCAAGTTTGTTCGGTGGCTCAGAGCGGGAAGGGAAGT

GCAGTTCGACACCT

GTCCAGCTGCTCCGCTTGGAGATCAAAGGCCGGCTATGGGCTGAGCGACAGA

TTTACGGGACGGTG

GTACAGATTAAGGCGAGAACCCTGCCGGTCCTGGACTCGAGTTCGCACCCAA

GGAAAGCGTACAGG

TCCCTGGAAGCGGGTGGATGTCGGAGAGGCCGAGGCAGCCTGCGCTGTGGCC

AGGCAGGCTTGGT

GGGCTTTAGTCTCAGTATGTGTTCTTTAAAGTCTTGACAGGTTATTAGTAAAG

GAAGGGGCACCCCA

GGGTCATGAAGATGCTTCTCGCTCTGGCCCAAGCATGCTGAGGCTCGCTTATT

CCTCGGCCAGGCCC

AGTAAAACAGCTCAAGCACAGCCTGGAGTCTTCCCGCATCTGCGCGGGAGTA

GAGTCTGGCTTTGG

GCCCCGCGTACCCCGCAGTCGTCGGGGACCAGTTCGAGGCCACGGGAAGGGT

TTCCGCGGCAGGGC

GCGGAGTAAAGAGGGGAAGAAGGAATCCTCTCCGCGTGATCAGTAGGGCGG

GCTTGTGATACTCTC

ACACCCAGGTTCCAGCTCAGCCCCCAAACTGCTGCCCCAAGAAAACAAGTTG

GGGAGTGTGGATTTA

G ACAT AACAACGG GT GAG CT GAT GT CCTT ACAACCAAAAAT ATT GAG

ACT AG AAATT CAG CTCCG

AATCCACGACCCTCAGATTGATGCTTAATCGCACCCTCGACTCCAGAAAAGC

TGCCGGGGACAGACA

TGGACAGGTTTTGCCAAGGGTTCATTAAAATAGTCTGCACTGGAATAACCGG

GGTGCAAGAGATCAC

GTCTTCACTCAGGGCTTTGGGGATCCCCTCGTCGCCCCAGGTCAGTGGGTGGG

GAGGAGGGCAAAC

TTCTGTCTTTTGTTTGTGGGTGAGGGATGCGAATTGTGGCAGCAGCCGAGAAA

AGGGGGGAAATTA

ATTG CAG CCAATT AATAATT AATCCCCTTT AAA CAG CTTT ATT AT CT CTT

CTGGGCGACAG AG ATTT GT
```

-continued

CTGATAACCCCCTGAAGACCAAATGTCAAGTTTAACCAAATAGTTATTGCTTT

ATCAACCCGAGTCTG

C AA AT AAATT A AT C AAA AG CAA

3) LI NC00682:3 sequence
(SEQ ID NO: 3)

TGGTGCAGTAGGATGCAAAATTTCCACTTGTTTATAAGTGTATCGCCGAGAA

ATGTATAAAATAATC

GAGACCGGCGGAGGCAGGTCAGAGCCGTCTGGAATGCGCGCACCTTCAACG

AACAATGCCAACATT

GAAGTCCTCGGTTGGAGTCTGCACAGTTGGAGATCTTTGGTGCCATTTTAGAC

ATCTTTGGATTTCAT

CAATCAAACTGACTGCAATTTTCCATAAAAACCCTGAATTTGGGTCAGAAAG

TGGGCAAAGTAGATA

AAGATCATTCGAGCTGTCTTATAAGATGATAAATAGATATCCTTTCAGGCCAA

CAATGCCAAAGTGCA

GTTTTGTGATTCCCTTCCATGGGTTCTGAATGCAGTGAGTCGAAACGATTTCT

ACATGTTTTCCCATGG

TTTAGGAGGTGTCTTTACATACTTGTCAATAGTAGCCTGACCTTTTTCCCCATG

GAGTTGCTAAGTGT GTTTTGTTTGTTG CTTT G AGT ACTTTTTT CTTGTT GTTT

GT GT GT GT GTT G C AC AAAATACAC AAG AAA AT AAAGGTTTTTT

4) LI NC00682 :4 sequence (ENST00000499082)
(SEQ ID NO: 4)

CTTGTTTATAAGTGTATCGCCGAGAAATGTATAAAATAATCGAGACCGGCGG

AGGCAGGTCAGAGC

CGTCTGGAATGCGCGCACCTTCAACGGTATTTGGAGATTATTCGCACTGAATT

TTCTGCCCGCCAAGA

ACGAATAGGATTGCCAAGCCACACCACTTTTTGGAGCCCGCTTATTCGCGCCT

ATCCACCCTCTCCTGT

GCCCCAGGTTCCCTGAGCACGGGAATCCTTTCCGGGCATGGCCAAGTTTGTTC

GGTGGCTCAGAGCG

GGAAGGGAAGTGCAGTTCGACACCTGTCCAGCTGCTCCGCTTGGAGATCAAA

GGCCGGCTATGGGC

TGAGCGACAGATTTACGGGACGGTGGTACAGATTAAGGCGAGAACCCTGCCG

GTCCTGGACTCGAG

TTCGCACCCAAGGAAAGCGTACAGGTCCCTGGAAGCGGGTGGATGTCGGAGA

GGCCGAGGCAGCC

TGCGCTGTG GCCAGG C AG G CTT G GTG G G CTTT AGTCTCAGTATGTGTT

CTTT A A AGT CTT GAC AG GTT

ATTAGTAAAGGAAGGGGCACCCCAGGGTCATGAAGATGCTTCTCGCTCTGGC

CCAAGCATGCTGAG

GCTCGCTTATTCCTCGGCCAGGCCCAGTAAAACAGCTCAAGCACAGCCTGGA

GTCTTCCCGCATCTGC

-continued

GCGGGAGTAGAGTCTGGCTTTGGGCCCCGCGTACCCCGCAGTCGTCGGGGAC

CAGTTCGAGGCCAC

GGGAAGGGTTTCCGCGGCAGGGCGCGGAGTAAAGAGGGGAAGAAGGAATCC

TCTCCGCGTGATCA

GTAGGGCGGGCTTGTGATACTCTCACACCCAGGTTCCAGCTCAGCCCCCAAA

CTGCTGCCCCAAGAA

AACAAGTTGGGGAGTGTGGATTTAGACATAACAACGGGTGTGAGCTGATGTC

CTTACAACCAAAAA

TATTGAGACTAGAAATTCAGCTCCGAATCCACGACCCTCAGATTGATGCTTAA

TCGCACCCTCGACTC

CAGAAAAGCTGCCGGGGACAGACATGGACAGGTTTTGCCAAGGGTTCATTAA

AATAGTCTGCACTG

GAATAACCGGGGTGCAAGAGATCACGTCTTCACTCAGGGCTTTGGGGATCCC

CTCGTCGCCCCAGGT

CAGTGGGTGGGGAGGAGGGCAAACTTCTGTCTTTTGTTTGTGGGTGAGGGAT

GCGAATTGTGGCAG

C AG C CG AG A A A AG G G G G G A A ATT A ATT G C AG CCA ATT A AT A

ATT A AT C CC CTTT A A AC AG CTTT ATT A

TCTCTTCTGGGCGACAGAGATTTGTCTGATAACCCCCTGAAGACCAAATGTCA

AGTTTAACCAAATAG

TT ATT G CTTT AT CAACCCG AGT CT G CAAAT AAATT AAT C AAAAG C AAA

5) LI NC00682:5 sequence (SEQ ID NO: 5)

GCCGAGAAATGTATAAAATAATCGAGACCGGCGGAGGCAGGTCAGAGCCGT

CTGGAATGCGCGCA

CCTTCAACGGTATTTGGAGATTATTCGCACTGAATTTTCTGCCCGCCAAGAAC

GAATAGGATTGCCAA

GCCACACCACTTTTTGGAGCCCGCTTATTCGCGCCTATCCACCCTCTCCTGTG

CCCCAGGTTCCCTGAG

CACGGGAATCCTTTCCGGGCATGGCCAAGTTTGTTCGGTGGCTCAGAGCGGG

AAGGGAAGTGCAGT

TCGACACCTGTCCAGCTGCTCCGCTTGGAGATCAAAGGCCGGCTATGGGCTG

AGCGACAGATTTACG

GGACGGTGGTACAGATTAAGGCGAGAACCCTGCCGGTCCTGGACTCGAGTTC

GCACCCAAGGAAAG

CGTACAGGTCCCTGGAAGCGGGTGGATGTCGGAGAGGCCGAGGCAGCCTGC

GCTGTGGCCAGGCA

GGCTTGGTGGGCTTTAGTCTCAGTATGTGTTCTTTAAAGTCTTGACAGGTTAT

TAGTAAAGGAAGGG

GCACCCCAGGGTCATGAAGATGCTTCTCGCTCTGGCCCAAGCATGCTGAGGC

TCGCTTATTCCTCGGC

CAGGCCCAGTAAAACAGCTCAAGCACAGCCTGGAGTCTTCCCGCATCTGCGC

```
GGGAGTAGAGTCTG

GCTTTGGGCCCCGCGTACCCCGCAGTCGTCGGGGACCAGTTCGAGGCCACGG

GAAGGGTTTCCGCG

GCAGGGCGCGGAGTAAAGAGGGGAAGAAGGAATCCTCTCCGCGTGATCAGT

AGGGCGGGCTTGTG

ATACTCTCACACCCAGGTTCCAGCTCAGCCCCCAAACTGCTGCCCCAAGAAA

ACAAGTTGGGGAGTG

TGGATTTAGACATAACAACGGGTGTGAGCTGATGTCCTTACAACCAAAAATA

TTGAGACTAGAAATT

CAGCTCCGAATCCACGACCCTCAGATTGATGCTTAATCGCACCCTCGACTCCA

GAAAAGCTGCCGGG

GACAGACATGGACAGGTTTTGCCAAGGGTTCATTAAAATAGTCTGCACTGGA

ATAACCGGGGTGCA

AGAGATCACGTCTTCACTCAGGGCTTTGGGGATCCCCTCGTCGCCCCAGGTCA

GTGGGTGGGGAGG

AGGGCAAACTTCTGTCTTTTGTTTGTGGGTGAGGGATGCGAATTGTGGCAGCA

GCCGAGAAAAGGG

GGGAAATTAATTGCAGCCAATTAATAATTAATCCCCTTTAAACAGCTTTATTA

TCTCTTCTGGGCGACA

GAGATTTGTCTGATAACCCCCTGAAGACCAAATGTCAAGTTTAACCAAATAG

TTATTGCTTTATCAAC

CCGAGTCTG C A A AT AA ATT A AT C AAA AG

6) LI NC00682:6 sequence (ENST00000498940)                    (SEQ. ID NO: 6)

GTCCGCCTTTAGCGATGGTTTGGGAACCCGGGCGCTGGAAAGGCGCGGGTGC

GGAGGGCGGCTGA

GCCGCGCGGCTGCGGCACCGTGGGCGCGAGACCCCTGCGGAGAGGAGCGCG

CGGACGCCGGGGG

AAGCGCCTCGGGGCGGCTGGAGGCGCAGCACCCTGGGGGAGCCGGGGCGCG

GGAGAGACAAAAC

TGTTCGAACCTTCTCTCCCTTCCCCACCCCCAGCGCCCAAACCCGGGGCGGGT

GAGCGCGACCCTTGC

AGCGACCCCTTGCCGAGCCCTGCCCGCGCGATTACTAAGGAGACGCGGCCTC

CGGCACTGCCGTCCC

CGCGCCGTTTGAAAACGGATCCATCAGCGGGGTATTTGGAGATTATTCGCAC

TGAATTTTCTGCCCGC

CAAGAACGAATAGGATTGCCAAGCCACACCACTTTTTGGAGCCCGCTTATTC

GCGCCTATCCACCCTC

TCCTGTGCCCCAGGTTCCCTGAGCACGGGAATCCTTTCCGGGCATGGCCAAGT

TTGTTCGGTGGCTC

AGAGCGGGAAGGGAAGTGCAGTTCGACACCTGTCCAGCTGCTCCGCTTGGAG
```

-continued

```
ATCAAAGGCCGGCT

ATGGGCTGAGCGACAGATTTACGGGACGGTGGTACAGATTAAGGCGAGAAC

CCTGCCGGTCCTGGA

CTCGAGTTCGCACCCAAGGAAAGCGTACAGGTCCCTGGAAGCGGGTGGATGT

CGGAGAGGCCGAG

G C AG CCTG CG CTGTG G CC AGG CAG G CTTGGTG GG CTTTAGTCTC

AGTATGTGTTCTTTAAAGTCTTG

ACAGGTTATTAGTAAAGGAAGGGGCACCCCAGGGTCATGAAGATGCTTCTCG

CTCTGGCCCAAGCAT

GCTGAGGCTCGCTTATTCCTCGGCCAGGCCCAGTAAAACAGCTCAAGCACAG

CCTGGAGTCTTCCCG

CATCTGCGCGGGAGTAGAGTCTGGCTTTGGGCCCCGCGTACCCCGCAGTCGT

CGGGGACCAGTTCG

AGGCCACGGGAAGGGTTTCCGCGGCAGGGCGCGGAGTAAAGAGGGGAAGAA

GGAATCCTCTCCGC

GTGATCAGTAGGGCGGGCTTGTGATACTCTCACACCCAGGTTCCAGCTCAGC

CCCCAAACTGCTGCC

CCAAGAAAACAAGTTGGGGAGTGTGGATTTAGACATAACAACGGGTGTGAG

CTGATGTCCTTACAA

CCAAAAATATTGAGACTAGAAATTCAGCTCCGAATCCACGACCCTCAGATTG

ATGCTTAATCGCACCC

TCGACTCCAGAAAAGCTGCCGGGGACAGACATGGACAGGTTTTGCCAAGGGT

TCATTAAAATAGTCT

GCACTGGAATAACCGGGGTGCAAGAGATCACGTCTTCACTCAGGGCTTTGGG

GATCCCCTCGTCGCC

CCAGGTCAGTGGGTGGGAGGAGGGCAAACTTCTGTCTTTTGTTTGTGGGTG

AGGGATGCGAATTG

TGGCAGCAGCCGAGAAAAGGGGGGAAATTAATTGCAGCCAATTAATAATTA

ATCCCCTTTAAACAGC

TTTATTATCTCTTCTGGGCGACAGAGATTTGTCTGATAACCCCCTGAAGACCA

AATGTCAAGTTTAAC

CAAAT AGTT ATT G CTTT AT CAACCCG AGT
```

7) LI NC00682:7 sequence (SEQ ID NO: 7)

```
GTCCGCCTTTAGCGATGGTTTGGGAACCCGGGCGCTGGAAAGGCGCGGGTGC

GGAGGGCGGCTGA

GCCGCGCGGCTGCGGCACCGTGGGCGCGAGACCCCTGCGGAGAGGAGCGCG

CGGACGCCGGGGG

AAGCGCCTCGGGCGGCTGGAGGCGCAGCACCCTGGGGGAGCCGGGGCGCG

GGAGAGACAAAAC

TGTTCGAACCTTCTCTCCCTTCCCCACCCCCAGCGCCCAAACCCGGGGCGGGT

GAGCGCGACCCTTGC
```

-continued

```
AGCGACCCCTTGCCGAGCCCTGCCCGCGCGATTACTAAGGAGACGCGGCCTC

CGGCACTGCCGTCCC

CGCGCCGTTTGAAAACGGATCCATCAGCGGGGTATTTGGAGATTATTCGCAC

TGAATTTTCTGCCCGC

CAAGAACGAATAGGATTGCCAAGCCACACCACTTTTTGGAGCCCGCTTATTC

GCGCCTATCCACCCTC

TCCTGTGCCCCAGGTTCCCTGAGCACGGGAATCCTTTCCGGGCATGGCCAAGT

TTGTTCGGTGGCTC

AGAGCGGGAAGGGAAGTGCAGTTCGACACCTGTCCAGCTGCTCCGCTTGGAG

ATCAAAGGCCGGCT

ATGGGCTGAGCGACAGATTTACGGGACGGTGGTACAGATTAAGGCGAGAAC

CCTGCCGGTCCTGGA

CTCGAGTTCGCACCCAAGGAAAGCGTACAGGTCCCTGGAAGCGGGTGGATGT

CGGAGAGGCCGAG

G C AG CCTG CG CTGTG G CC AGG CAG G CTTGGTG GG CTTTAGTCTC

AGTATGTGTTCTTTAAAGTCTTG

ACAGGTTATTAGTAAAGGAAGGGGCACCCCAGGGTCATGAAGATGCTTCTCG

CTCTGGCCCAAGCAT

GCTGAGGCTCGCTTATTCCTCGGCCAGGCCCAGTAAAACAGCTCAAGCACAG

CCTGGAGTCTTCCCG

CATCTGCGCGGGAGTAGAGTCTGGCTTTGGGCCCCGCGTACCCCGCAGTCGT

CGGGGACCAGTTCG

AGGCCACGGGAAGGGTTTCCGCGGCAGGGCGCGGAGTAAAGAGGGGAAGAA

GGAATCCTCTCCGC

GTGATCAGTAGGGCGGGCTTGTGATACTCTCACACCCAGGTTCCAGCTCAGC

CCCCAAACTGCTGCC

CCAAGAAAACAAGTTGGGGAGTGTGGATTTAGACATAACAACGGGTGTGAG

CTGATGTCCTTACAA

CCAAAAATATTGAGACTAGAAATTCAGCTCCGAATCCACGACCCTCAGATTG

ATGCTTAATCGCACCC

TCGACTCCAGAAAAGCTGCCGGGGACAGACATGGACAGGTTTTGCCAAGGGT

TCATTAAAATAGTCT

GCACTGGAATAACCGGGGTGCAAGAGATCACGTCTTCACTCAGGGCTTTGGG

GATCCCCTCGTCGCC

CCAGGTCAGTGGGTGGGAGGAGGGCAAACTTCTGTCTTTTGTTTGTGGGTG

AGGGATGCGAATTG

TGGCAGCAGCCGAGAAAAGGGGGGAAATTAATTGCAGCCAATTAATAATTA

ATCCCCTTTAAACAGC

TTTATTATCTCTTCTGGGCGACAGAGATTTGTCTGATAACCCCCTGAAGACCA

AATGTCAAGTTTAAC
```

```
CAAAT AGTT ATT G CTTT AT CAACCCG AGT CT GCAA AT A A ATT A AT C

A A A AG
```

8) LI NC00682:8 sequence (ENST00000637677)

(SEQ ID NO: 8)

```
GAGGGCGCGCGCCGCCCCGCGCTCCCTCCCTCCCCGGTAATTGATGGAGGCT

GCCGAAAAAAGATA ATT AGTTTT AT GT AT AT AAT ATTT GAT C ATG

AAAAT ATT CTTT G CCTT ATTTTGGTAT AG GAG AT CTGT AAT AT AT GTT

AAAAT AGTT AATTTTTT ATT AT CT CTTTGTTT G G CGG CAG CCCG G CCTAT

CCG AAATT A CCG G AG CAT CAACTG AAAAT GT AGG CAAT GT AAG C AAT

GTT AAAT CT AATTTTT CT GT CC AAAACCT A

ATTAGCCATTTTAAAAAAGGTTAACGCCAGCGCCTGAGACGGTTTTTGTTTAA

TAATCCTATTACTGA CG G CT CAT CAT GT AT AAAAT GGTGCAGTAGGATG

C A A A ATTT CC ACTTGTTT ATAAGTGTATCGCCGA GAAATGTAT AAAAT

AATCGAGACCGGCGGAGGCAGGTCAGAGCCGTCTGGAATGCGCGCACCTTCA

ACGAACAATGCCAACATTGAAGTCCTCGGTTGGAGTCTGCACAGTTGGAGAT

CTTTGGTGCCATTTTA

GACATCTTTGGATTTCATCAATCAAACTGACTGCAATTTTCCATAAAAACCCT

GAATTTGGGTCAGAA AGTG GG CAAAGTAG AT AAAG AT CATT CG AG CT GT

CTT AT AAG ATG AT AAAT AG AT ATCCTTT CAG G C

CAACAATGCCAAAGTGCAGTTTTGTGATTCCCTTCCATGGGTTCTGAATGCAG

TGAGTCGAAACGATT

TCTACATGTTTTCCCATGGTTTAGGAGGTGTCTTTACATACTTGTCAATAGTA

GCCTGACCTTTTTCCC

CATGGAGTTGCTAAGTGTGTTTTGTTTGTTGCTTTGAGTACTTTTTTCTTGTTG

TTTGTGTGTGTGTTG CACAAAAT ACAC AAG AAAAT AAAGGTTTTTTTT

CTTTT ATT G CT C AAA
```

9) LI NC00682:9 sequence (SEQ ID NO: 9)

```
ACTTGTTT AT AAGTGTATCGCCGAGAAATGTAT AAAAT

AATCGAGACCGGCGGAGGCAGGTCAGAG

CCGTCTGGAATGCGCGCACCTTCAACGAACAATGCCAACATTGAAGTCCTCG

GTTGGAGTCTGCACA

GTTGGAGATCTTTGGTGCCATTTTAGACATCTTTGGATTTCATCAATCAAACT

GACTGCAATTTTCCAT

AAAAACCCTGAATTTGGGTCAGAAAGTGGGCAAAGTAGATAAAGATCATTCG

AGCTGTCTTATAAGA

TGATAAATAGATATCCTTTCAGGCCAACAATGCCAAAGTGCAGTTTTGTGATT

CCCTTCCATGGGTTC

TGAATGCAGTGAGTCGAAACGATTTCTACATGTTTTCCCATGGTTTAGGAGGT

GTCTTTACATACTTG

TCAATAGTAGCCTGACCTTTTTCCCCATGGAGTTGCTAAGTGTGTTTTGTTTGT

TGCTTTGAGTACTTT

TTT CTTGTT GTTTGTGT GTGTGTTG CACAAAAT ACAC AAG AAAAT
```

```
AAAGGTTTTTTTT CTTTT ATT G CTC

AAATCAATAGGATATGGGTCTGATCTAGATAATTCTCTGCATATAGACTGGTT

TCAGTAGCCCTTGAG

TTCATGTAGAAATTCCATTTGCTCTGCAGTTGCTCTTGAGGCACTTTGGACAC

CATTTTGGGCACCATG

CTGGGATGTAAACTCACTTTCTTAACAACAACAACAACAACAAC
```

10) LI NC00682:10 sequence (ENST00000504870)  (SEQ ID NO: 10)

```
ACTTGTTTATAAGTGTATCGCCGAGAAATGTATAAAATAATCGAGACCGGCG

GAGGCAGGTCAGAG

CCGTCTGGAATGCGCGCACCTTCAACCACTTTGGGAGGCCGAGGCAGGTGGA

TCACCTCAGGTCAG

GAGTTCGAGACCAGCGTGACCAACATGGTGAAACCCGTCTCTACTAAAAATA

CAAAAAATTAGATGG

GTATGGTGGCGCGTGCCTGTCTGCTACTCGGGAGGCTGAGGCAGGAGAACCT

TGGAGGCAAAGGTT

GCAGTG AGCTG AG ATCAAG CCACCG CACTCCAG CCTGGG CG ACAG CG

CAAA ACTTT GT CT CAAAAAA

AAAAAAAAAAAAAAGT CCG CAGTATGGTTTT CAC ATT AT C ACT CT CAAT

G CC ATT G G AG GTAGGTCC

AAGCTGGTGTCTCTTTGATTAGTCTCCCTAAACCCATCTATTCATTTACTAGCC

ATTAGTTATTCTTTAA

TTGAGTCCAAAAATGTTTGTGAGGAGATAGTCCCATATGAGATTAAAAGAAA

GAAAGAAAACAAAA

CAACAAACAAACAAACAAAACAGAAAATCAGGTGTAGTGGACACTGAAGAG

TTTCTG
```

11) LI NC00682:11 sequence (ENST00000499082)  (SEQ ID NO: 11)

```
ACTTGTTTATAAGTGTATCGCCGAGAAATGTATAAAATAATCGAGACCGGCG

GAGGCAGGTCAGAG

CCGTCTGGAATGCGCGCACCTTCAACGGTATTTGGAGATTATTCGCACTGAAT

TTTCTGCCCGCCAAG

AACGAATAGGATTGCCAAGCCACACCACTTTTTGGAGCCCGCTTATTCGCGC

CTATCCACCCTCTCCT

GTGCCCCAGGTTCCCTGAGCACGGGAATCCTTTCCGGGCATGGCCAAGTTTGT

TCGGTGGCTCAGAG

CGGGAAGGGAAGTGCAGTTCGACACCTGTCCAGCTGCTCCGCTTGGAGATCA

AAGGCCGGCTATGG

GCTGAGCGACAGATTTACGGGACGGTGGTACAGATTAAGGCGAGAACCCTGC

CGGTCCTGGACTCG

AGTTCGCACCCAAGGAAAGCGTACAGGTCCCTGGAAGCGGGTGGATGTCGGA

GAGGCCGAGGCAG
```

-continued

```
CCTGCGCTGTGGCCAGGCAGGCTTGGTGGGCTTTAGTCTCAGTATGTGTTCTT

TAAAGTCTTGACAG

GTTATTAGTAAAGGAAGGGGCACCCCAGGGTCATGAAGATGCTTCTCGCTCT

GGCCCAAGCATGCTG

AGGCTCGCTTATTCCTCGGCCAGGCCCAGTAAAACAGCTCAAGCACAGCCTG

GAGTCTTCCCGCATCT

GCGCGGGAGTAGAGTCTGGCTTTGGGCCCCGCGTACCCCGCAGTCGTCGGGG

ACCAGTTCGAGGCC

ACGGGAAGGGTTTCCGCGGCAGGGCGCGGAGTAAAGAGGGGAAGAAGGAAT

CCTCTCCGCGTGAT

CAGTAGGGCGGGCTTGTGATACTCTCACACCCAGGTTCCAGCTCAGCCCCCA

AACTGCTGCCCCAAG

AAAACAAGTTGGGGAGTGTGGATTTAGACATAACAACGGGTGTGAGCTGATG

TCCTTACAACCAAA

AATATTGAGACTAGAAATTCAGCTCCGAATCCACGACCCTCAGATTGATGCTT

AATCGCACCCTCGAC

TCCAGAAAAGCTGCCGGGGACAGACATGGACAGGTTTTGCCAAGGGTTCATT

AAAATAGTCTGCACT

GGAATAACCGGGGTGCAAGAGATCACGTCTTCACTCAGGGCTTTGGGGATCC

CCTCGTCGCCCCAGG

TCAGTGGGTGGGGAGGAGGGCAAACTTCTGTCTTTTGTTTGTGGGTGAGGGA

TGCGAATTGTGGCA

GCAGCCGAGAAAAGGGGGGAAATTAATTGCAGCCAATTAATAATTAATCCCC

TTTAAACAGCTTTAT

TATCTCTTCTGGGCGACAGAGATTTGTCTGATAACCCCCTGAAGACCAAATGT

CAAGTTTAACCAAAT

AGTT ATT G CTTT AT C AACCCG AGT CT G C AAAT AAATT AAT C AAAAG C

AAA

12) LI NC00682:12 sequence
                                                        (SEQ ID NO: 12)
TCATCATGTATAAAATGGTGCAGTAGGATGCAAAATTTCCACTTGTTTATAAG

TGTATCGCCGAGAAA

TGTATAAAATAATCGAGACCGGCGGAGGCAGGTCAGAGCCGTCTGGAATGCG

CGCACCTTCAACGG

TATTTGGAGATTATTCGCACTGAATTTTCTGCCCGCCAAGAACGAATAGGATT

GCCAAGCCACACCAC

TTTTTGGAGCCCGCTTATTCGCGCCTATCCACCCTCTCCTGTGCCCCAGGTTCC

CTGAGCACGGGAAT

CCTTTCCGGGCATGGCCAAGTTTGTTCGGTGGCTCAGAGCGGGAAGGGAAGT

GCAGTTCGACACCT

GTCCAGCTGCTCCGCTTGGAGATCAAAGGCCGGCTATGGGCTGAGCGACAGA

TTTACGGGACGGTG
```

-continued

```
GTACAGATTAAGGCGAGAACCCTGCCGGTCCTGGACTCGAGTTCGCACCCAA

GGAAAGCGTACAGG

TCCCTGGAAGCGGGTGGATGTCGGAGAGGCCGAGGCAGCCTGCGCTGTGGCC

AGGCAGGCTTGGT

GGGCTTTAGTCTCAGTATGTGTTCTTTAAAGTCTTGACAGGTTATTAGTAAAG

GAAGGGGCACCCCA

GGGTCATGAAGATGCTTCTCGCTCTGGCCCAAGCATGCTGAGGCTCGCTTATT

CCTCGGCCAGGCCC

AGTAAAACAGCTCAAGCACAGCCTGGAGTCTTCCCGCATCTGCGCGGGAGTA

GAGTCTGGCTTTGG

GCCCCGCGTACCCCGCAGTCGTCGGGGACCAGTTCGAGGCCACGGGAAGGGT

TTCCGCGGCAGGGC

GCGGAGTAAAGAGGGGAAGAAGGAATCCTCTCCGCGTGATCAGTAGGGCGG

GCTTGTGATACTCTC

ACACCCAGGTTCCAGCTCAGCCCCCAAACTGCTGCCCCAAGAAAACAAGTTG

GGGAGTGTGGATTTA

G ACAT AACAACGG GT GT GAG CT GAT GT CCTT ACAACCAAAAT ATT GAG

ACT AG AAATT CAG CTCCG

AATCCACGACCCTCAGATTGATGCTTAATCGCACCCTCGACTCCAGAAAAGC

TGCCGGGGACAGACA

TGGACAGGTTTTGCCAAGGGTTCATTAAAATAGTCTGCACTGGAATAACCGG

GGTGCAAGAGATCAC

GTCTTCACTCAGGGCTTTGGGGATCCCCTCGTCGCCCCAGGTCAGTGGGTGGG

GAGGAGGGCAAAC

TTCTGTCTTTTGTTTGTGGGTGAGGGATGCGAATTGTGGCAGCAGCCGAGAAA

AGGGGGGAAATTA

ATTG CAG CCAATT AATAATT AATCCCCTTT AAA CAG CTTT ATT AT CT CTT

CTGGGCGACAG AG ATTT GT

CTGATAACCCCCTGAAGACCAAATGTCAAGTTTAACCAAATAGTTATTGCTTT

ATCAACCCGAGTCTG

C A A AT AAATT A AT C A A A AG CAAA
```

Note that, for all sequences, unless specifically mentioned otherwise, the term 'LINC00682' encompasses the 12 different isoforms or splice variants.

With "functional expression" of LINC00682, it is meant the transcription and/or translation of functional gene product. For non-protein coding genes like LINC00682, "functional expression" can be deregulated on at least two levels. First, at the DNA level, e.g., by absence or disruption of the gene, or lack of transcription taking place (in both instances preventing synthesis of the relevant gene product). The lack of transcription can e.g., be caused by epigenetic changes (e.g., DNA methylation) or by loss of function mutations. A "loss-of-function" or "LOF" mutation as used herein is a mutation that prevents, reduces or abolishes the function of a gene product as opposed to a gain-of-function mutation that confers enhanced or new activity on a gene product. LOF can be caused by a wide range of mutation types, including, but not limited to, a deletion of the entire gene or part of the gene, splice site mutations, frame-shift mutations caused by small insertions and deletions, nonsense mutations and mutations preventing correct cellular localization of the product. Also included within this definition are mutations in promoters or regulatory regions of the LINC00682 gene if these interfere with gene function. A null mutation is an LOF mutation that completely abolishes the function of the gene product. A null mutation in one allele will typically reduce expression levels by 50%, but may have severe effects on the function of the gene product. Note that functional expression can also be deregulated because of a gain of function mutation: by conferring a new activity on the lncRNA the normal function of the lncRNA is deregulated, and less functionally lncRNA is expressed. Vice versa, functional expression can be increased e.g., through gene duplication or by lack of DNA methylation. Second, at the RNA level, e.g., by lack of efficient translation taking place—e.g., because of destabilization of the lncRNA so that it is degraded. Or by lack of efficient transcription, e.g., because a mutation introduces a new splicing variant.

"Long non-coding RNAs" (long ncRNAs, lncRNA) as used herein are non-protein coding transcripts longer than 200 nucleotides. A particular class of lncRNA are long intergenic ncRNAs (lincRNA), referring to long non-coding RNAs that are transcribed from non-coding DNA sequences between protein-coding genes.

The present application discloses specific expression of lncRNAs in neuroblastoma, and that inhibition of such lncRNA can be used to selectively induce apoptosis in these cancer cells or reduce their growth.

Accordingly, provided are inhibitors of functional expression of the LINC00682 gene. Such inhibitors can act at the DNA level, or at the RNA (i.e., gene product) level. As LINC00628 is a non-coding gene, there is no protein product for this gene. If inhibition is to be achieved at the DNA level, this may be done using gene therapy to knock-out or disrupt the target gene. As used herein, a "knock-out" can be a gene knockdown or the gene can be knocked out by a mutation such as, a point mutation, an insertion, a deletion, by techniques known in the art, including, but not limited to, retroviral gene transfer. Another way in which genes can be knocked out is by the use of zinc finger nucleases. Zinc finger nucleases (ZFNs) are artificial restriction enzymes generated by fusing a zinc finger DNA-binding domain to a DNA-cleavage domain. Zinc finger domains can be engineered to target desired DNA sequences, which enable zinc-finger nucleases to target unique sequence within a complex genome. By taking advantage of endogenous DNA repair machinery, these reagents can be used to precisely alter the genomes of higher organisms. Other technologies for genome customization that can be used to knock out genes are meganucleases and TAL effector nucleases (TALENs, Cellectis bioresearch). A TALEN® is composed of a TALE DNA binding domain for sequence-specific recognition fused to the catalytic domain of an endonuclease that introduces double strand breaks (DSB). The DNA binding 5 domain of a TALEN® is capable of targeting with high precision a large recognition site (for instance, 17 bp). Meganucleases are sequence-specific endonucleases, naturally occurring "DNA scissors," originating from a variety of single-celled organisms such as bacteria, yeast, algae and some plant organelles. Meganucleases have long recognition sites of between 12 and 30 base pairs. The recognition site of natural meganucleases can be modified in order to target native genomic DNA sequences (such as endogenous genes). Another recent genome editing technology is the CRISPR/Cas system, which can be used to achieve RNA-guided genome engineering. CRISPR interference is a genetic technique, which allows for sequence-specific control of gene expression in prokaryotic and eukaryotic cells while CRISPR-Casl3a enables direct cleavage of RNA molecules. It is based on the bacterial immune system-derived CRISPR (clustered regularly interspaced palindromic repeats) pathway. Gene inactivation, i.e., inhibition of functional expression of the gene, may, for instance, also be achieved through the creation of transgenic organisms expressing antisense RNA, or by administering antisense RNA to the subject. An antisense construct can be delivered, for example, as an expression plasmid, which, when transcribed in the cell, produces RNA that is complementary to at least a unique portion of the cellular LINC00682 lncRNA.

A more rapid method for the inhibition of gene expression is based on the use of shorter antisense oligomers consisting of DNA, or other synthetic structural types such as phosphorothiates, 2'-0-alkylribonucleotide chimeras, locked nucleic acid (LNA), peptide nucleic acid (PNA), or morpholinos.

With the exception of RNA oligomers, PNAs and morpholinos, all other antisense oligomers act in eukaryotic cells through the mechanism of RNase H-mediated target cleavage. PNAs and morpholinos bind complementary DNA and RNA targets with high affinity and specificity, and thus act through a simple steric blockade of the RNA translational machinery, and appear to be completely resistant to nuclease attack. An "antisense oligomer" refers to an anti-sense molecule or anti-gene agent that comprises an oligomer of at least about 10 nucleotides in length. In embodiments an antisense oligomer comprises at least 15, 18, 20, 25, 30, 35, 40, or 50 nucleotides. Antisense approaches involve the design of oligonucleotides (either DNA or RNA, or derivatives thereof) that are complementary to an RNA encoded by polynucleotide sequences of LINC00682. Antisense RNA may be introduced into a cell to inhibit translation of a complementary mRNA by base pairing to it and physically obstructing the translation machinery. This effect is therefore stoichiometric. Absolute complementarity, although preferred, is not required. A sequence "complementary" to a portion of an RNA, as referred to herein, means a sequence having sufficient complementarity to be able to hybridize with the RNA, forming a stable duplex; in the case of double stranded antisense polynucleotide sequences, a single strand of the duplex DNA may thus be tested, or triplex formation may be assayed. The ability to hybridize will depend on both the degree of complementarity and the length of the antisense polynucleotide sequence. Generally, the longer the hybridizing polynucleotide sequence, the more base mismatches with an RNA it may contain and still form a stable duplex (or triplex, as the case may be). One skilled in the art can ascertain a tolerable degree of mismatch by use of standard procedures to determine the melting point of the hybridized complex.

Antisense oligomers should beat least 10 nucleotides in length, and are preferably oligomers ranging from 15 to about 50 nucleotides in length. In certain embodiments, the oligomer is at least 15 nucleotides, at least 18 nucleotides, at least 20 nucleotides, at least 25 nucleotides, at least 30 nucleotides, at least 35 nucleotides, at least 40 nucleotides, or at least 50 nucleotides in length. A related method uses ribozymes instead of antisense RNA. Ribozymes are catalytic RNA molecules with enzyme-like cleavage properties that can be designed to target specific RNA sequences. Successful target gene inactivation, including temporally and tissue-specific gene inactivation, using ribozymes has been reported in mouse, zebrafish and fruit flies. RNA interference (RNAi) is a form of post-transcriptional gene silencing. The phenomenon of RNA interference was first observed and described in *Caenorhabditis elegans* where exogenous double stranded RNA (dsRNA) was shown to specifically and potently disrupt the activity of genes containing homologous sequences through a mechanism that induces rapid degradation of the target RNA. Several reports describe the same catalytic phenomenon in other organisms, including experiments demonstrating spatial and/or temporal control of gene inactivation, including plant (*Arabidopsis thaliana*), protozoan (*Trypanosoma bruceii*), invertebrate (*Drosophila melanogaster*), and vertebrate species (*Danio* rerio and *Xenopus laevis*). The mediators of sequence-specific messenger RNA degradation are small interfering RNAs (siRNAs) generated by ribonuclease III cleavage from longer dsRNAs. Generally, the length of siRNAs is between 20-25 nucleotides (Elbashir et al. (2001) Nature 411, 494 498). The siRNA typically comprises of a sense RNA strand and a complementary antisense RNA strand annealed together by standard Watson Crick base pairing interactions (hereinafter "base paired"). The sense strand comprises a nucleic acid sequence that is identical to a target sequence contained within the target mRNA. The sense and antisense strands of the present siRNA can comprise two complementary, single stranded RNA molecules or can comprise a single molecule in which two complementary portions are base paired and are covalently linked by a single stranded "hairpin" area (often referred to as shRNA). The term "isolated" means altered or removed from the natural state through human intervention. For example, an siRNA naturally present in a living animal is not "isolated," but a synthetic siRNA, or an siRNA partially or completely separated from the coexisting materials of its natural state is "isolated." An isolated siRNA can exist in substantially purified form, or can exist in a non-native environment such as, for example, a cell into which the siRNA has been delivered. The siRNAs of the disclosure can comprise partially purified RNA, substantially pure RNA, synthetic RNA, or recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siRNA or to one or more internal nucleotides of the siRNA, including modifications that make the siRNA resistant to nuclease digestion. One or both strands of the siRNA of the disclosure can also comprise a 3' overhang. A "3' overhang" refers to at least one unpaired nucleotide extending from the 3' end of an RNA strand. Thus, in one embodiment, the siRNA of the disclosure comprises at least one 3' overhang of from one to about six nucleotides (which includes ribonucleotides or deoxynucleotides) in length, preferably from one to about five nucleotides in length, more preferably from one to about four nucleotides in length, and particularly preferably from about one to about four nucleotides in length. In the embodiment in which both strands of the siRNA molecule comprise a 3' overhang, the length of the overhangs can be the same or different for each strand. In a most preferred embodiment, the 3' overhang is present on both strands of the siRNA, and is two nucleotides in length. In order to enhance the stability of the present siRNAs, the 3' overhangs can also be stabilized against degradation. In one embodiment, the overhangs are stabilized by including purine nucleotides, such as adenosine or guanosine nucleotides. Alternatively, substitution of pyrimidine nucleotides by modified analogues, e.g., substitution of uridine nucleotides in the 3' overhangs with 2' deoxythymidine, is tolerated and does not affect the efficiency of RNAi degradation. In particular, the absence of a 2' hydroxyl in the 2' deoxythymidine significantly enhances the nuclease resistance of the 3' overhang in tissue culture medium. The siRNAs of the disclosure can be targeted to any stretch of approximately 19 to 25 contiguous nucleotides in any of the target LINC00682 RNA sequences (the "target sequence"), of which examples are given in the application. Techniques for selecting target sequences for siRNA are well known in the art. Thus, the sense strand of the present siRNA comprises a nucleotide sequence identical to any contiguous stretch of about 19 to about 25 nucleotides in the target mRNA. The siRNAs of the disclosure can be obtained using a number of techniques known to those of skill in the art. For example, the siRNAs can be chemically synthesized or recombinantly produced using methods known in the art. Preferably, the siRNA of the disclosure are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Alternatively, siRNA can also be expressed from recombinant circular or linear DNA plasmids using any suitable promoter. Suitable promoters for expressing siRNA of the disclosure from a plasmid include, for example, the U6 or HI RNA pol III promoter sequences and the cytomegalovirus promoter. Selection of other suitable promoters is within the skill in the art. The recombinant plasmids of the disclosure can also comprise inducible or regulatable promoters for expression of the siRNA in a particular tissue or in a particular intracellular environment. The siRNA expressed from recombinant plasmids can either be isolated from cultured cell expression systems by standard techniques, or can be expressed intracellularly, e.g., in breast tissue or in neurons. The siRNAs of the disclosure can also be expressed intracellularly from recombinant viral vectors. The recombinant viral vectors comprise sequences encoding the siRNAs of the disclosure and any suitable promoter for expressing the siRNA sequences. Suitable promoters include, for example, the U6 or HI RNA pol III promoter sequences and the cytomegalovirus promoter. Selection of other suitable promoters is within the skill in the art. The recombinant viral vectors of the disclosure can also comprise inducible or regulatable promoters for expression of the siRNA in the tissue where the tumor is localized. As used herein, an "effective amount" of the siRNA is an amount sufficient to cause RNAi mediated degradation of the target mRNA, or an amount sufficient to inhibit the progression of metastasis in a subject. RNAi mediated degradation of the target mRNA can be detected by measuring levels of the target mRNA or protein in the cells of a subject, using standard techniques for isolating and quantifying mRNA or protein as described above.

One skilled in the art can readily determine an effective amount of the siRNA of the disclosure to be administered to a given subject, by taking into account factors such as the size and weight of the subject; the extent of the disease penetration; the age, health and sex of the subject; the route of administration; and whether the administration is regional or systemic. Generally, an effective amount of the siRNA of the disclosure comprises an intracellular concentration of from about 1 nanomolar (nM) to about 100 nM, preferably from about 2 nM to about 50 nM, more preferably from about 2.5 nM to about 10 nM. It is contemplated that greater or lesser amounts of siRNA can be administered. Recently it has been shown that morpholino antisense oligonucleotides in zebrafish and frogs overcome the limitations of RNase H-competent antisense oligonucleotides, which include numerous non-specific effects due to the non-target-specific cleavage of other mRNA molecules caused by the low stringency requirements of RNase H. Morpholino oligomers therefore represent an important new class of antisense molecule. Oligomers of the disclosure may be synthesized by standard methods known in the art. As examples, phosphorothioate oligomers may be synthesized by the method of Stein et al. (1988) Nucleic Acids Res. 16, 3209 3021), methylphosphonate oligomers can be prepared by use of controlled pore glass polymer supports (Sarin et al. (1988) Proc. Natl. Acad. Sci. USA. 85, 7448-7451). Morpholino oligomers may be synthesized by the method of Summerton and Weller U.S. Pat. Nos. 5,217,866 and 5,185,444. Another particularly form of antisense RNA strategy are gapmers. A gapmer is a chimeric antisense oligonucleotide that contains a central block of deoxynucleotide monomers sufficiently long to induce RNase H cleavage. The central block of a gapmer is flanked by blocks of 2'-0 modified ribonucleotides or other artificially modified ribonucleotide monomers such as bridged nucleic acids (BNAs) that protect the internal block from nuclease degradation. Gapmers have been used to obtain RNase-H mediated cleavage of target RNAs, while reducing the number of phosphorothioate linkages. Phosphorothioates possess increased resistance to nucleases compared to unmodified DNA.

However, they have several disadvantages. These include low binding capacity to complementary nucleic acids and non-specific binding to proteins that cause toxic side-effects limiting their applications. The occurrence of toxic side-effects together with non-specific binding causing off-target effects has stimulated the design of new artificial nucleic acids for the development of modified oligonucleotides that provide efficient and specific antisense activity in vivo without exhibiting toxic side-effects. By recruiting RNase H, gapmers selectively cleave the targeted oligonucleotide strand. The cleavage of this strand initiates an antisense effect. This approach has proven to be a powerful method in the inhibition of gene functions and is emerging as a popular approach for antisense therapeutics. Gapmers are offered commercially, e.g., LNA longRNA GapmeRs by Exiqon, or MOE gapmers and cET gapmers by IONIS pharmaceuticals. MOE gapmers or "2'MOE gapmers" are an antisense phosphorothioate oligonucleotide of 15-30 nucleotides wherein all of the backbone linkages are modified by adding a sulfur at the non-bridging oxygen (phosphorothioate) and a stretch of at least 10 consecutive nucleotides remain unmodified (deoxy sugars) and the remaining nucleotides contain an O'-methyl O'-ethyl substitution at the 2' position (MOE). According to a further aspect, the inhibitors of functional expression of LINC00682 are provided for use as a medicament. According to yet further aspects, the inhibitors of functional expression of LINC00682 are provided for use in treatment of cancer, in particular, neuroblastoma. In still further embodiments, the inhibitors are provided for use in treatment of neuroblastoma.

This is equivalent to saying that methods of treating neuroblastoma in a subject in need thereof are provided, comprising administering an inhibitor of functional expression of LINC00682 to the subject.

The nature of the inhibitor is not vital to the disclosure, as long as it inhibits the functional expression of the LINC00682 gene. According to specific embodiments, the inhibitor is selected from an inhibitory RNA technology (such as an antisense oligomer, a gapmer, a shRNA, a siRNA), a CRISPR, a TALEN, or a Zinc-finger nuclease.

According to alternative, but not exclusive, specific embodiments, the inhibitor selectively induces apoptosis in neuroblastoma cells. This particularly implies that it induces apoptosis in neuroblastoma cells, but not in normal (non-transformed) neurons.

According to a further aspect, methods are provided that may identify whether a tumor is suitable for treatment with an inhibitor of functional expression of LINC00682. These methods typically have the following steps:

Determining whether the tumor expresses LINC00682 or whether expression of LINC00682 is increased in the tumor or a sample of tumor cells;

Establishing whether the tumor is suitable for treatment, wherein expression or wherein increased expression is indicative of suitability for treatment.

The methods thus may entail a first step of providing a sample of tumor cells. The determining step may occur purely in vitro, i.e., without a step interacting on the human or animal body.

According to particular embodiments, the tumor is neuroblastoma.

Increased levels of LINC00682 gene product (i.e., typically lncRNA) are typically increased versus a control. The skilled person is capable of picking the most relevant control. This will typically also depend on the nature of the disease studied, the sample(s) that is/are available, and so on. Suitable controls include, but are not limited to, similar samples from subjects not having a tumor, the average levels in a control group (or control cells, e.g., neurons), or a set of clinical data on average LINC00682 gene product levels in the tissue from which the sample is taken. As is evident from the foregoing, the control may be from the same subject, or from one or more different subjects or derived from clinical data.

Optionally, the control is matched for e.g., sex, age etc.

With 'increased' levels of LINC00682 gene product as mentioned herein, it is meant levels that are higher than are normally present. Typically, this can be assessed by comparing to control. According to particular embodiments, increased levels of LINC00682 are levels that are 10%, 20%, 25%, 30%, 40%, 50%, 60%, 70%, 75%, 80%, 90%, 100%, 150%, 200% or even more high than those of the control. It should be noted however that the levels of LINC00682 gene can—but should not—be increased in order to establish whether the tumor is suitable for treatment. Expression as such—but not necessarily increased expression—of the gene could be sufficient to establish whether the tumor is suitable for treatment.

According to further particular embodiments, it means that LINC00682 gene product is expressed or present, whereas it normally (or in control) is absent. In other words, in these embodiments determining the increased expression of LINC00682 gene product is equivalent to detecting the presence of LINC00682 gene product. Typically, in such cases, a control will be included to make sure the detection reaction worked properly. The skilled person will appreciate that the exact levels by which LINC00682 gene product needs to be higher in order to allow a reliable and reproducible diagnosis may depend on the type of sample tested and of which product (lncRNA) the levels are assessed. However, assessing the correlation itself is fairly straightforward.

Instead of looking at increased levels compared to a healthy control, the skilled person will appreciate that the reverse, comparing to a control with disease, can also be done. Thus, if the LINC00682 gene product levels measured in the sample are similar to those of a sample with a tumor (neuroblastoma), (or are e.g., comparable to LINC00682 gene product levels found in a clinical data set of cancer patients), this may be considered equivalent to increased LINC00682 gene product levels compared to a healthy control, and be correlated to an increased suitability of treatment. Of course, LINC00682 gene product levels may be compared to both a negative and a positive control in order to increase accuracy of the diagnosis.

According to specific embodiments, when it is established that the tumor is suitable for treatment, the methods may further comprise a step of administering an inhibitor of functional expression of LINC00682 to the subject in which the tumor is present. This in order to treat the tumor.

Also provided herein are methods of diagnosing the presence of neuroblastoma in a subject, comprising the steps of:
Determining the levels of LINC00682 (or LINC00682 gene product) in a sample of the subject;
Correlating the levels of LINC00682 in the sample with the presence of neuroblastoma.

In such methods, the presence (or increased expression) of LINC00682 is indicative of the presence of neuroblastoma in the subject from whom the sample is taken. Typically, these methods are performed in vitro, although in vivo methods are not necessarily excluded. Determining the levels of LINC00682 will typically be done by determining the levels of LINC00682 RNA in the sample. The same considerations regarding samples and controls apply as described above. The sample can be a tissue sample (e.g., a tumor biopt).

The levels of LINC00682 RNA vary with different stages of the disease. Accordingly, in methods that determine the presence of neuroblastoma, a further step may be included that correlates the levels of LINC00682 to disease severity, disease stage (e.g., stage of neuroblastoma), or disease progression.

It is to be understood that although particular embodiments, specific configurations as well as materials and/or molecules, have been discussed herein for cells and methods according to the disclosure, various changes or modifications in form and detail may be made without departing from the scope and spirit of this disclosure. The following Examples are provided to better illustrate particular embodiments, and they should not be considered limiting the application.

EXAMPLES

Figure 1C:
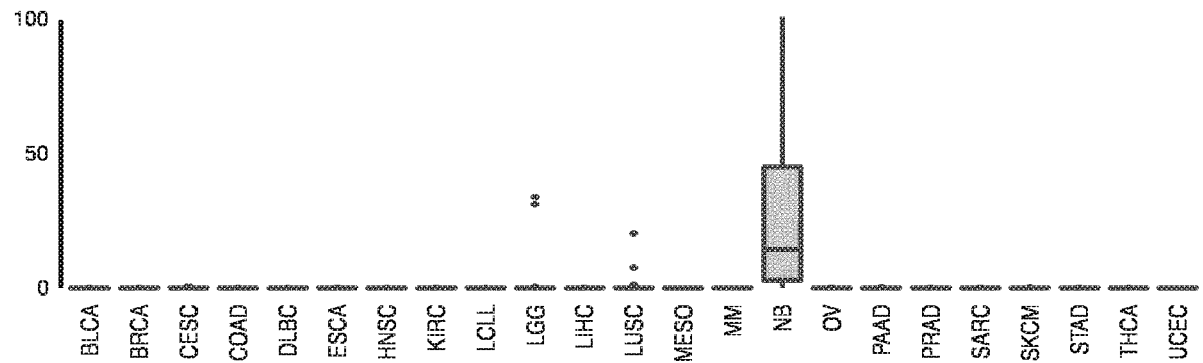
Figure 1D:
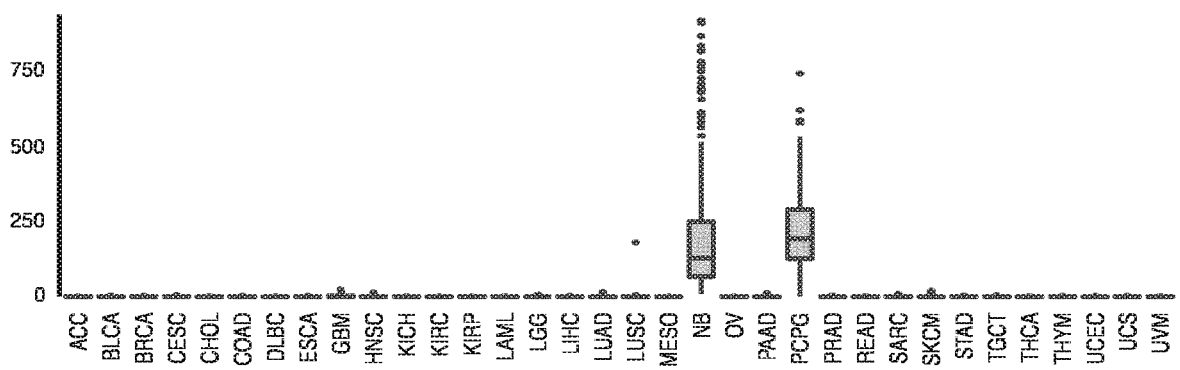

Example 1 (FIG. 1)

Jensen-Shannon Score

To calculate tissue specificity, a score was applied based on the Jensen-Shannon divergence metric, devised by Cabili et al. Using this score, expression patterns of all transcripts are compared to predefined expression levels, representing the situation in which the transcript is expressed in a single tissue. Using the RNA-seq data in the Cancer Cell Line Encyclopedia (CCLE), expression patterns from all transcripts could be compared to the predefined matrix, where the maximum score of a certain transcript defines the tissue specificity.

Visualization of Specificity

Using the CCLE and The Cancer Genome Atlas (TCGA) RNA-seq data repositories, expression levels of the lncRNA were visualized after TPM normalization.

Figure 2A:
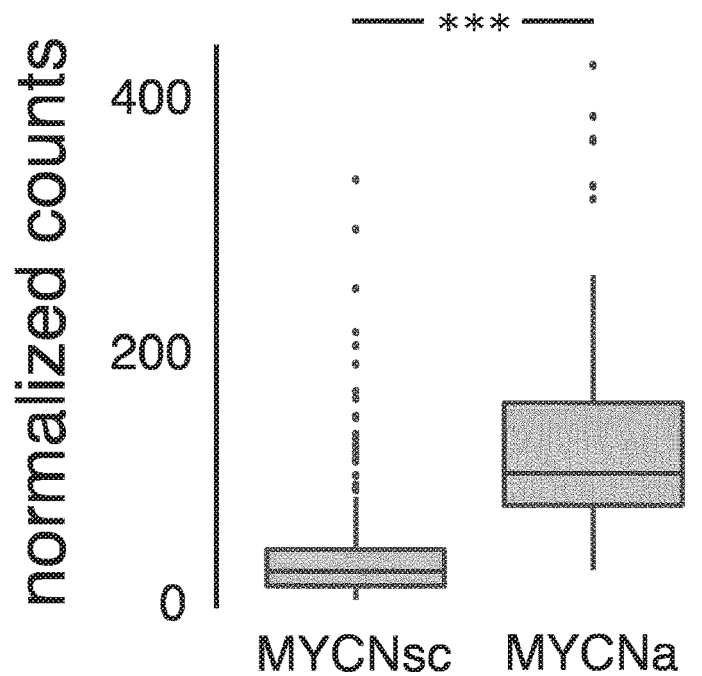
FIG. 2: Boxplot of the expression of lnc-PHOX2B-2 in the different neuroblastoma subgroups, MYCN single copy and MYCN amplified (FIG. 2a) and the different risk groups (FIG. 2b), based on RNA-seq data from 497 primary NB tumor samples.
Figure 2B:
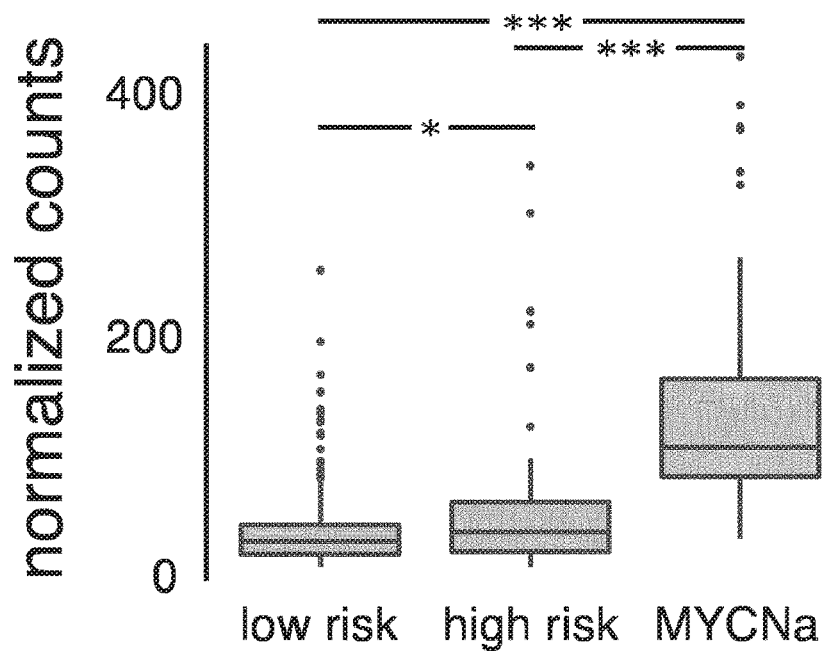

Example 2 (FIG. 2)

RNA-seq data of 497 fully annotated primary tumor samples was used to assess correlation of lnc-PHOX2B-2 expression level and several important clinical parameters. Differential gene expression analysis was performed using limma voom.

Figure 3:
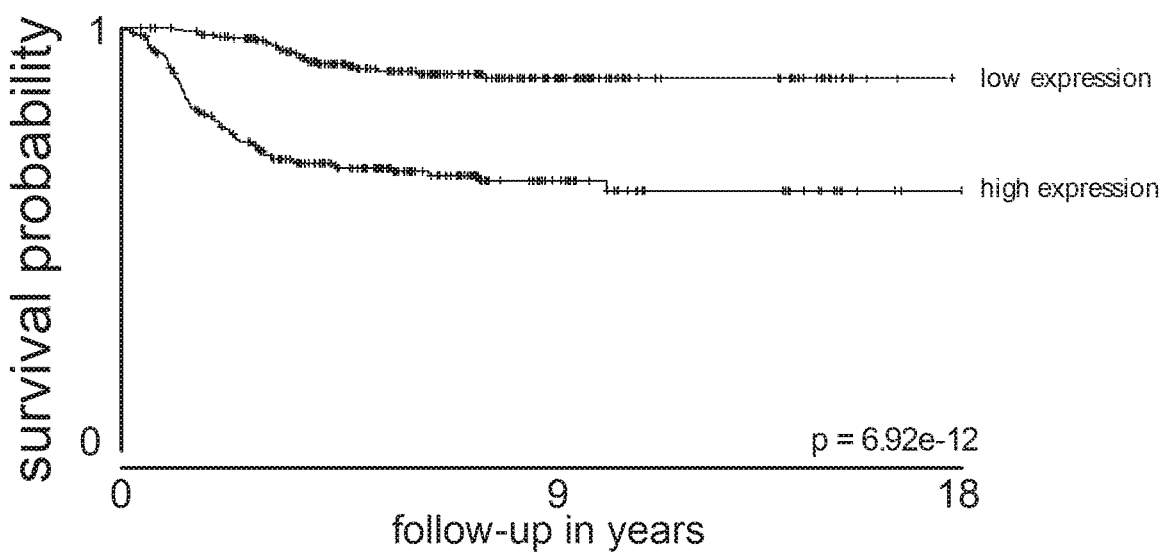
FIG. 3: Kaplan-Meier plot showing that higher expression of lnc-PHOX2B-2 correlates with a lower overall survival probability.

Example 3 (FIG. 3)

Overall survival is shown using a Kaplan-Meier curve. The two groups were formed based on the median expression value: the high lnc-PHOX2B-2 expression group consists of samples with a higher expression level than the median, the low lnc-PHOX2B-2 expression group contains expression levels lower than the median. Significance was calculated using the Chi Square test.

Figure 4:
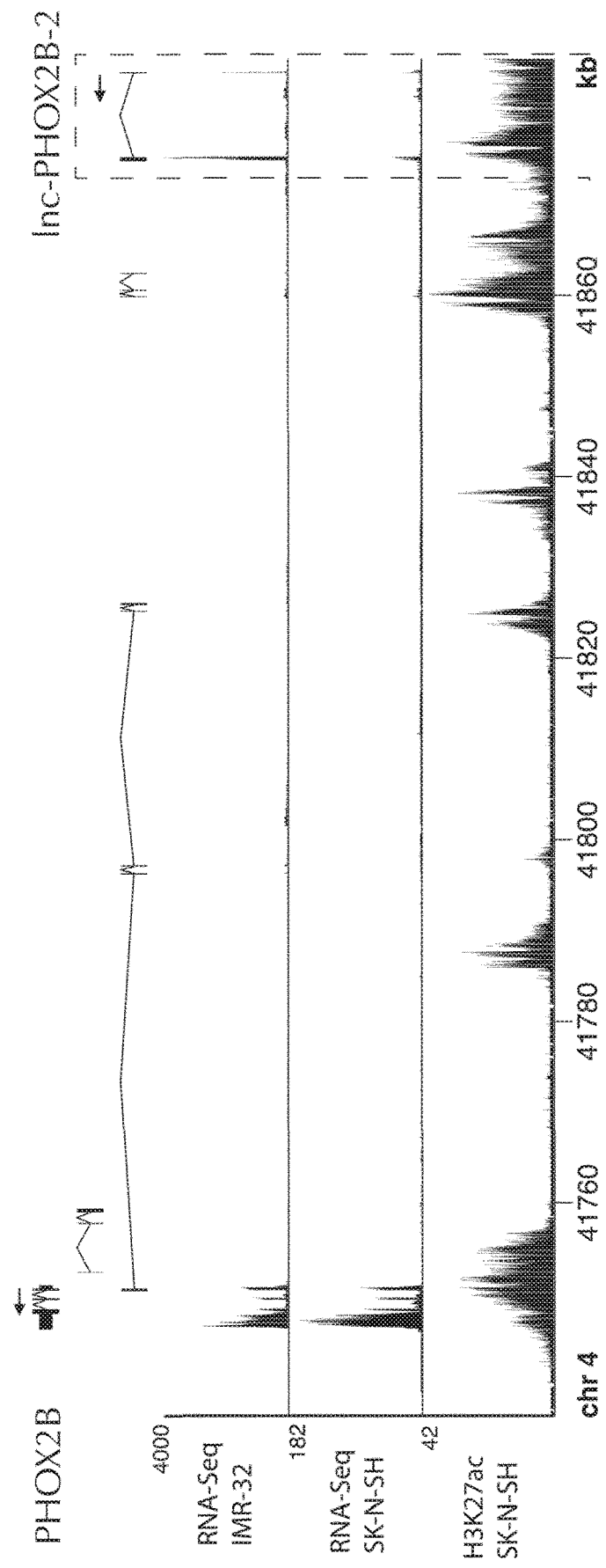
FIG. 4: shows the RNA-sequencing tracks in two neuroblastoma cell lines (IMR-32 and SK-N-SH) of the PHOX2B locus in the two top panels. The bottom panel visualizes the H3K27ac chromatin marks in this region. The presence of a high number of peaks indicates the region to be a super-enhancer.

Example 4 (FIG. 4)

RNA-sequencing was performed on IMR-32. RNA was isolated using the miRNeasy Micro Kit for Qiagen, according to the manufacturer's protocol. RNA concentration and purity was evaluated using the Nanodrop. The library was prepared using the TruSeq Stranded mRNA library prep kit, with an initial RNA input of 100 ng. Library quality was quantified using the Agilent 2100 BioAnalyzer High Sensitivity chip. Paired sequencing (2×75) was performed on the Illumina NextSeq 500 platform, using a high-output flow cell. FastQ. files were generated with the Illumina pipeline. Mapping was performed with Tophat, using genome build GRCh37.

The SK-N-SH RNA-seq and SK-N-SH H3K27ac ChIP sequencing track was extracted from the ENCODE data repository.

Figure 5:
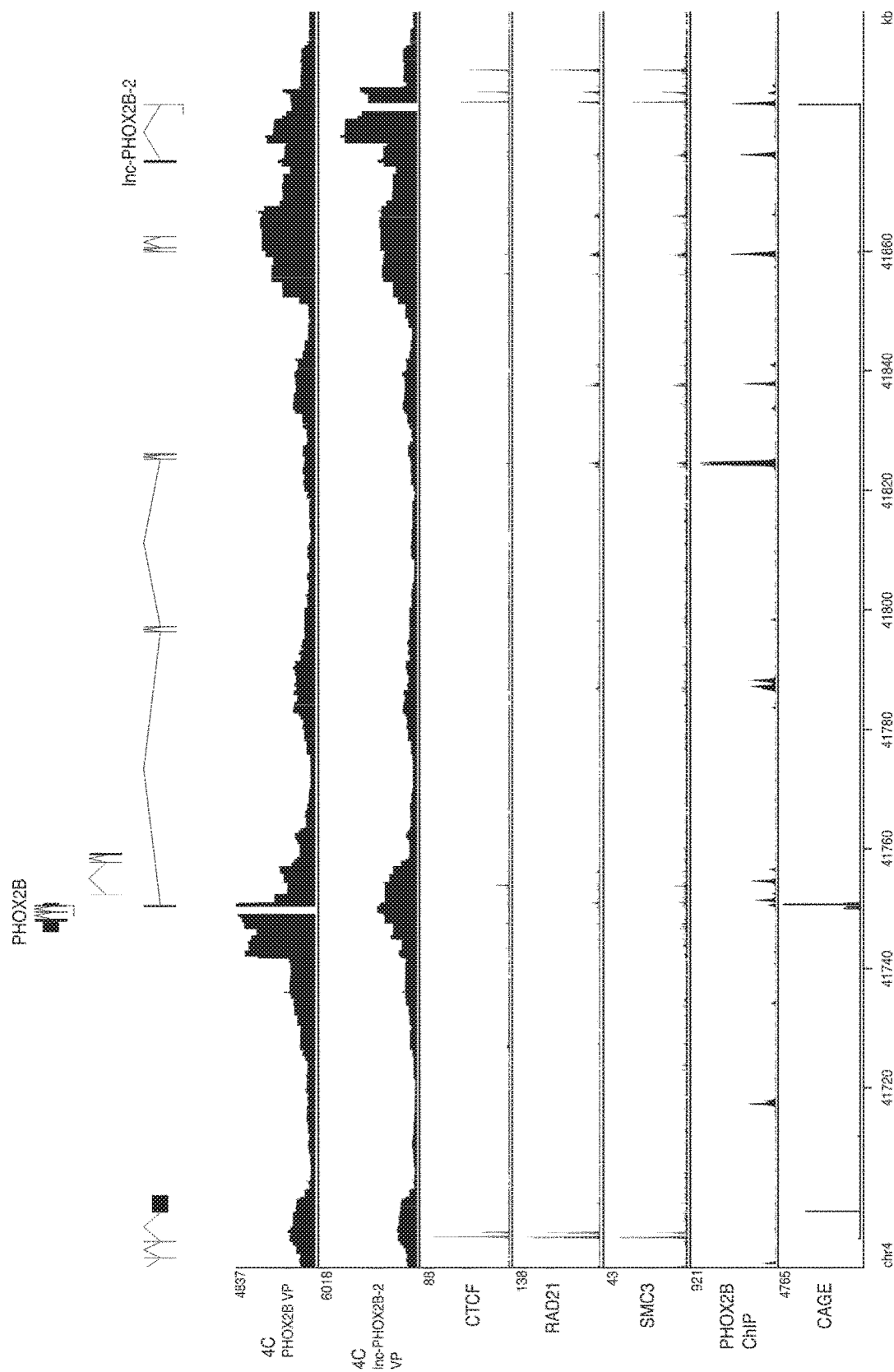
FIG. 5: The two top panels visualize 4C sequencing track using two viewpoints, showing the chromatin looping between PHOX2B and lnc-PHOX2B-2. This looping is further supported by CTCF, RAD21 and SMC3 binding sites, identified through ChIP-sequencing (middle panels). PHOX2B ChIP-sequencing indicates PHOX2B binding in the promotor region of lnc-PHOX2B-2, indicating PHOX2B could regulate lnc-PHOX2B-2 expression. The bottom panel shows CAGE peaks, confirming that the lnc-PHOX2B-2 transcript is independently transcribed.
Figure 6:
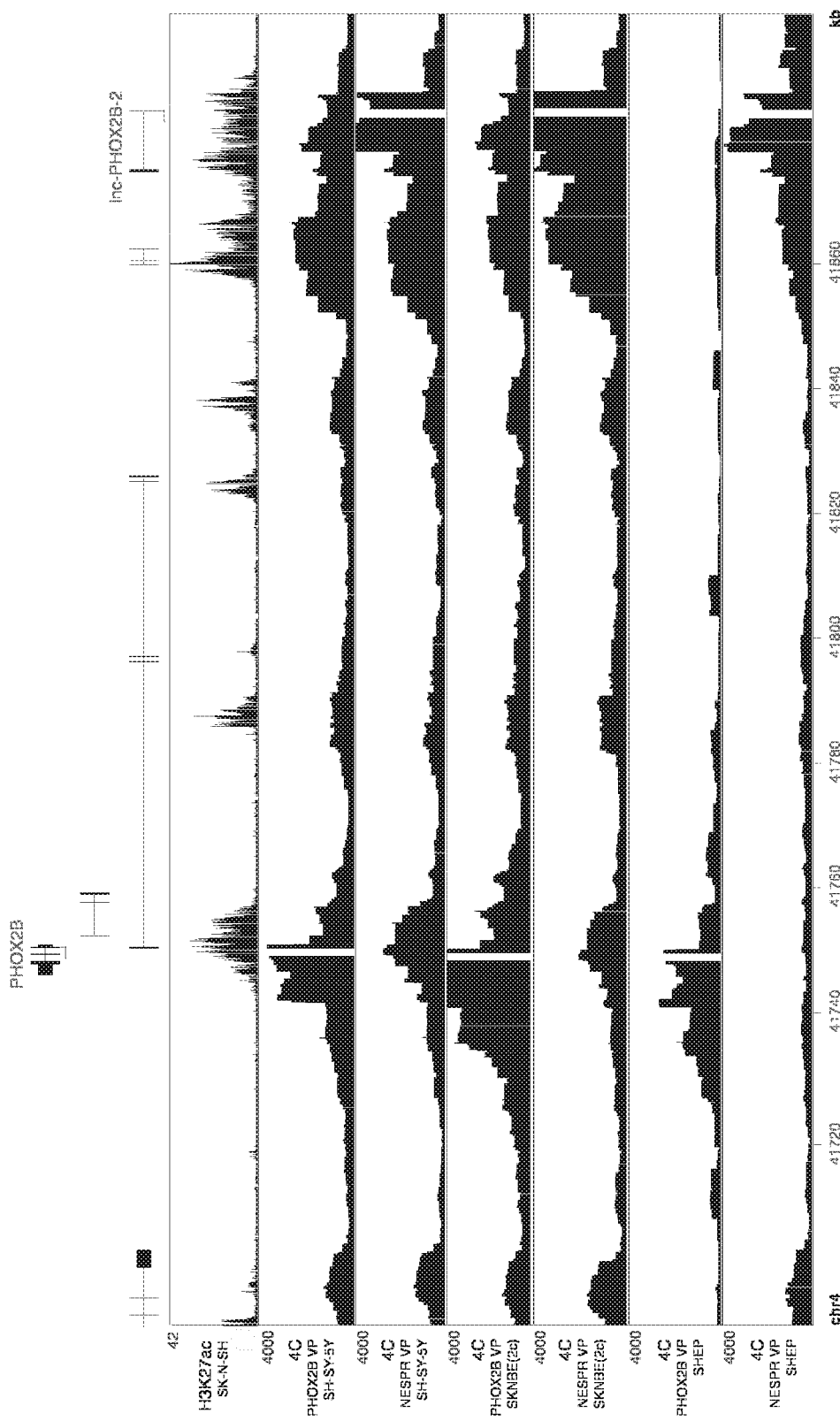
FIG. 6: The top panel shows the H3K27ac chromatin marks in the region. The next two tracks visualize the same 4C-sequencing peaks as in FIG. 5. The bottom panels show 4C-sequencing tracks in two additional cell lines, SKNBE (2c), a PHOX2B and lnc-PHOX2B-2 positive cell line and SHEP, a PHOX2B and lnc-PHOX2B-2 negative cell line.

Example 5 (FIGS. 5 and 6)

4C templates were prepared according to the protocol of Van de Werken et al. (Harmen J. G. van de Werken et al. 2012). In brief, for each template $1 \times 10^7$ cells were detached, counted, resuspended and crosslinked by incubating them with 2% formaldehyde for 10 min at room temperature. Following cell lysis, crosslinked DNA was digested with 400 U of DpnII restriction enzyme (NEB #R0543L) and nearby DNA fragments were ligated using 50 U of T4 DNA ligase (Roche #10799009001). Ligated DNA circles were de-crosslinked overnight using proteinase K and purified with NucleoMag P-Beads (Macherey-Nagel) to obtain an intermediate 3C template. A second round of digestion and ligation, using 50 U of Csp6I restriction enzyme (Thermo Scientific #ER0211), resulted in 4C templates.

Adaptor-containing reading and non-reading primers, specific to the viewpoints of interest, were designed to amplify all captured, interacting DNA fragments (Harmen J G van de Werken et al. 2012) (Table SI & S2). For each viewpoint, 16 PCR reactions, each using 200 ng of input 4C template, were pooled. Resulting 4C sequencing libraries were purified using High Pure PCR Product Purification kit (Roche #11732676001) and QIAquick PCR Purification kit (Qiagen #28106). Approximately 15-20 different 4C sequencing libraries were pooled and sequenced simultaneously on an Illumina NextSeq 500 (single-end, 75 nt, loading concentration 1.6 pM).

CTCF, RAD21 and SMC3 binding and CAGE peaks in SK-N-SH were extracted from the public ENCODE data repository. PHOX2B ChIP-sequencing data were obtained from GEO GSM2664369).

Figure 7:
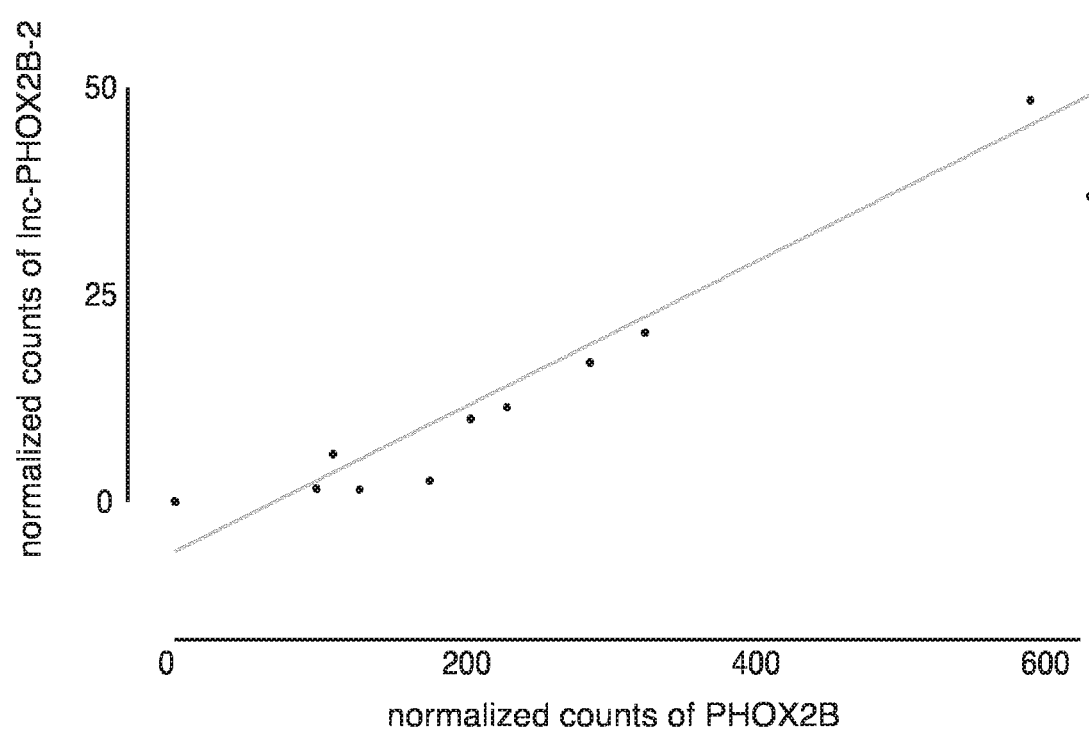
FIG. 7: Correlation between lnc-PHOX2B-2 and PHOX2B expression in 13 neuroblastoma cell lines, extracted from the CCLE RNA-seq data repository.
Figure 8A:
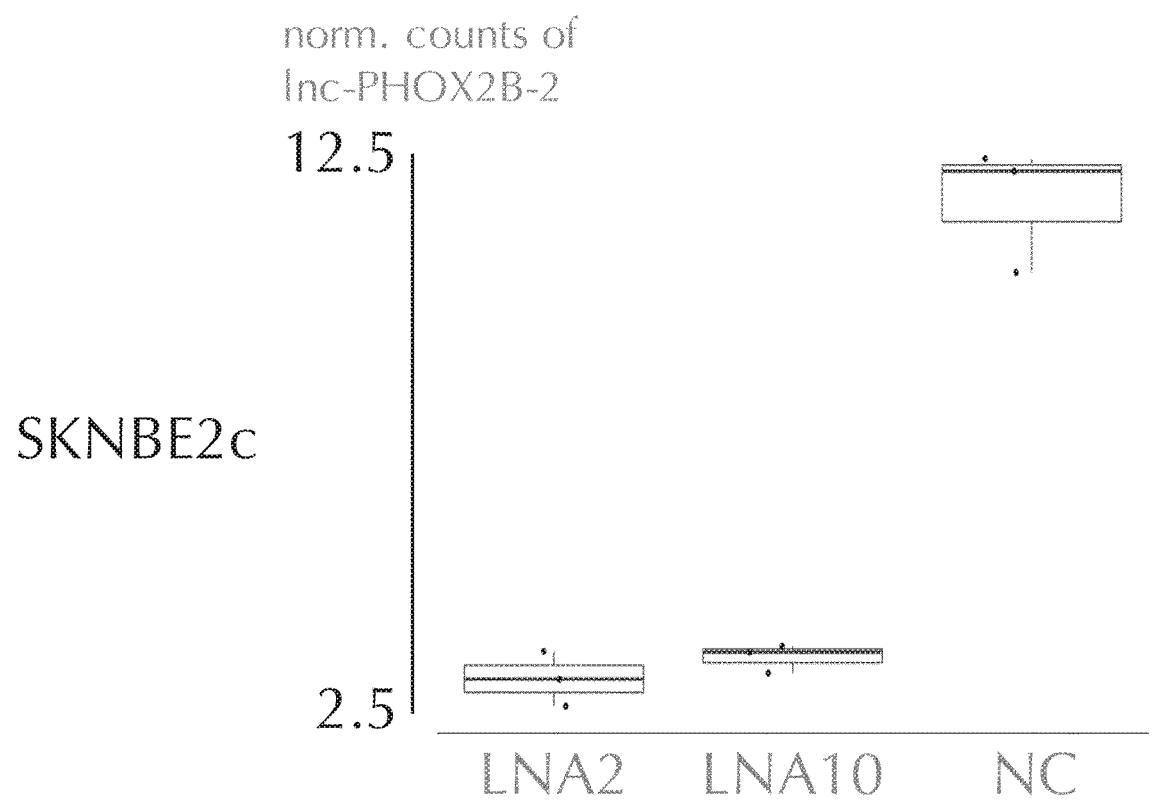
FIG. 8: ASO-based inhibition of lnc-PHOX2B-2 in SKNBE(2c) (FIGS. 8a and 8b) and NGP (FIGS. 8c and 8d). Using RNA-sequencing, reduction of lncRNA expression was quantified, as well as the difference in expression of PHOX2B between the treated samples and the control.
Figure 8B:
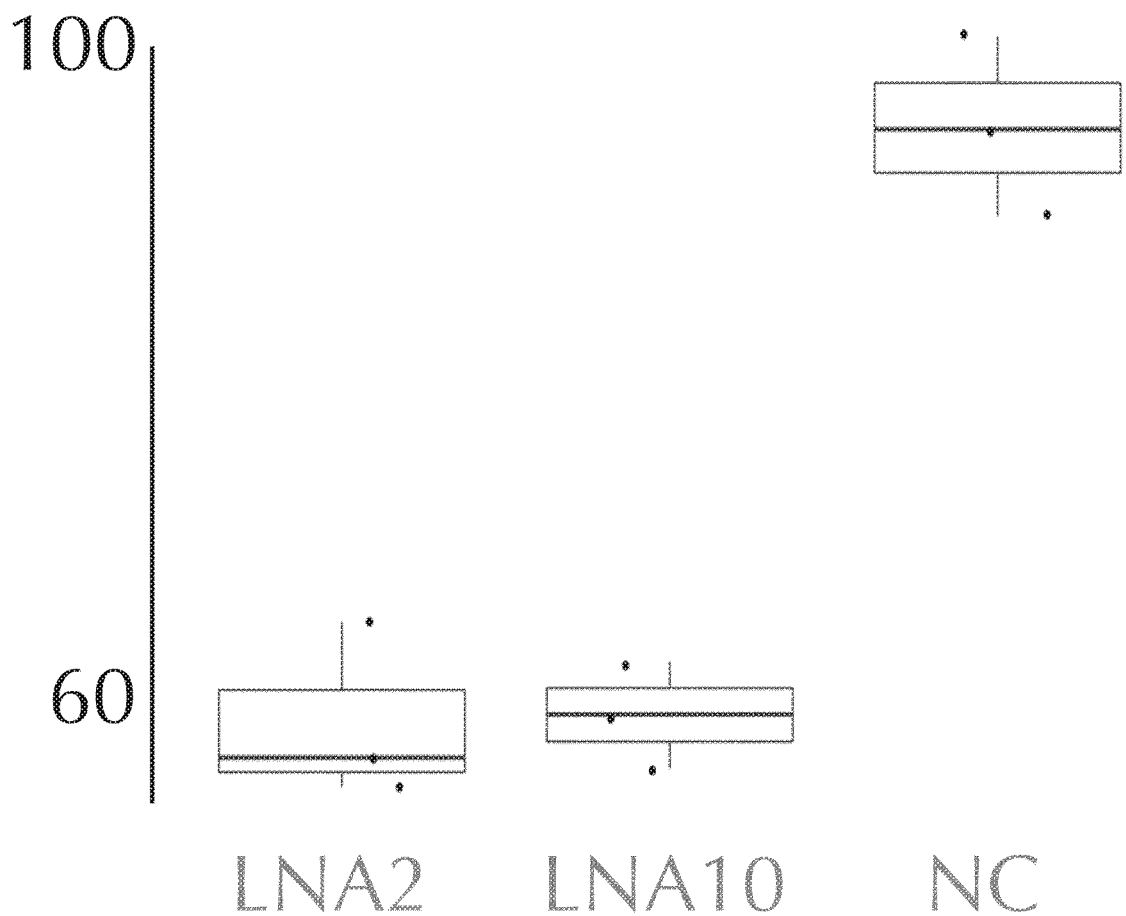
Figure 8C:
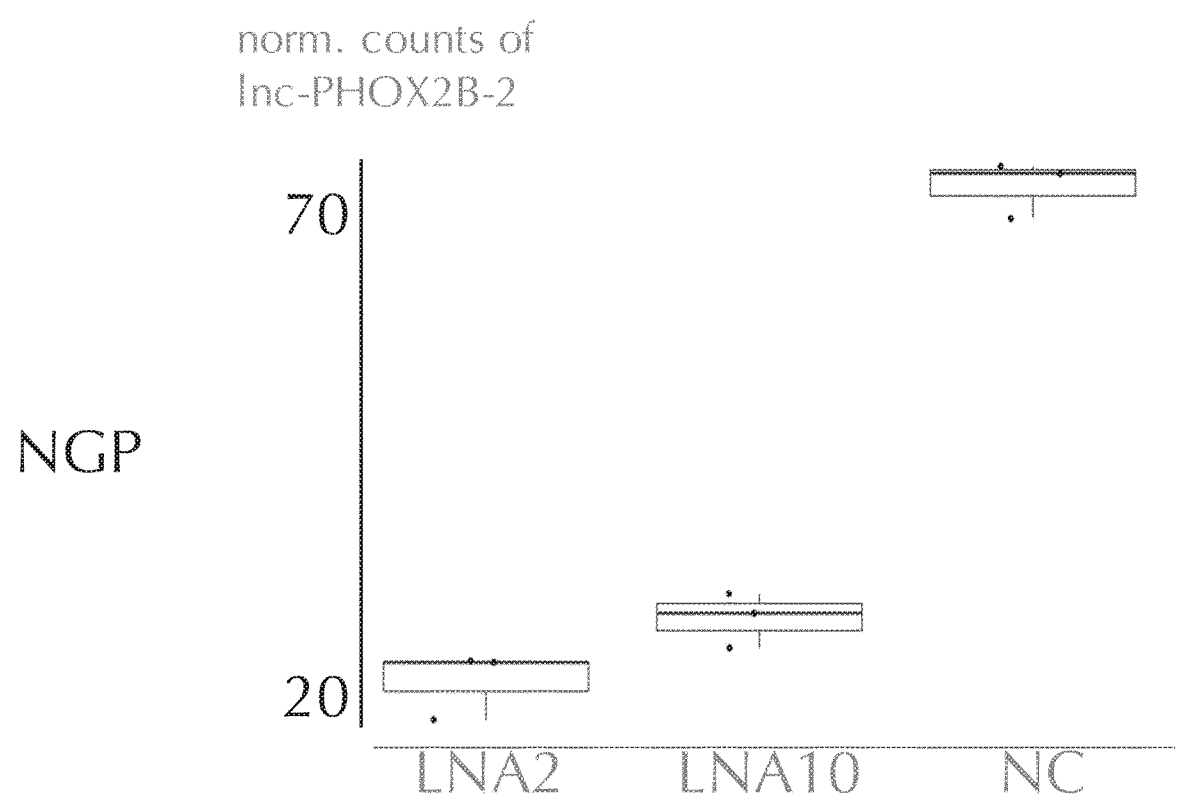
Figure 8D:
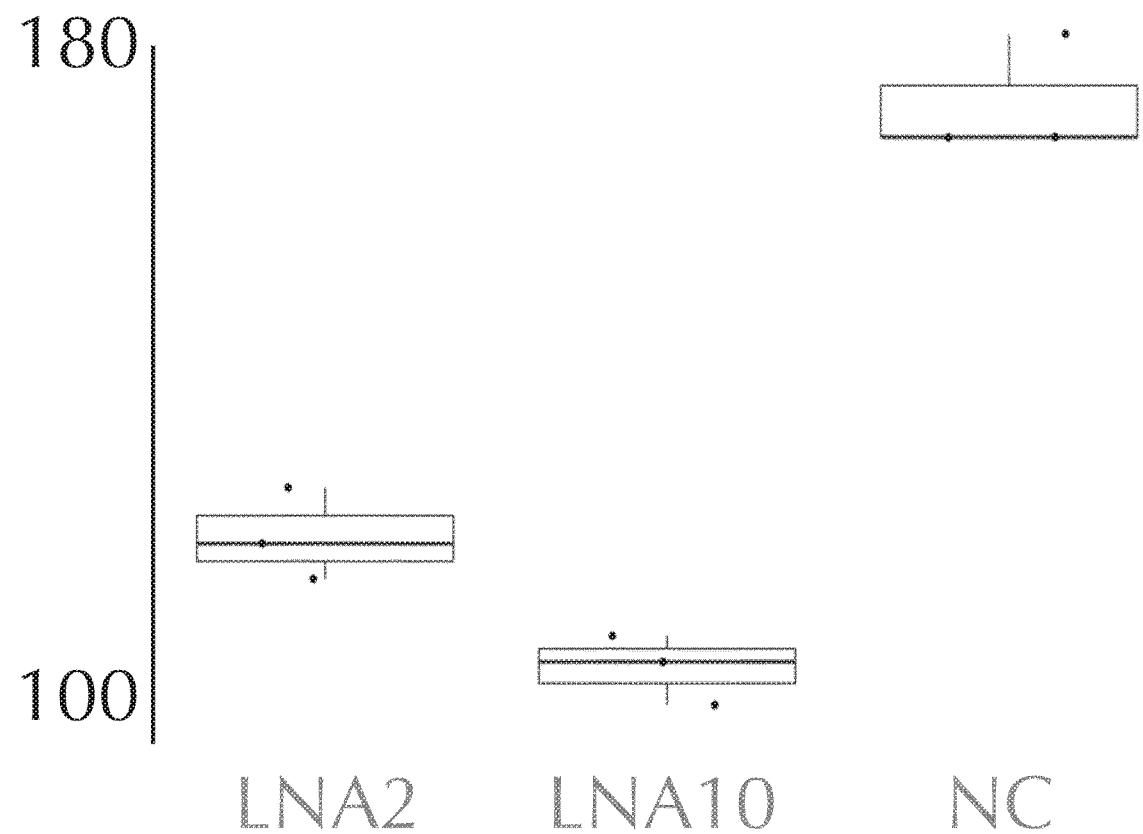
Figure 9A:
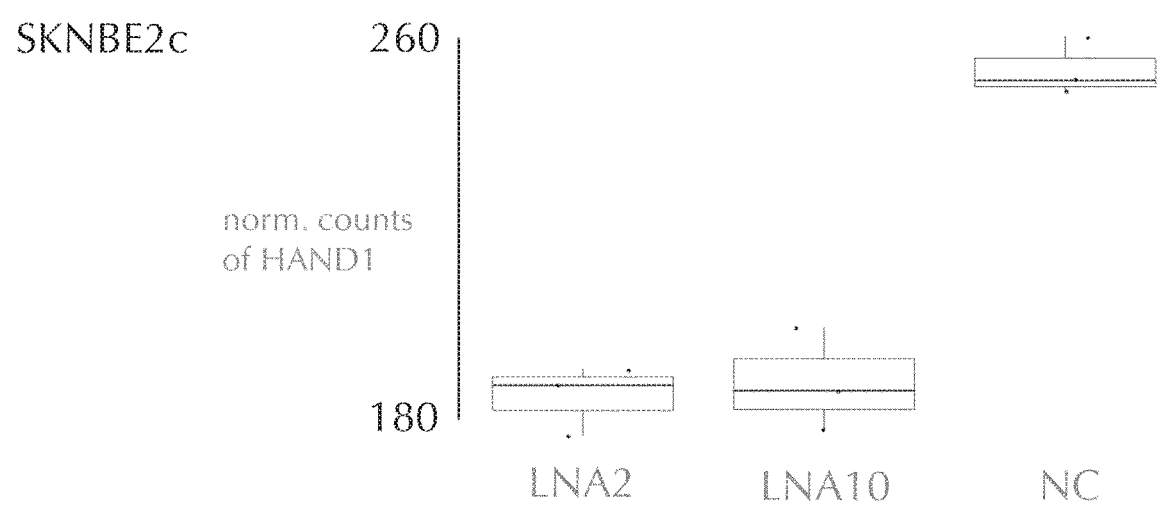
FIG. 9: Inhibition of lnc-PHOX2B-2 in SKNBE(2c) (FIGS. 9a and 9b) and NGP (FIGS. 9c and 9d) results in reduction in expression levels of several neuroblastoma master regulators.
Figure 9B:
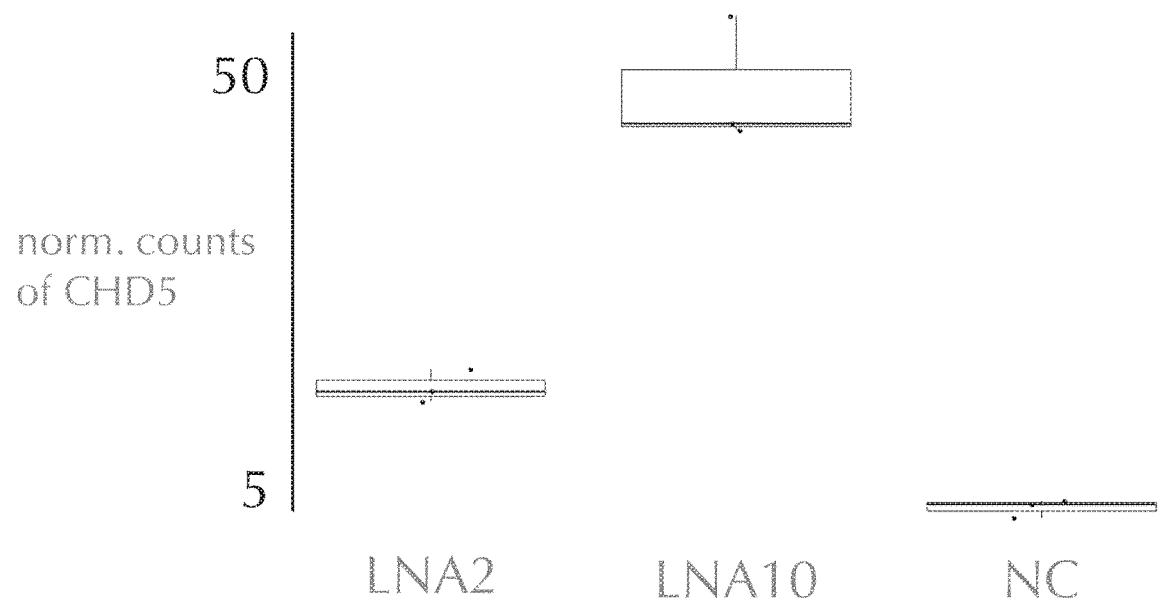
Figure 9C:
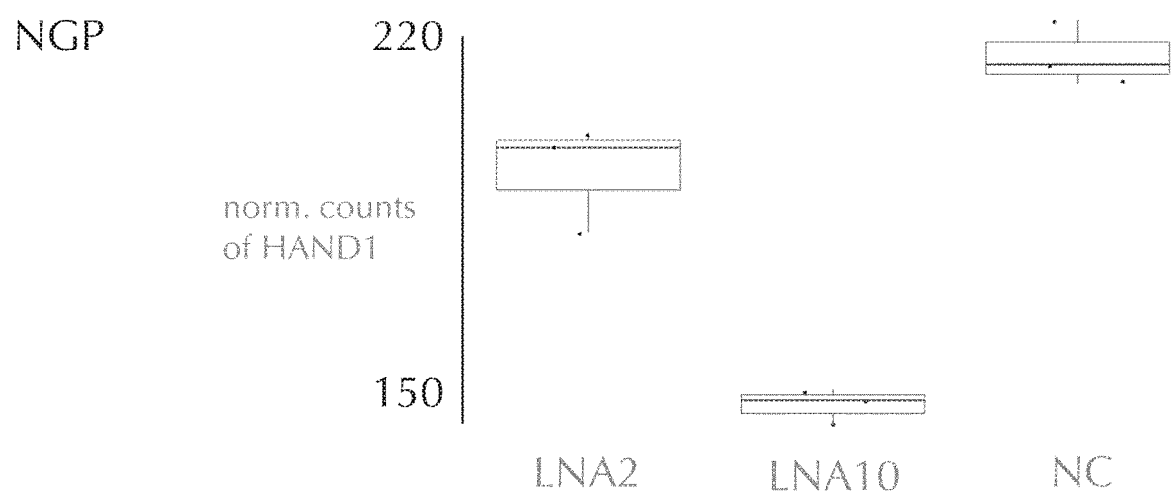
Figure 9D:
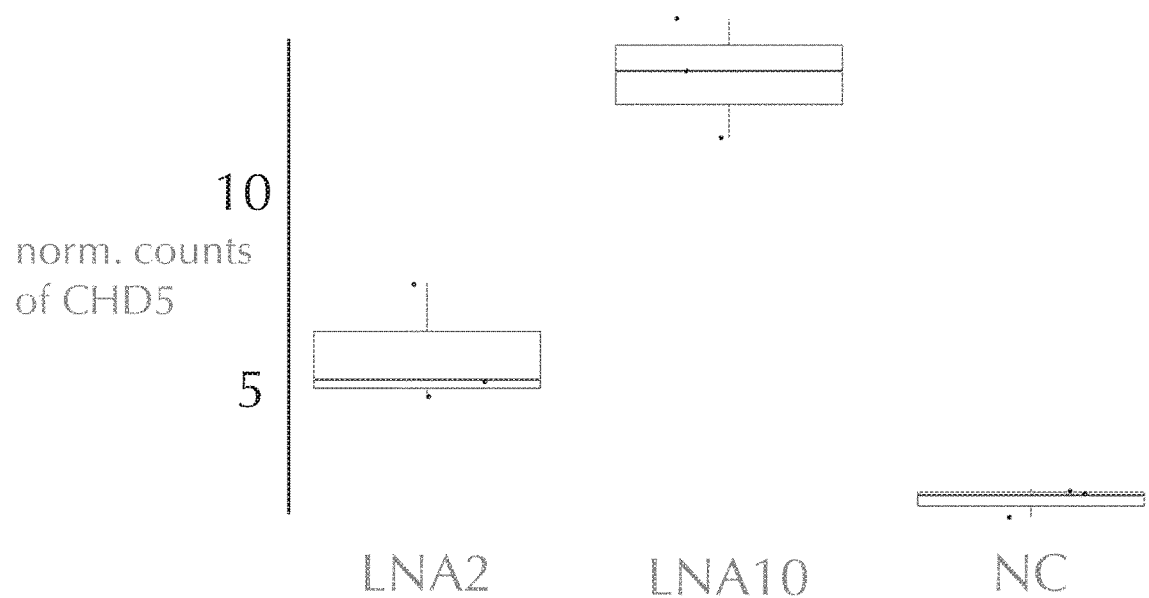

Example 6 (FIG. 7)

Correlation between lnc-PHOX2B-2 and PHOX2B was plotted in a scatter plot, using normalized expression values of the two genes. Normalization was done with the edgeR package, over all available cancer types in the CCLE data repository. Neuroblastoma cell lines were extracted from the whole set and expression levels of both genes were plotted. Correlation coefficients and significance were calculated with the Spearman and Pearson method.

Example 7 (FIG. 8)

Perturbation of lnc-PHOX2B-2 was performed through antisense oligonucleotides with an LNA modification. The ASO sequences are as flows:

```
LNA2:
                                            (SEQ ID No 13)
G*C*T*C*G*A*A*T*G*A*T*C*T*T*A

LNA10:
                                            (SEQ ID No 14)
A*A*A*A*C*T*G*A*T*C*G*A*C*G*C*A
```

These ASOs were transfected in two neuroblastoma cell lines, SKNBE(2c) and NGP, using lipofectamine. ASO concentration used in the transfection experiments was 100 nM. RNA was extracted using the miRNeasy Micro Kit for Qiagen, according to the manufacturer's protocol. RNA concentration and purity was evaluated using the Nanodrop. The library was prepared using the TruSeq Stranded mRNA library prep kit, with an initial RNA input of 100 ng. Library quality was quantified using the Agilent 2100 BioAnalyzer High Sensitivity chip. Paired-end sequencing (2×75) was performed on the lllumina NextSeq 500 platform, using a high-output flow cell. FastQ files were generated with the lllumina pipeline.

Counts were generated using the Kallisto pipeline, a pseudo-alignment algorithm. Normalization of the counts was performed using the edgeR package.

Example 8 (FIG. 9)

Normalized counts of genes of interest were plotted in a boxplot with the ggplot2 package in R.

Figure 10A:
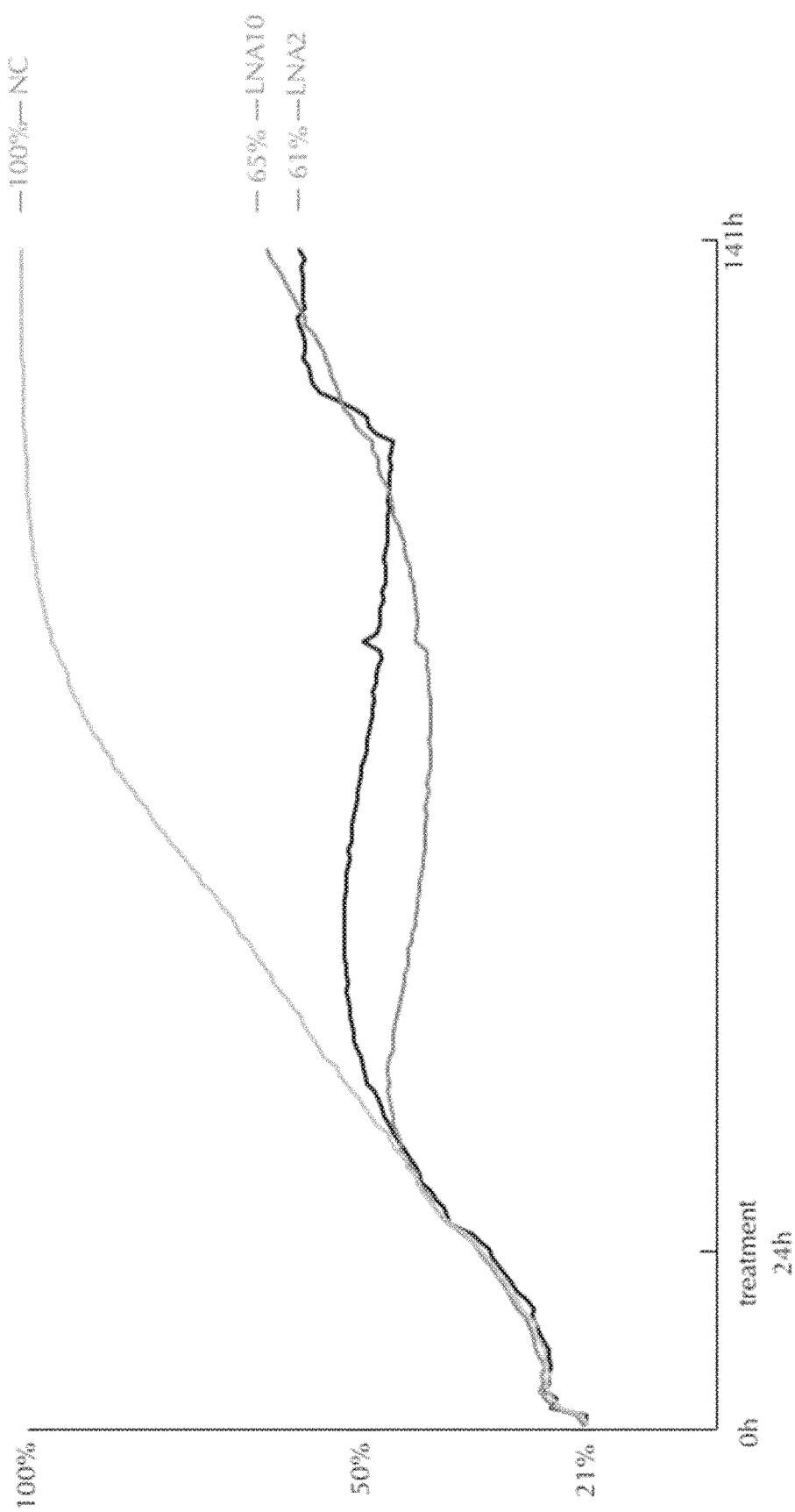
FIG. 10: ASO-based inhibition of lnc-PHOX2B-2 inhibition in SKNBE(2c)(FIG. 10a) and NGP (FIG. 10b). By measuring confluence using the IncuCyte, growth reduction of neuroblastoma cells after knock down of the lncRNA could be visualized.
Figure 10B:
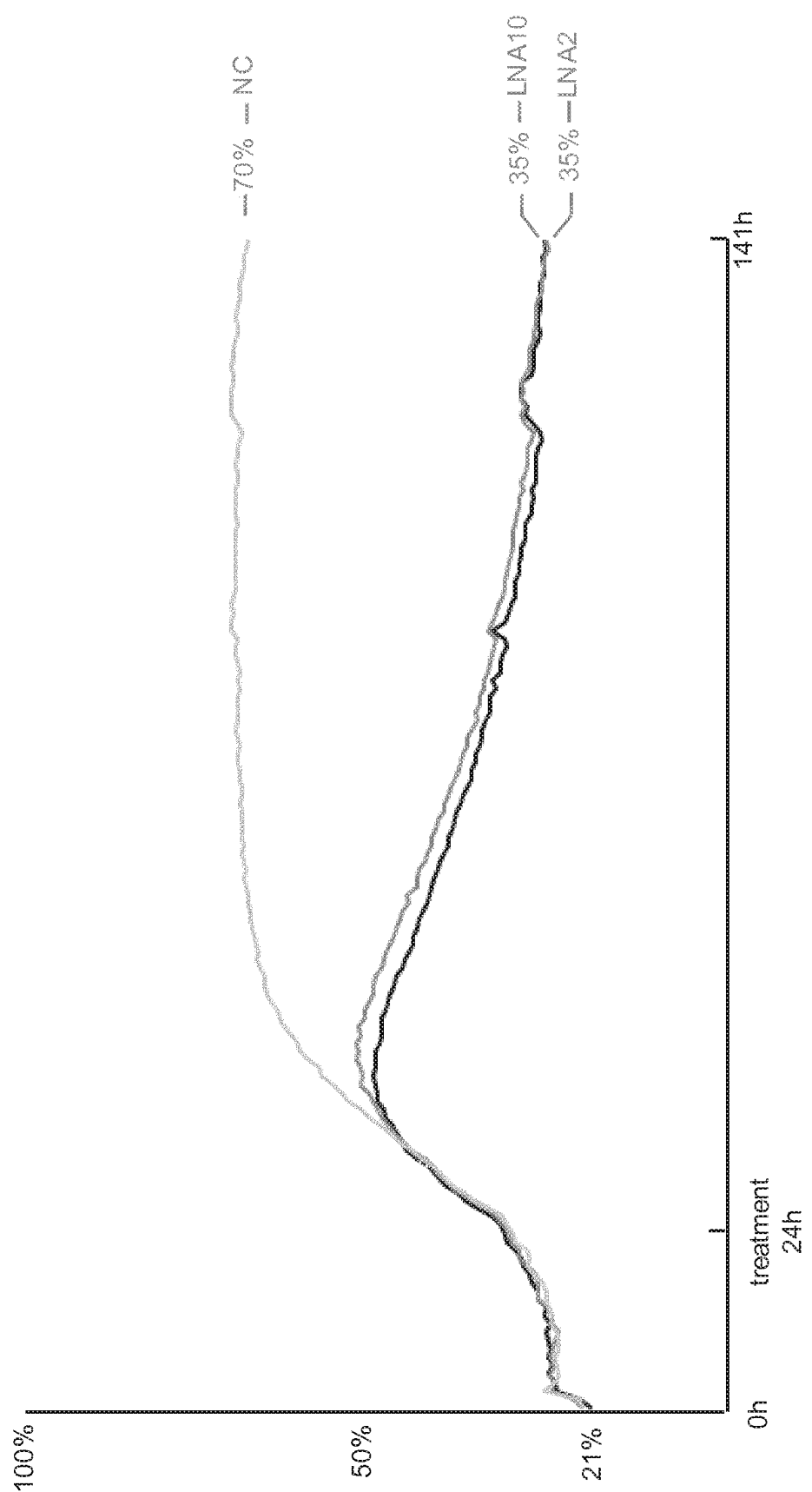

Example 9 (FIG. 10)

Two neuroblastoma cell lines, SKNBE(2c) and NGP, were seeded in a 96-well plate and transfected with ASOs (100 nM) after 24 h (lipofectamine based). Real-time analysis using the IncuCyte, provided insights in the percentage of confluence in the wells. Confluence measurements were performed for 141 hours. Error bars are not shown for visualization purposes.

Figure 11:
FIG. 11: The amount of growth reduction is dependent on the used concentration of LNA.

Example 10 (FIG. 11)

NGP was transfected with 2 ASOs at the following concentrations: 100, 50, 20, 10, 2 and 1 nM. Confluence response to the transfection was measured using the IncuCyte for 192 hours. Error bars are not shown for visualization purposes.

Figure 12A:
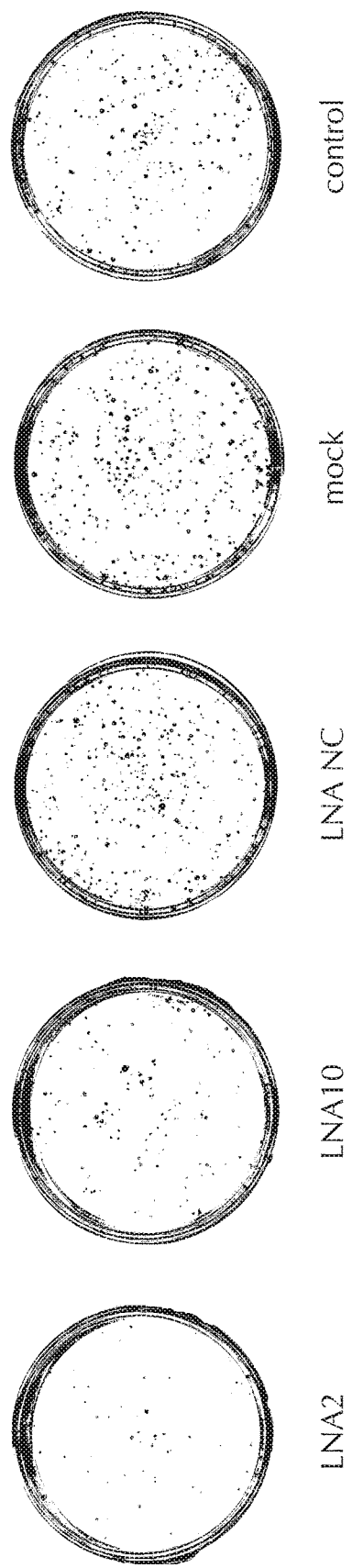
FIG. 12: shows a colony formation assay in SKNBE(2c) (FIG. 12a). Colony formation capacity is reduced after treatment with ASOs, in comparison to several controls (FIG. 12b).
Figure 12B:
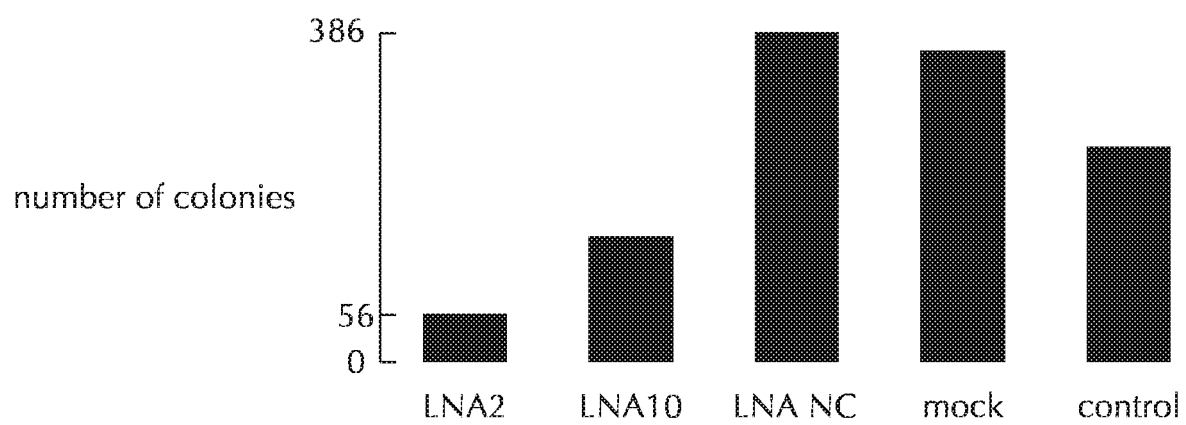
Figure 13A:
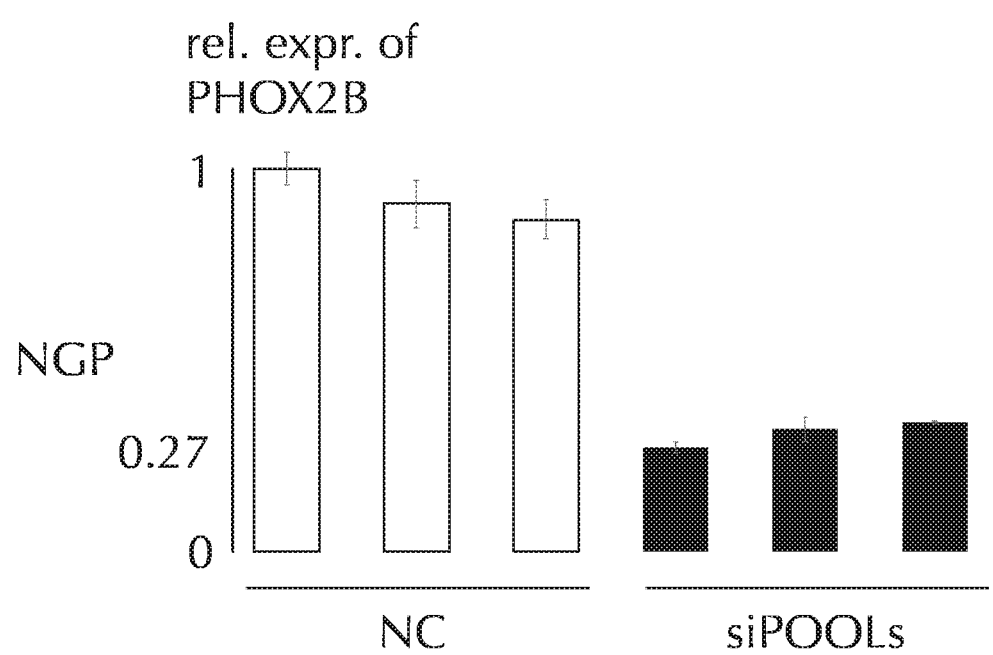
FIG. 13: Other methods of knock down have been evaluated in NGP (FIGS. 13a and 13b) and SKNBE(2c) (FIGS. 13c and 13d), such as siPOOLs. This method results in an expression reduction of lnc-PHOX2B-2, but does not have an effect on PHOX2B expression levels.
Figure 13B:
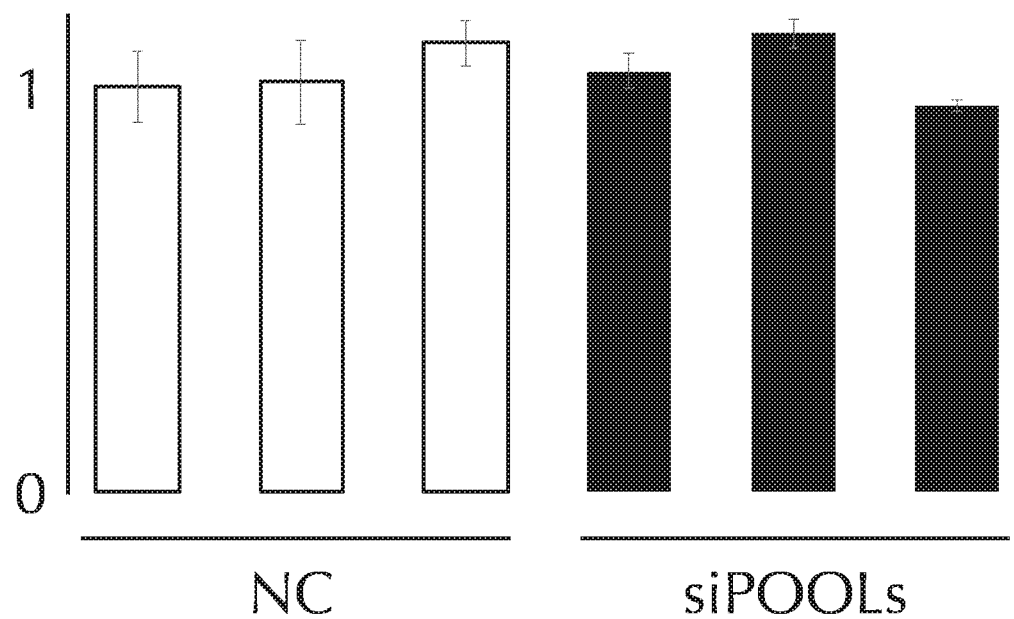
Figure 13C:
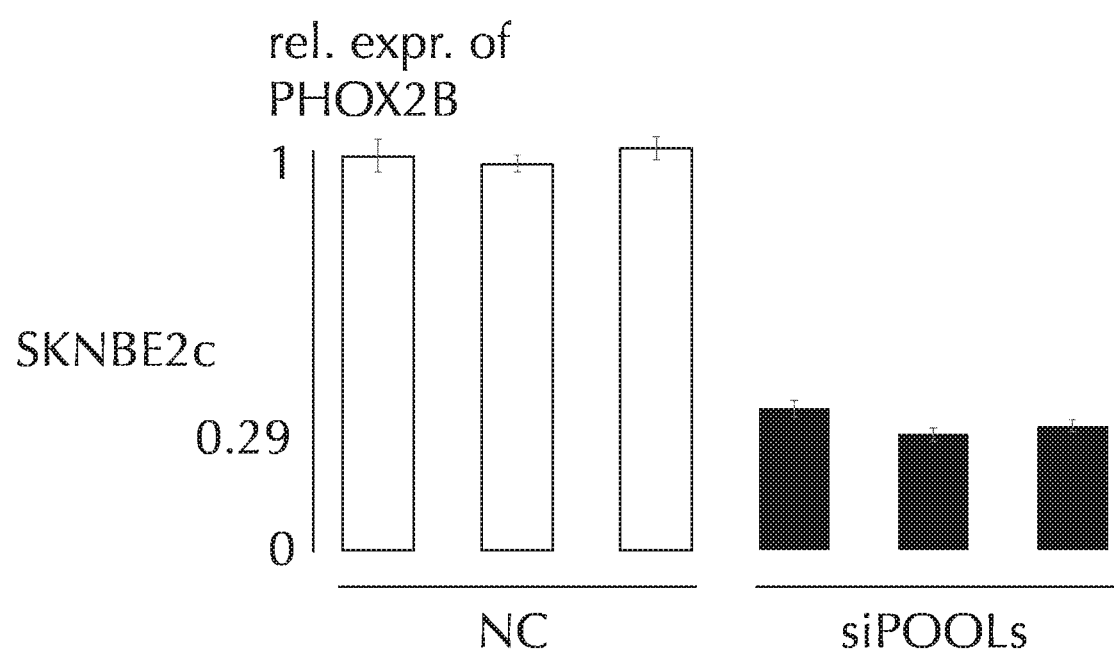
Figure 13D:
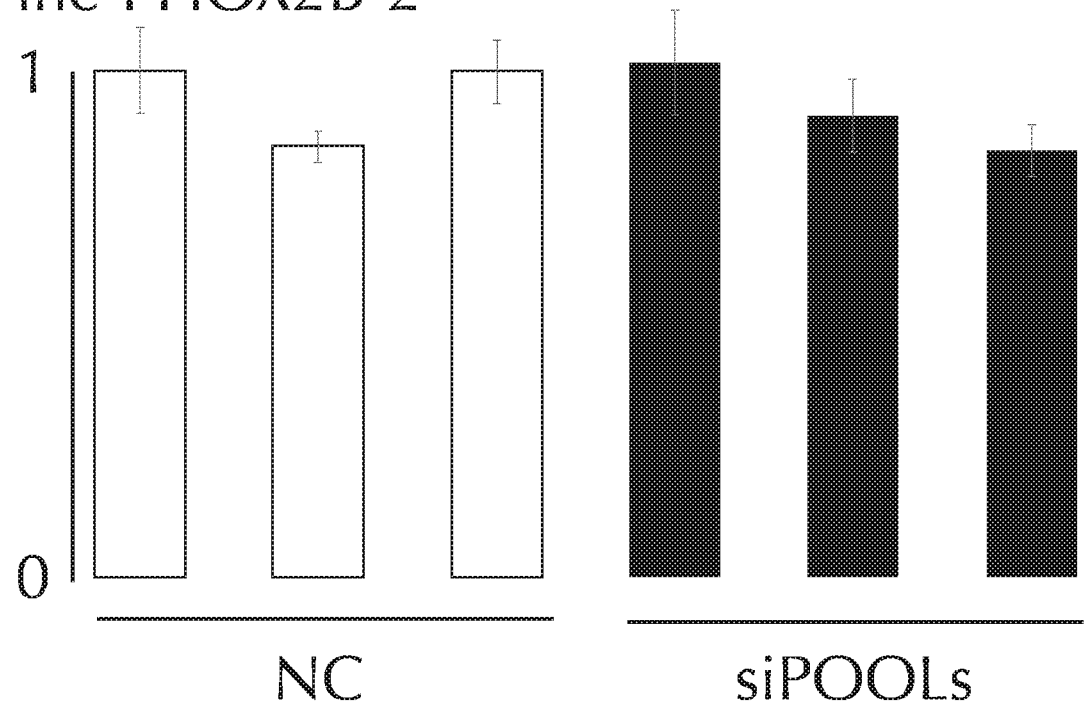
Figure 14A:
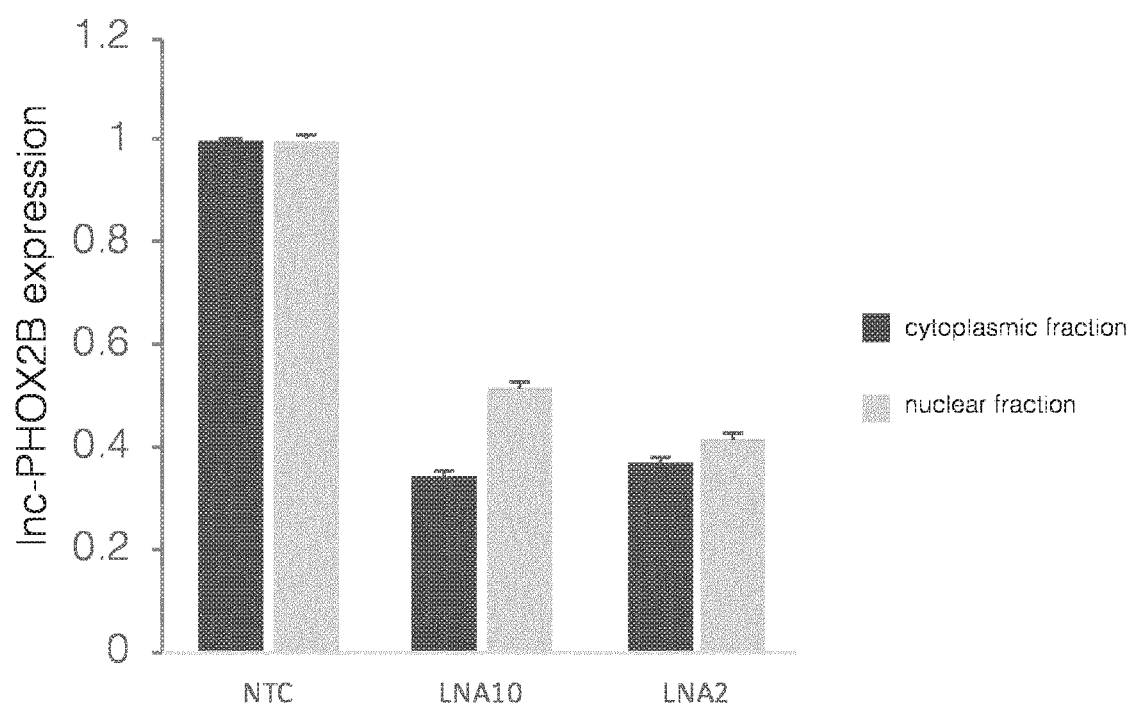
FIG. 14: Boxplot of relative expression levels of lnc-PHOX2B-2 (FIGS. 14a and 14b) and PHOX2B (FIGS. 14c and 14d) in the cytoplasmic and nuclear fraction. ASO-based inhibition has an effect in both cellular compartments, whereas the siPOOLs only function in the cytoplasmic fraction.
Figure 14B:
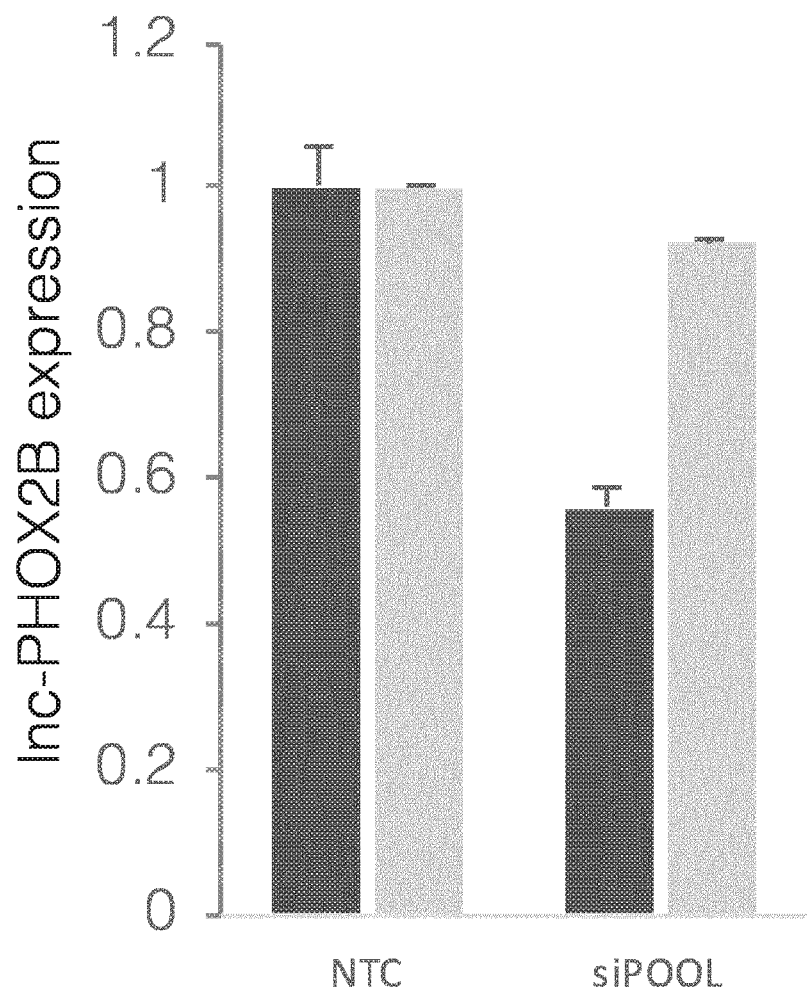
Figure 14C:
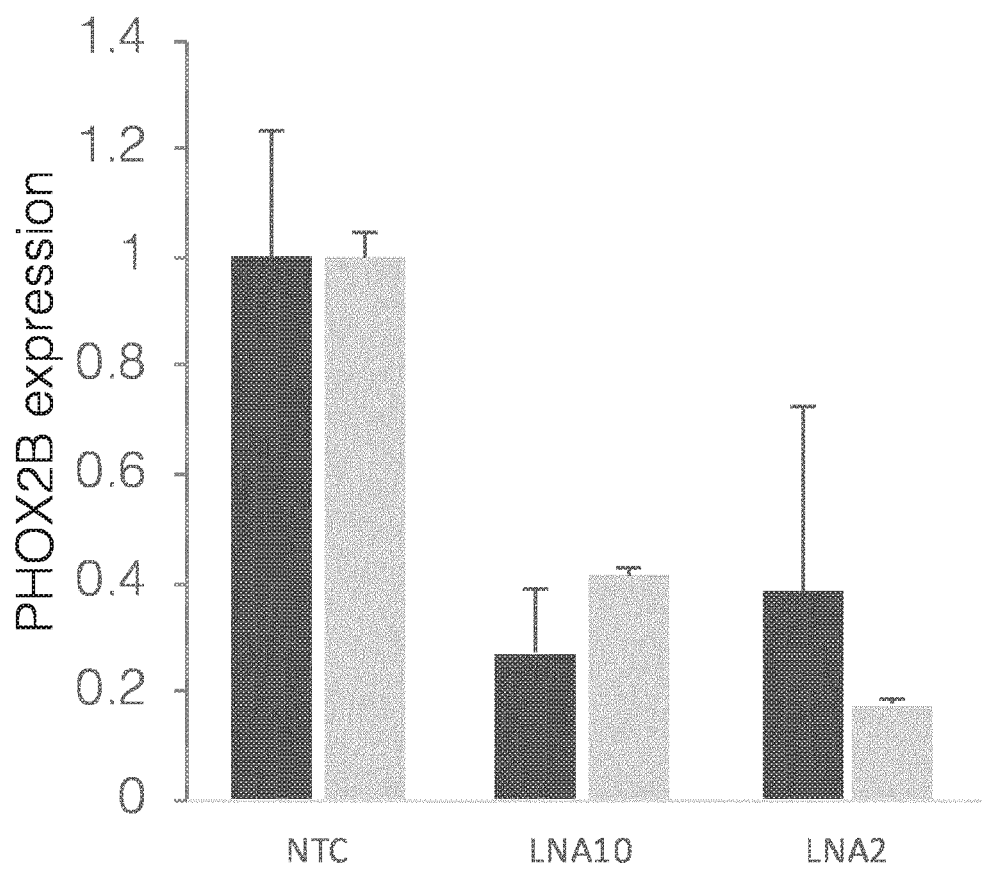
Figure 14D:
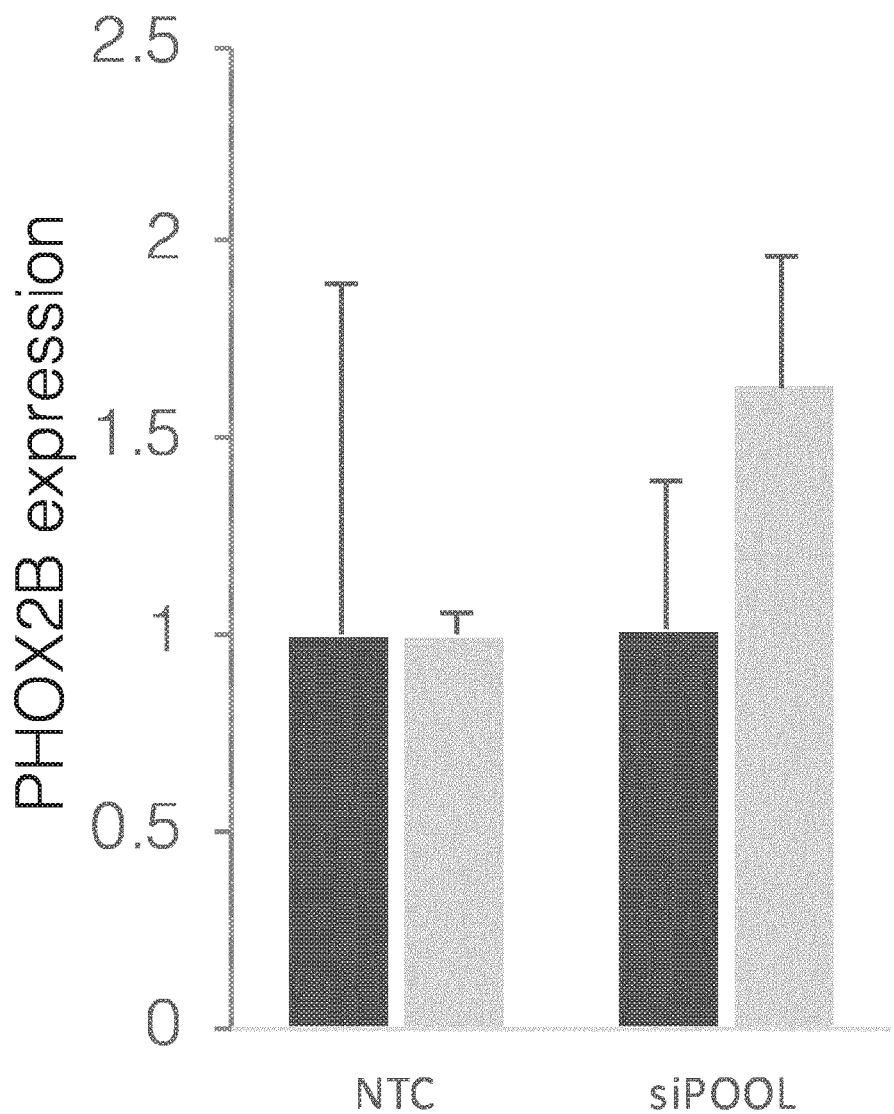

Example 11 (FIG. 12)

Colony formation assay was performed using SKNBE (2c). The neuroblastoma cells were transfected with lipofectamine, using ASOs (100 nM). After 24 hours, the cells were harvested and reseeded at a density of 2000 cells per 6 cm dish. The formation of colonies was allowed for 7 days, after which the colonies were fixated and stained. Quantification of the number of colonies was done using ImageJ.

Example 12 (FIG. 13)

Two cell lines, NGP and SKNBE(2c), were transfected with siPOOLs, which consist of 30 siRNAs all targeting the same transcript. Lipofectamine was used to perform the transfection, at a concentration of 100 nM of siPOOLs. RNA was harvested using the miRNeasy Micro Kit for Qiagen, according to the manufacturer's protocol. RNA concentration and purity was evaluated using the Nanodrop. Reverse transcription was carried out using the iScript advanced kit (BioRad). The qPCR was run on the LightCycler480 platform, using three reference genes (SDHA, TBP and YWHAZ). Relative expression was calculated using qbase+ (Biogazelle).

The Primers used to quantify expression of lnc-PHOX2B-2 were:

```
Assay1
FP:
                                            (SEQ ID NO: 15)
GTTGGAGTCTGCACAGTTGG RP:
                                            (SEQ ID NO: 16)
CTTTGCCCACTTTCTGACCC Assay2 (intronspanning)
FP:
                                            (SEQ ID NO: 17)
AAT G CG CG CACCTT C AAC RP:
                                            (SEQ ID NO: 18)
CTTTGCCCACTTTCTGACCC
```

Example 13 (FIG. 14)

RNA fractionation of the neuroblastoma cell line SKNBE (2c). The cells were first transfected as mentioned before (lipofectamine-100 nM-24 h). After transfection, cytoplasmic and nuclear RNA was harvested separately. Reverse transcription was carried out using the iScript advanced kit (BioRad). The qPCR was run on the LightCycler480 platform, using three reference genes (SDHA, TBP and YWHAZ). Relative expression was calculated using qbase+.

Figure 15A:
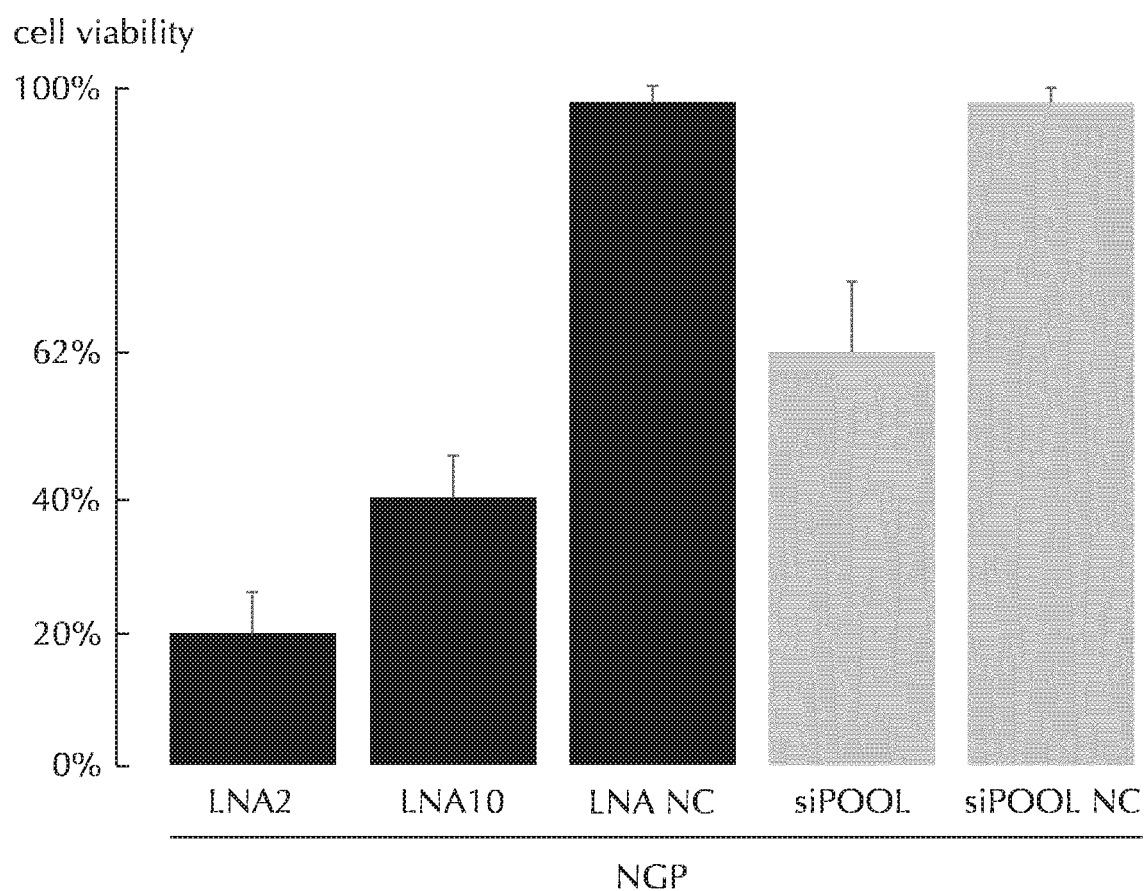
FIG. 15: ASO-based inhibition in NGP (FIG. 15a) and SKNBE(2c) (FIG. 15b). Measurement of cell titer glo shows the decrease in cell viability after knock down of lnc-PHOX2B-2 in neuroblastoma cells.
Figure 15B:
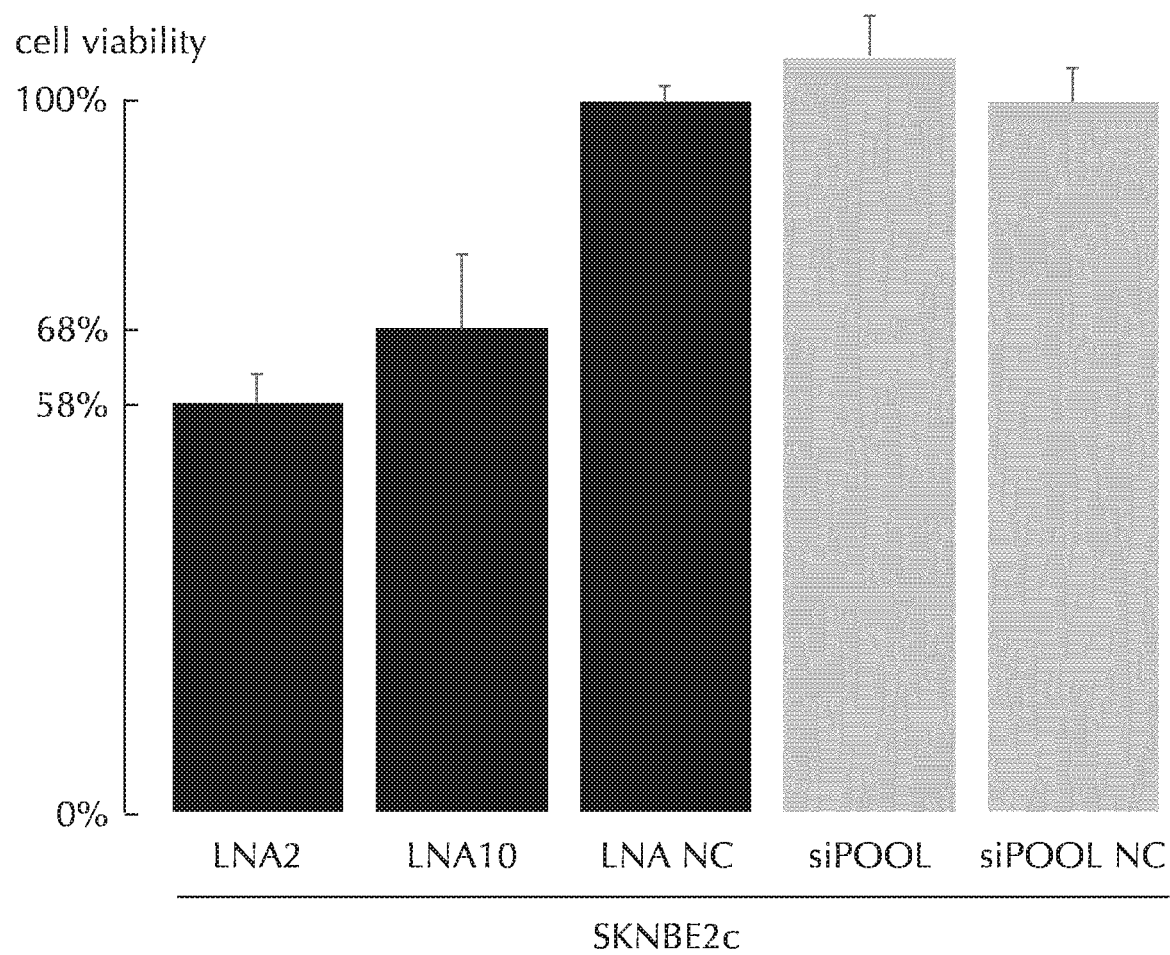

Example 14 (FIG. 15)

NGP and SKNBE(2c) were seeded in a 96-well plate (10.000 cells) and transfected using lipofectamine and an ASO concentration of 100 nM. After 72 hours, a Cell Titer Glo assay was performed. The entire volume of medium was removed, after which 100 pL of complete medium was added. 100 pL of Cell Titer Glo was added to the new medium. The plate was shaken for 10 minutes and read-out in a GloMax.

Figure 16A:
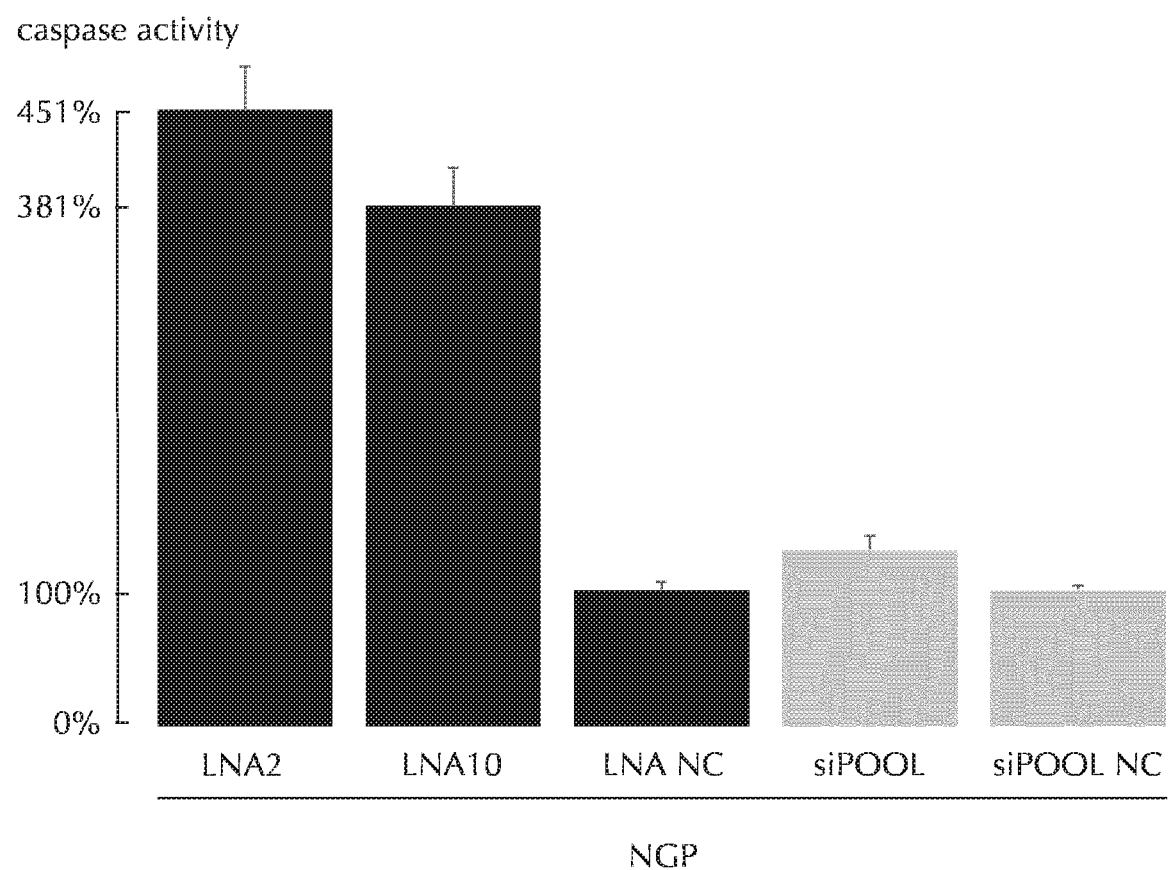
FIG. 16: ASO-based inhibition in NGP (FIG. 16a) and SKNBE(2c) (FIG. 16b). After knock down of the lncRNA, an increase in Caspase 3/7 could be observed, confirming that reduction of expression of lnc-PHOX2B-2 in neuroblastoma cells results in induction of apoptosis.
Figure 16B:
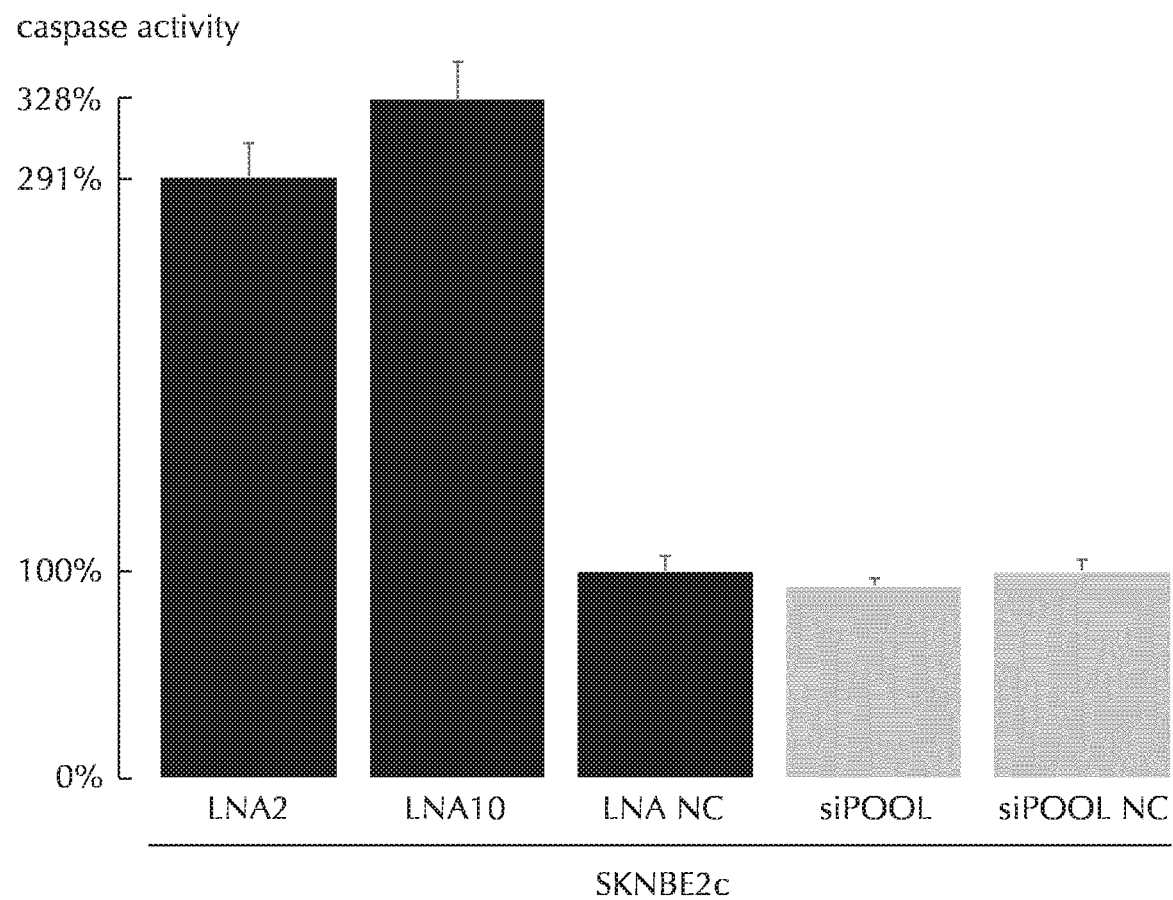

Example 15 (FIG. 16)

NGP and SKNBE(2c) were seeded in a 96-well plate (10.000 cells) and transfected using lipofectamine and an ASO concentration of 100 nM. After 72 hours, a Caspase3/7 assay was performed. The entire volume of medium was removed, after which 100 pL of complete medium was added. 100 pL of Caspase Glo was added to the new medium. The plate was shaken for 30 seconds, incubated for 30 minutes and read-out in a GloMax.

Figure 17:
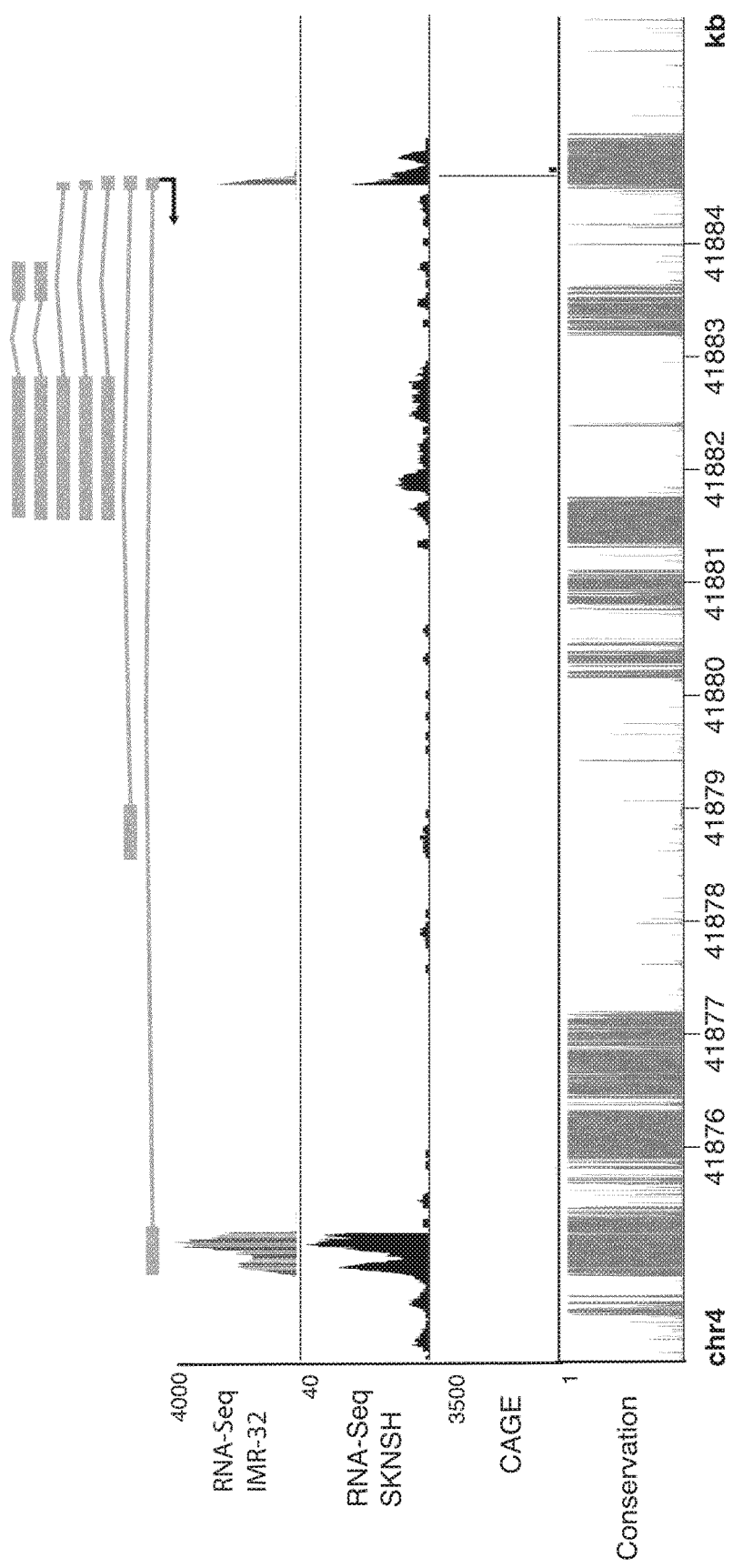
FIG. 17: lnc-PHOX2B-2 consists of multiple different transcripts, the longest lncRNA being the most abundant. This transcript is almost entirely conserved in 46 other mammals, shown in the bottom panel.

Example 16 (FIG. 17)

RNA-sequencing tracks of two neuroblastoma cell lines, IMR-32 and SK-N-SH, visualizing the different transcript structures. The SK-N-SH RNA-seq track was extracted from the publically available data repository ENCODE. The IMR-32 sequencing data was performed in-house (as mentioned before). The conservation track, cons46 way, was downloaded from UCSC. This track shows transcript structures that are conserved in 46 mammals.

Example 17: In Vivo Studies

Murine patient-derived xenograft models are used to study the therapeutic effects of in vivo lincRNA knockdown. Mice are treated with an ASO targeting the candidate lincRNA or a negative control ASO by intra-muscular injection. Treatment starts when tumors reach a size of 150 mm³ and consists of 5 injections per week for a period of 3-4 weeks, applying a dose of 50 mg/kg. Tumor volume is monitored over time during the entire course of the experiment. In case lincRNA knock down results in a reduction of tumor volume, the tumors are resected and blood is collected for various downstream analyses. Tumor sections are examined using immunohistochemistry for KI-67 and activated caspase-3 and RNA is isolated to confirm lincRNA knockdown. To evaluate whether lincRNA knockdown has an impact on metastatic burden, levels of circulating human DNA are quantified in murine blood samples using a dedicated RT-qPCR assay. Treatment toxicity (or the lack thereof) is assessed by pathologic examination of the liver, spleen and kidney of ASO treated mice. Tumor-derived RNA from lincRNA-targeting ASO and negative control ASO treated mice is profiled using RNA-sequencing to validate the observed anti-tumor effects on the molecular level.

Another model being used, in collaboration with the lab of Prof. dr. Jason Shohet, MD, is the TH-MYCN mouse. As these mice develop completely murine tumors, it is an interesting model to use in the determination of the effectiveness of out therapy. The same read-outs as with the xenograft model are performed.

REFERENCES

Consortium, T. E. P. (2012). An Integrated Encyclopedia of DNA Elements in the Human Genome. *Nature,* 489 (7414), 57-74. https://doi.org/10.1038/nature11247

Gutschner, T., & Diederichs, S. (2012). The hallmarks of cancer. *RNA Biology,* 9(6), 703-719. https://doi.org/10.4161/rna.20481

Larson, M. H., Gilbert, L. A., Wang, X., Lim, W. A., Weissman, J. S., & Qi, L. S. (2013). CRISPR interference (CRISPRi) for sequence-specific control of gene expression. *Nat. Protocols,* 8(11), 2180-2196. Retrieved from http://dx.doi.org/10.1038/nprot.2013.132

Ma, L., Bajic, V. B., & Zhang, Z. (2013). On the classification of long non-coding RNAs. *RNA Biology,* 10(6), 924-933. https://doi.org/10.4161/rna.24604

Maris, J. M. (2010). Recent Advances in Neuroblastoma. *New England Journal of Medicine,* 362(23), 2202-2211. https://doi.org/10.1056/NEJMra0804577

Pandey, G. K., & Kanduri, C. (2015). Long noncoding RNAs and neuroblastoma. *Oncotarget,* 6(21), 18265-18275. Retrieved from http://eurpepmc.org/abstract/MED/26087192

Park, J. R., Eggert, A., & Caron, H. (2010). Neuroblastoma: Biology, Prognosis, and Treatment. *Hematology/Oncology Clinics of North America,* 24(1), 65-86. https://doi.org/https://doi.org/10.1016/j.hoc.2009.11.011

The invention claimed is:

1. A method of treating a subject having neuroblastoma, the method comprising:
   administering an inhibitor of functional expression of LINC00682 to the subject to treat the neuroblastoma, wherein the inhibitor is selected from the group consisting of an antisense oligomer, a gapmer, an shRNA, an siRNA, a CRISPR, a TALEN, and a Zinc-finger nuclease.

2. The method according to claim 1, wherein apoptosis is thereby selectively induced in neuroblastoma cells of the subject.

3. An in vitro method of determining a presence of neuroblastoma in a subject, the method comprising:
   determining levels of LINC00682 in a sample of the subject;
   correlating levels of LINC00682 in the sample with the presence of neuroblastoma; and
   treating the subject for neuroblastoma.

4. The method according to claim 3, wherein the sample is a blood or serum sample.

5. The method according to claim 3, further comprising: correlating the levels of LINC00682 in the sample with a stage of neuroblastoma.

6. The method according to claim 4, further comprising: correlating the levels of LINC00682 in the blood or serum sample with a stage of neuroblastoma.

7. A method of treating a subject for a neuroblastoma tumor, the method comprising:
   determining whether expression of LINC00682 is present in the neuroblastoma tumor or a sample of neuroblastoma tumor cells taken from the subject,
   establishing whether the neuroblastoma tumor is suitable for treatment, wherein the presence of expression of LINC00682 in the neuroblastoma tumor or sample of neuroblastoma tumor cells is indicative of suitability for treatment, and
   when there is expression of LINC00682 in the neuroblastoma tumor or sample of neuroblastoma tumor cells, administering an inhibitor of functional expression of LINC00682 so as to treat the subject.

8. A method of treating a subject for a neuroblastoma tumor, the method comprising:
   determining whether an increased expression of LINC00682 is present in the neuroblastoma tumor or a sample of neuroblastoma tumor cells taken from the subject,
   establishing whether the neuroblastoma tumor is suitable for treatment, wherein the presence of an increased expression of LINC00682 in the neuroblastoma tumor or sample of neuroblastoma tumor cells is indicative of suitability for treatment, and,
   when there is an increased expression of LINC00682 in the neuroblastoma tumor or sample of neuroblastoma tumor cells, administering an inhibitor of functional expression of LINC00682 so as to treat the subject.

* * * * *